(12) United States Patent
Simon et al.

(10) Patent No.: US 10,980,919 B2
(45) Date of Patent: Apr. 20, 2021

(54) METHODS FOR IN VIVO AND IN VITRO USE OF GRAPHENE AND OTHER TWO-DIMENSIONAL MATERIALS

(71) Applicant: Lockheed Martin Corporation, Bethesda, MD (US)

(72) Inventors: Sarah M. Simon, Baltimore, MD (US); Jacob L. Swett, Redwood City, CA (US)

(73) Assignee: Lockheed Martin Corporation, Bethesda, MD (US)

( * ) Notice: Subject to any disclaimer, the term of this patent is extended or adjusted under 35 U.S.C. 154(b) by 0 days.

(21) Appl. No.: 15/099,304

(22) Filed: Apr. 14, 2016

(65) Prior Publication Data

US 2017/0296706 A1    Oct. 19, 2017

(51) Int. Cl.
| | | |
|---|---|---|
| *A61L 31/02* | (2006.01) | |
| *A61L 31/16* | (2006.01) | |
| *B01D 35/06* | (2006.01) | |
| *B01D 61/28* | (2006.01) | |
| *B01D 71/02* | (2006.01) | |

(Continued)

(52) U.S. Cl.
CPC ............ *A61L 31/024* (2013.01); *A61L 31/16* (2013.01); *B01D 35/06* (2013.01); *B01D 61/28* (2013.01); *B01D 67/0072* (2013.01); *B01D 69/10* (2013.01); *B01D 69/12* (2013.01); *B01D 71/021* (2013.01)

(58) Field of Classification Search
CPC ... A61L 31/024; A61L 31/16; B01D 67/0072; B01D 69/12; B01D 69/10; B01D 71/021; B01D 61/28; B01D 35/06
See application file for complete search history.

(56) References Cited

U.S. PATENT DOCUMENTS

| | | |
|---|---|---|
| 2,187,417 A | 1/1940 | Doble |
| 3,024,153 A | 3/1962 | Kennedy |

(Continued)

FOREIGN PATENT DOCUMENTS

| | | |
|---|---|---|
| CA | 2037988 | 9/1992 |
| CA | 2411935 | 12/2002 |

(Continued)

OTHER PUBLICATIONS

Bai (Nature Nanotechnology vol. 5, pp. 190-194 (2010).*

(Continued)

*Primary Examiner* — Krishnan S Menon

(74) *Attorney, Agent, or Firm* — Foley & Lardner LLP

(57) ABSTRACT

Two-dimensional materials, particularly graphene-based materials, having a plurality of apertures thereon can be formed into enclosures for various substances and introduced to an environment, particularly a biological environment (in vivo or in vitro). One or more selected substances can be released into the environment, one or more selected substances from the environment can enter the enclosure, one or more selected substances from the environment can be prevented from entering the enclosure, one or more selected substances can be retained within the enclosure, or combinations thereof. The enclosure can for example allow a sense-response paradigm to be realized. The enclosure can for example provide immunoisolation for materials, such as living cells, retained therein.

22 Claims, 7 Drawing Sheets

(51) Int. Cl.
  *B01D 69/12* (2006.01)
  *B01D 69/10* (2006.01)
  *B01D 67/00* (2006.01)

(56) References Cited

U.S. PATENT DOCUMENTS

| | | | |
|---|---|---|---|
| 3,303,085 A | 2/1967 | Price et al. |
| 3,501,831 A | 3/1970 | Gordon |
| 3,593,854 A | 7/1971 | Swank |
| 3,692,059 A | 9/1972 | Ice, Jr. |
| 3,701,433 A | 10/1972 | Krakauer et al. |
| 3,802,972 A | 4/1974 | Fleischer et al. |
| 3,896,733 A | 7/1975 | Rosenberg |
| 4,043,331 A | 8/1977 | Martin et al. |
| 4,073,732 A | 2/1978 | Lauer et al. |
| 4,159,954 A | 7/1979 | Gangemi |
| 4,162,220 A | 7/1979 | Servas |
| 4,277,344 A | 7/1981 | Cadotte |
| 4,303,530 A | 12/1981 | Shah et al. |
| 4,457,747 A | 7/1984 | Tu |
| 4,743,371 A | 5/1988 | Servas et al. |
| 4,804,363 A | 2/1989 | Valeri |
| 4,855,058 A | 8/1989 | Holland et al. |
| 4,880,440 A | 11/1989 | Perrin |
| 4,889,626 A | 12/1989 | Browne |
| 4,891,134 A | 1/1990 | Vcelka |
| 4,925,560 A | 5/1990 | Sorrick |
| 4,935,207 A | 6/1990 | Stanbro et al. |
| 4,976,858 A | 12/1990 | Kadoya |
| 5,052,444 A | 10/1991 | Messerly et al. |
| 5,080,770 A | 1/1992 | Culkin |
| 5,082,476 A | 1/1992 | Kahlbaugh et al. |
| 5,156,628 A | 10/1992 | Kranz |
| 5,182,111 A | 1/1993 | Aebischer et al. |
| 5,185,086 A | 2/1993 | Kaali et al. |
| 5,201,767 A | 4/1993 | Caldarise et al. |
| 5,244,981 A | 9/1993 | Seidner et al. |
| 5,277,748 A | 1/1994 | Sakaguchi et al. |
| 5,314,492 A | 5/1994 | Hamilton et al. |
| 5,314,960 A | 5/1994 | Spinelli et al. |
| 5,314,961 A | 5/1994 | Anton et al. |
| 5,331,067 A | 7/1994 | Seidner et al. |
| 5,344,454 A | 9/1994 | Clarke et al. |
| 5,371,147 A | 12/1994 | Spinelli et al. |
| 5,425,858 A | 6/1995 | Farmer |
| 5,480,449 A | 1/1996 | Hamilton et al. |
| 5,514,181 A | 5/1996 | Light et al. |
| 5,516,522 A | 5/1996 | Peyman et al. |
| 5,549,697 A | 8/1996 | Caldarise |
| 5,562,944 A | 10/1996 | Kafrawy |
| 5,565,210 A | 10/1996 | Rosenthal et al. |
| 5,580,530 A | 12/1996 | Kowatsch et al. |
| 5,595,621 A | 1/1997 | Light et al. |
| 5,636,437 A | 6/1997 | Kaschmitter et al. |
| 5,639,275 A | 6/1997 | Baetge et al. |
| 5,641,323 A | 6/1997 | Caldarise |
| 5,658,334 A | 8/1997 | Caldarise et al. |
| 5,662,158 A | 9/1997 | Caldarise |
| 5,665,118 A | 9/1997 | Lasalle et al. |
| 5,671,897 A | 9/1997 | Ogg et al. |
| 5,679,232 A | 10/1997 | Fedor et al. |
| 5,679,249 A | 10/1997 | Fendya et al. |
| 5,687,788 A | 11/1997 | Caldarise et al. |
| 5,700,477 A | 12/1997 | Rosenthal et al. |
| 5,713,410 A | 2/1998 | Lasalle et al. |
| 5,716,412 A | 2/1998 | Decarlo et al. |
| 5,716,414 A | 2/1998 | Caldarise |
| 5,725,586 A | 3/1998 | Sommerich |
| 5,725,775 A | 3/1998 | Bene et al. |
| 5,731,360 A | 3/1998 | Pekala et al. |
| 5,733,503 A | 3/1998 | Kowatsch et al. |
| 5,746,272 A | 5/1998 | Mastrorio et al. |
| 5,782,286 A | 7/1998 | Sommerich |
| 5,782,289 A | 7/1998 | Mastrorio et al. |
| 5,788,916 A | 8/1998 | Caldarise |
| 5,800,828 A | 9/1998 | Dionne et al. |
| 5,808,312 A | 9/1998 | Fukuda |
| 5,868,727 A | 2/1999 | Barr et al. |
| 5,897,592 A | 4/1999 | Caldarise et al. |
| 5,902,762 A | 5/1999 | Mercuri et al. |
| 5,906,234 A | 5/1999 | Mastrorio et al. |
| 5,910,172 A | 6/1999 | Penenberg |
| 5,910,173 A | 6/1999 | Decarlo et al. |
| 5,913,998 A | 6/1999 | Butler et al. |
| 5,922,304 A | 7/1999 | Unger |
| 5,925,247 A | 7/1999 | Huebbel |
| 5,932,185 A | 8/1999 | Pekala et al. |
| 5,935,084 A | 8/1999 | Southworth |
| 5,935,172 A | 8/1999 | Ochoa et al. |
| 5,954,937 A | 9/1999 | Farmer |
| 5,974,973 A | 11/1999 | Tittgemeyer |
| 5,976,555 A | 11/1999 | Liu et al. |
| 5,980,718 A | 11/1999 | Van Konynenburg et al. |
| 6,008,431 A | 12/1999 | Caldarise et al. |
| 6,013,080 A | 1/2000 | Khalili |
| 6,022,509 A | 2/2000 | Matthews et al. |
| 6,052,608 A | 4/2000 | Young et al. |
| 6,080,393 A | 6/2000 | Liu et al. |
| 6,093,209 A | 7/2000 | Sanders |
| 6,139,585 A | 10/2000 | Li |
| 6,152,882 A | 11/2000 | Prutchi |
| 6,156,323 A | 12/2000 | Verdicchio et al. |
| 6,193,956 B1 | 2/2001 | Liu et al. |
| 6,209,621 B1 | 4/2001 | Treacy |
| 6,213,124 B1 | 4/2001 | Butterworth |
| 6,228,123 B1 | 5/2001 | Dezzani |
| 6,264,699 B1 | 7/2001 | Noiles et al. |
| 6,292,704 B1 | 9/2001 | Malonek et al. |
| 6,309,532 B1 | 10/2001 | Tran et al. |
| 6,346,187 B1 | 2/2002 | Tran et al. |
| 6,375,014 B1 | 4/2002 | Garcera et al. |
| 6,423,022 B1 | 7/2002 | Roeher et al. |
| 6,426,214 B1 | 7/2002 | Butler et al. |
| 6,454,095 B1 | 9/2002 | Brisebois et al. |
| 6,455,115 B1 | 9/2002 | Demeyer |
| 6,461,622 B2 | 10/2002 | Liu et al. |
| 6,462,935 B1 | 10/2002 | Shiue et al. |
| 6,521,865 B1 | 2/2003 | Jones et al. |
| 6,532,386 B2 | 3/2003 | Sun et al. |
| 6,544,316 B2 | 4/2003 | Baker et al. |
| 6,580,598 B2 | 6/2003 | Shiue et al. |
| 6,654,229 B2 | 11/2003 | Yanagisawa et al. |
| 6,659,298 B2 | 12/2003 | Wong |
| 6,660,150 B2 | 12/2003 | Conlan et al. |
| 6,661,643 B2 | 12/2003 | Shiue et al. |
| 6,686,437 B2 | 2/2004 | Buchman et al. |
| 6,692,627 B1 | 2/2004 | Russell et al. |
| 6,695,880 B1 | 2/2004 | Roffman et al. |
| 6,699,684 B2 | 3/2004 | Ho et al. |
| 6,719,740 B2 | 4/2004 | Burnett et al. |
| 6,905,612 B2 | 6/2005 | Dorian et al. |
| 6,924,190 B2 | 8/2005 | Dennison |
| 7,014,829 B2 | 3/2006 | Yanagisawa et al. |
| 7,071,406 B2 | 7/2006 | Smalley et al. |
| 7,092,753 B2 | 8/2006 | Darvish et al. |
| 7,138,042 B2 | 11/2006 | Tran et al. |
| 7,171,263 B2 | 1/2007 | Darvish et al. |
| 7,175,783 B2 | 2/2007 | Curran |
| 7,179,419 B2 | 2/2007 | Lin et al. |
| 7,190,997 B1 | 3/2007 | Darvish et al. |
| 7,267,753 B2 | 9/2007 | Anex et al. |
| 7,306,768 B2 | 12/2007 | Chiga |
| 7,357,255 B2 | 4/2008 | Ginsberg et al. |
| 7,374,677 B2 | 5/2008 | McLaughlin et al. |
| 7,381,707 B2 | 6/2008 | Lin et al. |
| 7,382,601 B2 | 6/2008 | Yoshimitsu |
| 7,434,692 B2 | 10/2008 | Ginsberg et al. |
| 7,452,547 B2 | 11/2008 | Lambino et al. |
| 7,459,121 B2 | 12/2008 | Liang et al. |
| 7,460,907 B1 | 12/2008 | Darvish et al. |
| 7,476,222 B2 | 1/2009 | Sun et al. |
| 7,477,939 B2 | 1/2009 | Sun et al. |
| 7,477,940 B2 | 1/2009 | Sun et al. |
| 7,477,941 B2 | 1/2009 | Sun et al. |

(56) References Cited

U.S. PATENT DOCUMENTS

| | | |
|---|---|---|
| 7,479,133 B2 | 1/2009 | Sun et al. |
| 7,505,250 B2 | 3/2009 | Cho et al. |
| 7,531,094 B2 | 5/2009 | McLaughlin et al. |
| 7,600,567 B2 | 10/2009 | Christopher et al. |
| 7,631,764 B2 | 12/2009 | Ginsberg et al. |
| 7,650,805 B2 | 1/2010 | Nauseda et al. |
| 7,674,477 B1 | 3/2010 | Schmid et al. |
| 7,706,128 B2 | 4/2010 | Bourcier |
| 7,732,301 B1 | 6/2010 | Pinnington et al. |
| 7,761,809 B2 | 7/2010 | Bukovec et al. |
| 7,786,086 B2 | 8/2010 | Reches et al. |
| 7,866,475 B2 | 1/2011 | Doskoczynski et al. |
| 7,875,293 B2 | 1/2011 | Shults et al. |
| 7,935,331 B2 | 5/2011 | Lin |
| 7,935,416 B2 | 5/2011 | Yang et al. |
| 7,943,167 B2 | 5/2011 | Kulkarni et al. |
| 7,960,708 B2 | 6/2011 | Wolfe et al. |
| 7,998,246 B2 | 8/2011 | Liu et al. |
| 8,109,893 B2 | 2/2012 | Lande |
| 8,147,599 B2 | 4/2012 | McAlister |
| 8,262,943 B2 | 9/2012 | Meng et al. |
| 8,278,106 B2 | 10/2012 | Martinson et al. |
| 8,308,702 B2 | 11/2012 | Batchvarova et al. |
| 8,316,865 B2 | 11/2012 | Ochs et al. |
| 8,329,476 B2 | 12/2012 | Pitkanen et al. |
| 8,354,296 B2 | 1/2013 | Dimitrakopoulos et al. |
| 8,361,321 B2 | 1/2013 | Stetson et al. |
| 8,449,504 B2 | 5/2013 | Carter et al. |
| 8,471,562 B2 | 6/2013 | Knizhnik |
| 8,475,689 B2 | 7/2013 | Sun et al. |
| 8,506,807 B2 | 8/2013 | Lee et al. |
| 8,512,669 B2 | 8/2013 | Hauck |
| 8,513,324 B2 | 8/2013 | Scales et al. |
| 8,535,726 B2 | 9/2013 | Dai et al. |
| 8,592,291 B2 | 11/2013 | Shi et al. |
| 8,617,411 B2 | 12/2013 | Singh |
| 8,666,471 B2 | 3/2014 | Rogers et al. |
| 8,686,249 B1 | 4/2014 | Whitaker et al. |
| 8,697,230 B2 | 4/2014 | Ago et al. |
| 8,698,481 B2 | 4/2014 | Lieber et al. |
| 8,715,329 B2 | 5/2014 | Robinson et al. |
| 8,721,074 B2 | 5/2014 | Pugh et al. |
| 8,734,421 B2 | 5/2014 | Sun et al. |
| 8,744,567 B2 | 6/2014 | Fassih et al. |
| 8,751,015 B2 | 6/2014 | Frewin et al. |
| 8,753,468 B2 | 6/2014 | Caldwell et al. |
| 8,759,153 B2 | 6/2014 | Elian et al. |
| 8,808,257 B2 | 8/2014 | Pugh et al. |
| 8,828,211 B2 | 9/2014 | Garaj et al. |
| 8,840,552 B2 | 9/2014 | Brauker et al. |
| 8,857,983 B2 | 10/2014 | Pugh et al. |
| 8,861,821 B2 | 10/2014 | Osumi |
| 8,894,201 B2 | 11/2014 | Pugh et al. |
| 8,940,552 B2 | 1/2015 | Pugh et al. |
| 8,950,862 B2 | 2/2015 | Pugh et al. |
| 8,974,055 B2 | 3/2015 | Pugh et al. |
| 8,975,121 B2 | 3/2015 | Pugh et al. |
| 8,979,978 B2 | 3/2015 | Miller et al. |
| 8,986,932 B2 | 3/2015 | Turner et al. |
| 8,993,234 B2 | 3/2015 | Turner et al. |
| 8,993,327 B2 | 3/2015 | McKnight et al. |
| 9,014,639 B2 | 4/2015 | Pugh et al. |
| 9,017,937 B1 | 4/2015 | Turner et al. |
| 9,023,220 B2 | 5/2015 | Zurutuza Elorza et al. |
| 9,028,663 B2 | 5/2015 | Stetson et al. |
| 9,035,282 B2 | 5/2015 | Dimitrakopoulos et al. |
| 9,045,847 B2 | 6/2015 | Batchvarova et al. |
| 9,050,452 B2 | 6/2015 | Sun et al. |
| 9,052,533 B2 | 6/2015 | Pugh et al. |
| 9,056,282 B2 | 6/2015 | Miller et al. |
| 9,062,180 B2 | 6/2015 | Scales et al. |
| 9,067,811 B1 | 6/2015 | Bennett et al. |
| 9,070,615 B2 | 6/2015 | Elian et al. |
| 9,075,009 B2 | 7/2015 | Kim et al. |
| 9,080,267 B2 | 7/2015 | Batchvarova et al. |
| 9,095,821 B1 | 8/2015 | Ratto et al. |
| 9,095,823 B2 | 8/2015 | Fleming |
| 9,096,050 B2 | 8/2015 | Bedell et al. |
| 9,096,437 B2 | 8/2015 | Tour et al. |
| 9,102,111 B2 | 8/2015 | Pugh et al. |
| 9,108,158 B2 | 8/2015 | Yu et al. |
| 9,110,310 B2 | 8/2015 | Pugh et al. |
| 9,125,715 B2 | 9/2015 | Pugh et al. |
| 9,134,546 B2 | 9/2015 | Pugh et al. |
| 9,156,700 B2 | 10/2015 | Zhamu et al. |
| 9,170,646 B2 | 10/2015 | Toner et al. |
| 9,185,486 B2 | 11/2015 | Pugh |
| 9,193,587 B2 | 11/2015 | Bennett |
| 9,195,075 B2 | 11/2015 | Pugh et al. |
| 9,225,375 B2 | 12/2015 | Pugh et al. |
| 9,388,048 B1 | 7/2016 | Zhou et al. |
| 9,425,709 B2 | 8/2016 | Hayashi et al. |
| 9,437,370 B2 | 9/2016 | Chen et al. |
| 9,463,421 B2 | 10/2016 | Fleming |
| 9,475,709 B2 | 10/2016 | Stetson et al. |
| 9,505,192 B2 | 11/2016 | Stoltenberg et al. |
| 9,545,600 B2 | 1/2017 | Miller et al. |
| 9,567,224 B2 | 2/2017 | Bedworth |
| 9,572,918 B2 | 2/2017 | Bachmann et al. |
| 9,592,475 B2 | 3/2017 | Stoltenberg et al. |
| 9,610,546 B2 | 4/2017 | Sinton et al. |
| 9,656,214 B2 | 5/2017 | Miller et al. |
| 9,708,640 B2 | 7/2017 | Wu et al. |
| 9,713,794 B2 | 7/2017 | Choi et al. |
| 9,742,001 B2 | 8/2017 | Zhamu et al. |
| 9,744,617 B2 | 8/2017 | Bedworth et al. |
| 9,870,895 B2 | 1/2018 | Bedworth |
| 10,005,038 B2 | 6/2018 | Stetson, Jr. et al. |
| 10,017,852 B2 | 7/2018 | Heise et al. |
| 10,096,679 B1 | 10/2018 | Antunez et al. |
| 10,118,130 B2 | 11/2018 | Swett |
| 10,124,299 B2 | 11/2018 | Kim et al. |
| 10,130,919 B1 | 11/2018 | Saleh |
| 10,293,295 B2 | 5/2019 | Wang et al. |
| 10,376,845 B2 | 8/2019 | Swett et al. |
| 2001/0036556 A1 | 11/2001 | Jen |
| 2001/0047157 A1 | 11/2001 | Burnett et al. |
| 2001/0055597 A1 | 12/2001 | Liu et al. |
| 2002/0079004 A1 | 6/2002 | Sato et al. |
| 2002/0079054 A1 | 6/2002 | Nakatani |
| 2002/0104435 A1 | 8/2002 | Baker et al. |
| 2002/0115957 A1 | 8/2002 | Sun et al. |
| 2002/0117659 A1 | 8/2002 | Lieber et al. |
| 2002/0183682 A1 | 12/2002 | Darvish et al. |
| 2002/0183686 A1 | 12/2002 | Darvish et al. |
| 2003/0052354 A1 | 3/2003 | Dennison |
| 2003/0134281 A1 | 7/2003 | Evans |
| 2003/0138777 A1 | 7/2003 | Evans |
| 2003/0146221 A1 | 8/2003 | Lauer et al. |
| 2003/0159985 A1 | 8/2003 | Siwy et al. |
| 2003/0171053 A1* | 9/2003 | Sanders .............. B32B 5/02 442/340 |
| 2004/0018583 A1 | 1/2004 | Ho et al. |
| 2004/0035787 A1 | 2/2004 | Tanga et al. |
| 2004/0061253 A1 | 4/2004 | Kleinmeyer et al. |
| 2004/0063097 A1 | 4/2004 | Evans |
| 2004/0099324 A1 | 5/2004 | Fraser et al. |
| 2004/0111968 A1 | 6/2004 | Day et al. |
| 2004/0112865 A1 | 6/2004 | McCullough et al. |
| 2004/0121488 A1 | 6/2004 | Chang et al. |
| 2004/0140041 A1 | 7/2004 | Glick |
| 2004/0142463 A1 | 7/2004 | Walker et al. |
| 2004/0185730 A1 | 9/2004 | Lambino et al. |
| 2004/0193043 A1 | 9/2004 | Duchon et al. |
| 2004/0199243 A1 | 10/2004 | Yodfat |
| 2004/0208796 A1 | 10/2004 | Chiga |
| 2004/0217036 A1 | 11/2004 | Ginsberg et al. |
| 2004/0241214 A1 | 12/2004 | Kirkwood et al. |
| 2004/0251136 A1 | 12/2004 | Lean et al. |
| 2005/0004508 A1 | 1/2005 | Sun et al. |
| 2005/0004509 A1 | 1/2005 | Sun et al. |
| 2005/0004550 A1 | 1/2005 | Sun et al. |
| 2005/0010161 A1 | 1/2005 | Sun et al. |
| 2005/0010192 A1 | 1/2005 | Sun et al. |

(56) References Cited

U.S. PATENT DOCUMENTS

| | | |
|---|---|---|
| 2005/0015042 A1 | 1/2005 | Sun et al. |
| 2005/0053563 A1 | 3/2005 | Manissier et al. |
| 2005/0112078 A1 | 5/2005 | Boddupalli et al. |
| 2005/0126966 A1 | 6/2005 | Tanida et al. |
| 2005/0129633 A1 | 6/2005 | Lin |
| 2005/0148996 A1 | 7/2005 | Sun et al. |
| 2005/0170089 A1 | 8/2005 | Lashmore et al. |
| 2005/0189673 A1 | 9/2005 | Klug et al. |
| 2005/0226834 A1 | 10/2005 | Lambino et al. |
| 2005/0238730 A1 | 10/2005 | Le Fur et al. |
| 2006/0005381 A1 | 1/2006 | Nishi et al. |
| 2006/0036332 A1 | 2/2006 | Jennings |
| 2006/0073370 A1 | 4/2006 | Krusic et al. |
| 2006/0093885 A1 | 5/2006 | Krusic et al. |
| 2006/0121279 A1 | 6/2006 | Petrik |
| 2006/0151382 A1 | 7/2006 | Petrik |
| 2006/0166347 A1 | 7/2006 | Faulstich et al. |
| 2006/0180604 A1 | 8/2006 | Ginsberg et al. |
| 2006/0222701 A1 | 10/2006 | Kulkarni et al. |
| 2006/0253078 A1 | 11/2006 | Wu et al. |
| 2007/0004640 A1 | 1/2007 | Lin et al. |
| 2007/0032054 A1 | 2/2007 | Ramaswamy et al. |
| 2007/0056894 A1 | 3/2007 | Connors, Jr. |
| 2007/0060862 A1 | 3/2007 | Sun et al. |
| 2007/0062856 A1 | 3/2007 | Pahl et al. |
| 2007/0099813 A1 | 5/2007 | Luizzi et al. |
| 2007/0131646 A1 | 6/2007 | Donnelly et al. |
| 2007/0284279 A1 | 12/2007 | Doskoczynski et al. |
| 2008/0017564 A1 | 1/2008 | Hammond |
| 2008/0035484 A1 | 2/2008 | Wu et al. |
| 2008/0035541 A1 | 2/2008 | Franzreb et al. |
| 2008/0045877 A1 | 2/2008 | Levin et al. |
| 2008/0061477 A1 | 3/2008 | Capizzo |
| 2008/0063585 A1 | 3/2008 | Smalley et al. |
| 2008/0081323 A1 | 4/2008 | Keeley et al. |
| 2008/0081362 A1 | 4/2008 | Keeley et al. |
| 2008/0149561 A1 | 6/2008 | Chu et al. |
| 2008/0156648 A1 | 7/2008 | Dudziak et al. |
| 2008/0170982 A1 | 7/2008 | Zhang et al. |
| 2008/0185293 A1 | 8/2008 | Klose et al. |
| 2008/0188836 A1 | 8/2008 | Weber et al. |
| 2008/0190508 A1 | 8/2008 | Booth et al. |
| 2008/0241085 A1 | 10/2008 | Lin et al. |
| 2008/0268016 A1 | 10/2008 | Fang et al. |
| 2008/0290020 A1 | 11/2008 | Marand et al. |
| 2008/0290111 A1 | 11/2008 | Ginsberg et al. |
| 2009/0023572 A1 | 1/2009 | Backes et al. |
| 2009/0032475 A1 | 2/2009 | Ferrer et al. |
| 2009/0039019 A1 | 2/2009 | Raman |
| 2009/0048685 A1 | 2/2009 | Frigstad et al. |
| 2009/0075371 A1 | 3/2009 | Keeley et al. |
| 2009/0078640 A1 | 3/2009 | Chu et al. |
| 2009/0087395 A1 | 4/2009 | Lin et al. |
| 2009/0117335 A1 | 5/2009 | Iyoda et al. |
| 2009/0120873 A1 | 5/2009 | Becker et al. |
| 2009/0148495 A1 | 6/2009 | Hammer et al. |
| 2009/0176159 A1 | 7/2009 | Zhamu et al. |
| 2009/0192474 A1* | 7/2009 | Wei ............... A61F 2/4601 604/285 |
| 2009/0222072 A1 | 9/2009 | Robinson et al. |
| 2009/0236295 A1 | 9/2009 | Braun et al. |
| 2009/0241242 A1 | 10/2009 | Beatty et al. |
| 2009/0291270 A1 | 11/2009 | Zettl et al. |
| 2009/0294300 A1 | 12/2009 | Kanzius et al. |
| 2009/0306364 A1 | 12/2009 | Beer et al. |
| 2010/0000754 A1 | 1/2010 | Mann et al. |
| 2010/0016778 A1 | 1/2010 | Chattopadhyay |
| 2010/0021708 A1 | 1/2010 | Kong et al. |
| 2010/0024722 A1 | 2/2010 | Ochs et al. |
| 2010/0024838 A1 | 2/2010 | Ochs et al. |
| 2010/0025330 A1 | 2/2010 | Ratto et al. |
| 2010/0055464 A1 | 3/2010 | Sung |
| 2010/0059378 A1 | 3/2010 | Elson et al. |
| 2010/0072643 A1 | 3/2010 | Pugh et al. |
| 2010/0076553 A1 | 3/2010 | Pugh et al. |
| 2010/0098741 A1* | 4/2010 | Ranade ............. A61L 27/303 424/423 |
| 2010/0105834 A1 | 4/2010 | Tour et al. |
| 2010/0110372 A1 | 5/2010 | Pugh et al. |
| 2010/0124564 A1 | 5/2010 | Martinson et al. |
| 2010/0127312 A1 | 5/2010 | Grebel et al. |
| 2010/0161014 A1 | 6/2010 | Lynch et al. |
| 2010/0167551 A1 | 7/2010 | Dedontney |
| 2010/0196439 A1 | 8/2010 | Beck et al. |
| 2010/0209330 A1 | 8/2010 | Golzhauser et al. |
| 2010/0209515 A1 | 8/2010 | Chantalat et al. |
| 2010/0213079 A1 | 8/2010 | Willis |
| 2010/0224555 A1 | 9/2010 | Hoek et al. |
| 2010/0228204 A1 | 9/2010 | Beatty et al. |
| 2010/0233781 A1 | 9/2010 | Bangera et al. |
| 2010/0249273 A1 | 9/2010 | Scales et al. |
| 2010/0258111 A1 | 10/2010 | Shah et al. |
| 2010/0323177 A1 | 12/2010 | Ruoff et al. |
| 2010/0327847 A1 | 12/2010 | Leiber et al. |
| 2011/0014217 A1 | 1/2011 | Fahmy et al. |
| 2011/0027599 A1 | 2/2011 | Hoek et al. |
| 2011/0037033 A1 | 2/2011 | Green et al. |
| 2011/0041519 A1 | 2/2011 | McAlister |
| 2011/0041687 A1 | 2/2011 | Diaz et al. |
| 2011/0045523 A1 | 2/2011 | Strano et al. |
| 2011/0054418 A1 | 3/2011 | Pugh et al. |
| 2011/0054576 A1 | 3/2011 | Robinson et al. |
| 2011/0056892 A1 | 3/2011 | Lancaster |
| 2011/0073563 A1 | 3/2011 | Chang et al. |
| 2011/0092054 A1 | 4/2011 | Seo et al. |
| 2011/0092949 A1 | 4/2011 | Wang |
| 2011/0100921 A1 | 5/2011 | Heinrich |
| 2011/0112484 A1 | 5/2011 | Carter et al. |
| 2011/0118655 A1 | 5/2011 | Fassih et al. |
| 2011/0120970 A1 | 5/2011 | Joo et al. |
| 2011/0124253 A1 | 5/2011 | Shah et al. |
| 2011/0132834 A1 | 6/2011 | Tomioka et al. |
| 2011/0139707 A1 | 6/2011 | Siwy et al. |
| 2011/0152795 A1 | 6/2011 | Aledo et al. |
| 2011/0186449 A1 | 8/2011 | Clochard et al. |
| 2011/0189440 A1 | 8/2011 | Appleby et al. |
| 2011/0201201 A1 | 8/2011 | Arnold et al. |
| 2011/0202201 A1 | 8/2011 | Matsubara |
| 2011/0253630 A1 | 10/2011 | Bakajin et al. |
| 2011/0258791 A1 | 10/2011 | Batchvarova et al. |
| 2011/0258796 A1 | 10/2011 | Batchvarova et al. |
| 2011/0262645 A1 | 10/2011 | Batchvarova et al. |
| 2011/0263912 A1 | 10/2011 | Miller et al. |
| 2011/0269920 A1 | 11/2011 | Min et al. |
| 2012/0000845 A1 | 1/2012 | Park et al. |
| 2012/0031833 A1 | 2/2012 | Ho et al. |
| 2012/0048804 A1 | 3/2012 | Stetson et al. |
| 2012/0115243 A1 | 5/2012 | Pitkanen et al. |
| 2012/0116228 A1 | 5/2012 | Okubo |
| 2012/0145548 A1 | 6/2012 | Sivan et al. |
| 2012/0148633 A1 | 6/2012 | Sun et al. |
| 2012/0162600 A1 | 6/2012 | Pugh et al. |
| 2012/0183738 A1 | 7/2012 | Zettl et al. |
| 2012/0186850 A1 | 7/2012 | Sugiyama et al. |
| 2012/0211367 A1 | 8/2012 | Vecitis |
| 2012/0218508 A1 | 8/2012 | Pugh et al. |
| 2012/0219203 A1 | 8/2012 | Adachi |
| 2012/0220053 A1 | 8/2012 | Lee et al. |
| 2012/0234453 A1 | 9/2012 | Pugh et al. |
| 2012/0234679 A1 | 9/2012 | Garaj et al. |
| 2012/0235277 A1 | 9/2012 | Pugh et al. |
| 2012/0236254 A1 | 9/2012 | Pugh et al. |
| 2012/0236524 A1 | 9/2012 | Pugh et al. |
| 2012/0241371 A1 | 9/2012 | Revanur et al. |
| 2012/0242953 A1 | 9/2012 | Pugh et al. |
| 2012/0255899 A1 | 10/2012 | Choi et al. |
| 2012/0267337 A1 | 10/2012 | Striemer et al. |
| 2012/0292245 A1 | 11/2012 | Saito |
| 2012/0294793 A1 | 11/2012 | Chen et al. |
| 2012/0298396 A1 | 11/2012 | Hong et al. |
| 2012/0301707 A1 | 11/2012 | Kinloch et al. |
| 2013/0015136 A1 | 1/2013 | Bennett |
| 2013/0034760 A1 | 2/2013 | Otts et al. |
| 2013/0045523 A1 | 2/2013 | Leach et al. |

(56) References Cited

U.S. PATENT DOCUMENTS

| | | |
|---|---|---|
| 2013/0056367 A1 | 3/2013 | Martinez et al. |
| 2013/0071941 A1 | 3/2013 | Miller |
| 2013/0096292 A1 | 4/2013 | Brahmasandra et al. |
| 2013/0100436 A1 | 4/2013 | Jackson et al. |
| 2013/0105417 A1 | 5/2013 | Stetson et al. |
| 2013/0108839 A1 | 5/2013 | Arnold et al. |
| 2013/0116541 A1 | 5/2013 | Gracias et al. |
| 2013/0131214 A1 | 5/2013 | Scales et al. |
| 2013/0135578 A1 | 5/2013 | Pugh et al. |
| 2013/0146221 A1 | 6/2013 | Kolmakov et al. |
| 2013/0146480 A1 | 6/2013 | Garaj et al. |
| 2013/0152386 A1 | 6/2013 | Pandojirao-S et al. |
| 2013/0174968 A1* | 7/2013 | Vlassiouk .......... B82Y 30/00 156/155 |
| 2013/0174978 A1 | 7/2013 | Pugh et al. |
| 2013/0176030 A1 | 7/2013 | Simon |
| 2013/0190476 A1 | 7/2013 | Lancaster et al. |
| 2013/0192460 A1 | 8/2013 | Miller et al. |
| 2013/0192461 A1 | 8/2013 | Miller et al. |
| 2013/0194540 A1 | 8/2013 | Pugh et al. |
| 2013/0213568 A1 | 8/2013 | Pugh et al. |
| 2013/0215377 A1 | 8/2013 | Pugh et al. |
| 2013/0215378 A1 | 8/2013 | Pugh et al. |
| 2013/0215380 A1 | 8/2013 | Pugh et al. |
| 2013/0216581 A1 | 8/2013 | Fahmy et al. |
| 2013/0240355 A1 | 9/2013 | Ho et al. |
| 2013/0240437 A1 | 9/2013 | Rodrigues et al. |
| 2013/0248097 A1 | 9/2013 | Ploss, Jr. |
| 2013/0248367 A1 | 9/2013 | Stetson et al. |
| 2013/0249147 A1 | 9/2013 | Bedworth |
| 2013/0256118 A1 | 10/2013 | Meller et al. |
| 2013/0256139 A1 | 10/2013 | Peng |
| 2013/0256154 A1 | 10/2013 | Peng |
| 2013/0256210 A1 | 10/2013 | Fleming |
| 2013/0256211 A1 | 10/2013 | Fleming |
| 2013/0261568 A1 | 10/2013 | Martinson et al. |
| 2013/0269819 A1 | 10/2013 | Ruby et al. |
| 2013/0270188 A1 | 10/2013 | Karnik et al. |
| 2013/0273288 A1 | 10/2013 | Luo et al. |
| 2013/0277305 A1 | 10/2013 | Stetson et al. |
| 2013/0277573 A1 | 10/2013 | Miller et al. |
| 2013/0284665 A1 | 10/2013 | Lee et al. |
| 2013/0295150 A1 | 11/2013 | Chantalat et al. |
| 2013/0295374 A1 | 11/2013 | Tang et al. |
| 2013/0309776 A1 | 11/2013 | Drndic et al. |
| 2013/0317131 A1 | 11/2013 | Scales et al. |
| 2013/0317132 A1 | 11/2013 | Scales et al. |
| 2013/0317133 A1 | 11/2013 | Scales et al. |
| 2013/0323295 A1 | 12/2013 | Scales et al. |
| 2013/0330833 A1 | 12/2013 | Ruiz et al. |
| 2013/0335092 A1 | 12/2013 | Wu |
| 2013/0338611 A1 | 12/2013 | Pugh et al. |
| 2013/0338744 A1 | 12/2013 | Frewin et al. |
| 2014/0002788 A1 | 1/2014 | Otts et al. |
| 2014/0005514 A1 | 1/2014 | Pugh et al. |
| 2014/0015160 A1 | 1/2014 | Kung et al. |
| 2014/0017322 A1 | 1/2014 | Dai et al. |
| 2014/0021133 A1 | 1/2014 | Sivvy et al. |
| 2014/0030482 A1 | 1/2014 | Miller et al. |
| 2014/0048411 A1 | 2/2014 | Choi et al. |
| 2014/0066958 A1 | 3/2014 | Priewe |
| 2014/0079936 A1 | 3/2014 | Russo et al. |
| 2014/0093728 A1 | 4/2014 | Shah et al. |
| 2014/0128891 A1 | 5/2014 | Astani-Matthies et al. |
| 2014/0141521 A1 | 5/2014 | Peng et al. |
| 2014/0151288 A1 | 6/2014 | Miller et al. |
| 2014/0151631 A1 | 6/2014 | Duesberg et al. |
| 2014/0154464 A1 | 6/2014 | Miller et al. |
| 2014/0170195 A1 | 6/2014 | Fassih et al. |
| 2014/0171541 A1 | 6/2014 | Scales et al. |
| 2014/0174927 A1 | 6/2014 | Bash Ir et al. |
| 2014/0190004 A1 | 7/2014 | Riall et al. |
| 2014/0190550 A1 | 7/2014 | Loh et al. |
| 2014/0190676 A1 | 7/2014 | Zhamu et al. |
| 2014/0190833 A1 | 7/2014 | Lieber et al. |
| 2014/0192313 A1 | 7/2014 | Riall et al. |
| 2014/0192314 A1 | 7/2014 | Riall et al. |
| 2014/0199777 A2 | 7/2014 | Ruiz et al. |
| 2014/0209539 A1 | 7/2014 | El Badawi et al. |
| 2014/0212596 A1 | 7/2014 | Jahangiri-Famenini |
| 2014/0230653 A1 | 8/2014 | Yu et al. |
| 2014/0230733 A1 | 8/2014 | Miller |
| 2014/0231351 A1 | 8/2014 | Wickramasinghe et al. |
| 2014/0248621 A1 | 9/2014 | Collins |
| 2014/0253131 A1 | 9/2014 | Liu et al. |
| 2014/0257348 A1 | 9/2014 | Priewe et al. |
| 2014/0257515 A1 | 9/2014 | So et al. |
| 2014/0257517 A1 | 9/2014 | Deichmann et al. |
| 2014/0259657 A1 | 9/2014 | Riall et al. |
| 2014/0261999 A1 | 9/2014 | Stetson et al. |
| 2014/0263035 A1 | 9/2014 | Stoltenberg et al. |
| 2014/0263178 A1 | 9/2014 | Sinton et al. |
| 2014/0264977 A1 | 9/2014 | Pugh et al. |
| 2014/0268015 A1 | 9/2014 | Riall et al. |
| 2014/0268020 A1 | 9/2014 | Pugh et al. |
| 2014/0268021 A1 | 9/2014 | Pugh et al. |
| 2014/0268026 A1 | 9/2014 | Pugh et al. |
| 2014/0272286 A1* | 9/2014 | Stoltenberg .......... B32B 3/266 428/137 |
| 2014/0272522 A1 | 9/2014 | Pugh et al. |
| 2014/0273315 A1 | 9/2014 | Pugh et al. |
| 2014/0273316 A1 | 9/2014 | Pugh et al. |
| 2014/0276481 A1 | 9/2014 | Pugh et al. |
| 2014/0276999 A1 | 9/2014 | Harms et al. |
| 2014/0306361 A1 | 10/2014 | Pugh et al. |
| 2014/0308681 A1 | 10/2014 | Strano et al. |
| 2014/0311967 A1 | 10/2014 | Grossman et al. |
| 2014/0315213 A1 | 10/2014 | Nagrath et al. |
| 2014/0318373 A1 | 10/2014 | Wood et al. |
| 2014/0322518 A1 | 10/2014 | Addleman et al. |
| 2014/0333892 A1 | 11/2014 | Pugh et al. |
| 2014/0335661 A1 | 11/2014 | Pugh et al. |
| 2014/0343580 A1 | 11/2014 | Priewe |
| 2014/0346081 A1 | 11/2014 | Sowden et al. |
| 2014/0346631 A1 | 11/2014 | Karim et al. |
| 2014/0349892 A1 | 11/2014 | Van Der Zaag et al. |
| 2014/0350372 A1 | 11/2014 | Pugh et al. |
| 2014/0377651 A1 | 12/2014 | Kwon et al. |
| 2014/0377738 A1 | 12/2014 | Bachmann et al. |
| 2015/0015843 A1 | 1/2015 | Pugh et al. |
| 2015/0017918 A1 | 1/2015 | Pugh et al. |
| 2015/0050734 A1 | 2/2015 | Liedtke et al. |
| 2015/0053627 A1 | 2/2015 | Silin et al. |
| 2015/0057762 A1 | 2/2015 | Harms et al. |
| 2015/0061990 A1 | 3/2015 | Toner et al. |
| 2015/0062533 A1 | 3/2015 | Toner et al. |
| 2015/0063605 A1 | 3/2015 | Pugh |
| 2015/0066063 A1 | 3/2015 | Priewe |
| 2015/0075667 A1 | 3/2015 | McHugh et al. |
| 2015/0076056 A1 | 3/2015 | Iyuke et al. |
| 2015/0077658 A1 | 3/2015 | Pugh et al. |
| 2015/0077659 A1 | 3/2015 | Pugh et al. |
| 2015/0077660 A1 | 3/2015 | Pugh et al. |
| 2015/0077661 A1 | 3/2015 | Pugh et al. |
| 2015/0077662 A1 | 3/2015 | Pugh et al. |
| 2015/0077663 A1 | 3/2015 | Pugh et al. |
| 2015/0077699 A1 | 3/2015 | De Sio et al. |
| 2015/0077702 A9 | 3/2015 | Pugh et al. |
| 2015/0079683 A1 | 3/2015 | Yager et al. |
| 2015/0087249 A1 | 3/2015 | Pugh et al. |
| 2015/0096935 A1 | 4/2015 | Mitra et al. |
| 2015/0098910 A1 | 4/2015 | Mordas et al. |
| 2015/0101931 A1 | 4/2015 | Garaj et al. |
| 2015/0105686 A1 | 4/2015 | Vasan |
| 2015/0118318 A1 | 4/2015 | Fahmy et al. |
| 2015/0122727 A1 | 5/2015 | Karnik et al. |
| 2015/0137817 A1 | 5/2015 | Wilson et al. |
| 2015/0138454 A1 | 5/2015 | Pugh et al. |
| 2015/0142107 A1 | 5/2015 | Pugh et al. |
| 2015/0145155 A1 | 5/2015 | Pugh et al. |
| 2015/0146162 A1 | 5/2015 | Pugh et al. |
| 2015/0147474 A1 | 5/2015 | Batchvarova et al. |
| 2015/0151254 A1 | 6/2015 | Perez |
| 2015/0170788 A1 | 6/2015 | Miller et al. |

(56) References Cited

U.S. PATENT DOCUMENTS

| | | |
|---|---|---|
| 2015/0174253 A1 | 6/2015 | Sun et al. |
| 2015/0174254 A1 | 6/2015 | Sun et al. |
| 2015/0182473 A1 | 7/2015 | Bosnyak et al. |
| 2015/0185180 A1 | 7/2015 | Ruhl et al. |
| 2015/0196579 A1 | 7/2015 | Ferrante et al. |
| 2015/0196879 A1 | 7/2015 | Brinke-Seiferth et al. |
| 2015/0202351 A1 | 7/2015 | Kaplan et al. |
| 2015/0212339 A1 | 7/2015 | Pugh et al. |
| 2015/0217219 A1 | 8/2015 | Sinsabaugh et al. |
| 2015/0218210 A1 | 8/2015 | Stetson et al. |
| 2015/0221474 A1 | 8/2015 | Bedworth |
| 2015/0231557 A1 | 8/2015 | Miller et al. |
| 2015/0231577 A1 | 8/2015 | Nair et al. |
| 2015/0247178 A1 | 9/2015 | Mountcastle et al. |
| 2015/0248972 A1 | 9/2015 | Tang et al. |
| 2015/0258254 A1 | 9/2015 | Simon et al. |
| 2015/0258498 A1 | 9/2015 | Simon et al. |
| 2015/0258502 A1 | 9/2015 | Turowski |
| 2015/0258503 A1 | 9/2015 | Sinton et al. |
| 2015/0258506 A1 | 9/2015 | Mi et al. |
| 2015/0258525 A1 | 9/2015 | Westman et al. |
| 2015/0268150 A1 | 9/2015 | Newkirk et al. |
| 2015/0272834 A1 | 10/2015 | Sun et al. |
| 2015/0272896 A1 | 10/2015 | Sun et al. |
| 2015/0273401 A1 | 10/2015 | Miller et al. |
| 2015/0309337 A1 | 10/2015 | Flitsch et al. |
| 2015/0321147 A1 | 11/2015 | Fleming et al. |
| 2015/0321149 A1 | 11/2015 | McGinnis |
| 2015/0323811 A1 | 11/2015 | Flitsch et al. |
| 2015/0336202 A1 | 11/2015 | Bedworth et al. |
| 2015/0342900 A1 | 12/2015 | Putnins |
| 2015/0346382 A1 | 12/2015 | Bliven et al. |
| 2015/0351887 A1 | 12/2015 | Peters |
| 2015/0359742 A1 | 12/2015 | Fassih et al. |
| 2015/0376448 A1 | 12/2015 | Urs |
| 2015/0378176 A1 | 12/2015 | Flitsch et al. |
| 2016/0009049 A1 | 1/2016 | Stoltenberg et al. |
| 2016/0038885 A1 | 2/2016 | Hogen-Esch et al. |
| 2016/0043384 A1 | 2/2016 | Zhamu et al. |
| 2016/0058932 A1 | 3/2016 | Stetson et al. |
| 2016/0059190 A1 | 3/2016 | Yoo et al. |
| 2016/0067390 A1 | 3/2016 | Simon et al. |
| 2016/0074814 A1 | 3/2016 | Park et al. |
| 2016/0074815 A1 | 3/2016 | Sinton et al. |
| 2016/0084008 A1 | 3/2016 | Faircloth et al. |
| 2016/0084981 A1 | 3/2016 | Kayano et al. |
| 2016/0116237 A1 | 4/2016 | Alsadah et al. |
| 2016/0256805 A1 | 9/2016 | Grein et al. |
| 2016/0272499 A1 | 9/2016 | Waduge et al. |
| 2016/0282326 A1 | 9/2016 | Waduge et al. |
| 2016/0284811 A1 | 9/2016 | Yu et al. |
| 2016/0339160 A1 | 11/2016 | Bedworth et al. |
| 2017/0000937 A1 | 1/2017 | Gottschalk |
| 2017/0028640 A1 | 2/2017 | Harrison et al. |
| 2017/0032962 A1 | 2/2017 | Zurutuza Elorza et al. |
| 2017/0035943 A1 | 2/2017 | Simon et al. |
| 2017/0036916 A1 | 2/2017 | Bedworth et al. |
| 2017/0037356 A1 | 2/2017 | Simon et al. |
| 2017/0057812 A1 | 3/2017 | Zurutuza Elorza et al. |
| 2017/0065939 A1 | 3/2017 | Kim et al. |
| 2017/0144107 A1 | 5/2017 | Garaj et al. |
| 2017/0216923 A1 | 8/2017 | Babenko et al. |
| 2017/0217777 A1 | 8/2017 | Hong et al. |
| 2017/0239623 A1 | 8/2017 | Stoltenberg et al. |
| 2017/0296706 A1 | 10/2017 | Simon et al. |
| 2017/0296972 A1 | 10/2017 | Sinton et al. |
| 2017/0296976 A1 | 10/2017 | Liu et al. |
| 2017/0296979 A1 | 10/2017 | Swett et al. |
| 2018/0147542 A1 | 5/2018 | Jhon et al. |
| 2018/0207591 A1 | 7/2018 | Yu et al. |

FOREIGN PATENT DOCUMENTS

| | | |
|---|---|---|
| CN | 1128501 A | 8/1996 |
| CN | 101108194 A | 1/2008 |
| CN | 101243544 | 8/2008 |
| CN | 101428198 A | 5/2009 |
| CN | 101489653 A | 7/2009 |
| CN | 101996853 A | 3/2011 |
| CN | 102242062 A | 11/2011 |
| CN | 102344132 | 2/2012 |
| CN | 102423272 | 4/2012 |
| CN | 102592720 A | 7/2012 |
| CN | 101996853 B | 8/2012 |
| CN | 102637584 A | 8/2012 |
| CN | 103153441 | 6/2013 |
| CN | 103182249 A | 7/2013 |
| CN | 203235358 | 10/2013 |
| CN | 103480281 | 1/2014 |
| CN | 103585891 | 2/2014 |
| CN | 103603706 A | 2/2014 |
| DE | 19536560 | 3/1997 |
| DE | 10 2005 049 338 A1 | 4/2007 |
| EP | 0 364 628 A1 | 4/1990 |
| EP | 1 034 251 | 1/2004 |
| EP | 1 777 250 A1 | 4/2007 |
| EP | 1 872 812 | 1/2008 |
| EP | 2 060 286 | 5/2009 |
| EP | 2 107 120 A1 | 10/2009 |
| EP | 2 230 511 A1 | 9/2010 |
| EP | 1 603 609 | 5/2011 |
| EP | 2 354 272 | 8/2011 |
| EP | 2 450 096 | 5/2012 |
| EP | 2 489 520 | 8/2012 |
| EP | 2 511 002 | 10/2012 |
| EP | 2 586 473 | 5/2013 |
| EP | 2 679 540 | 1/2014 |
| EP | 2 937 313 | 10/2015 |
| EP | 2 995 368 A1 | 3/2016 |
| EP | 3 070 053 | 9/2016 |
| EP | 3 084 398 | 10/2016 |
| EP | 1 538 2430.5 | 3/2017 |
| EP | 3 135 631 | 3/2017 |
| JP | 59-102111 | 7/1984 |
| JP | 10-510471 | 5/1995 |
| JP | 7504120 | 5/1995 |
| JP | 2001-232158 | 8/2001 |
| JP | 2002-126510 | 5/2002 |
| JP | 2004-179014 | 6/2004 |
| JP | 2005-126966 | 5/2005 |
| JP | 2006-188393 | 7/2006 |
| JP | 2006-262891 A | 10/2006 |
| JP | 2009-291777 | 12/2009 |
| JP | 2011-168448 A | 9/2011 |
| JP | 2011-241479 | 12/2011 |
| JP | 2012-500708 | 1/2012 |
| JP | 2004-202480 | 7/2014 |
| JP | 2015-503405 | 2/2015 |
| JP | 2016-175828 | 10/2016 |
| KR | 102011008411 | 7/2011 |
| KR | 10-2012-0022164 A | 3/2012 |
| KR | 1020120022164 A | 3/2012 |
| KR | 1020140002570 | 1/2014 |
| WO | WO-93/33901 | 3/1993 |
| WO | WO-93/12859 | 8/1993 |
| WO | WO-95/00231 | 1/1995 |
| WO | WO-97/12664 A1 | 4/1997 |
| WO | WO-98/30501 A2 | 7/1998 |
| WO | WO-00/70012 | 11/2000 |
| WO | WO-02/055539 A1 | 7/2002 |
| WO | WO-2013/115762 | 8/2003 |
| WO | WO-2004/009840 A1 | 1/2004 |
| WO | WO-2004/082733 | 9/2004 |
| WO | WO-2005/047857 A2 | 5/2005 |
| WO | WO-2007/103411 A2 | 9/2007 |
| WO | WO-2007/140252 A1 | 12/2007 |
| WO | WO-2008/008533 | 1/2008 |
| WO | WO-2009/129984 A1 | 10/2009 |
| WO | WO-2010/006080 | 1/2010 |
| WO | WO-2010/115904 A1 | 10/2010 |
| WO | WO-2011/019686 A1 | 2/2011 |
| WO | WO-2011/046706 A1 | 4/2011 |
| WO | WO-2011/001674 | 6/2011 |
| WO | WO-2011/063458 A1 | 6/2011 |

(56) References Cited

FOREIGN PATENT DOCUMENTS

| WO | WO-2011/075158 | | 6/2011 |
|---|---|---|---|
| WO | WO-2011/094204 | A2 | 8/2011 |
| WO | WO-2011/100458 | A2 | 8/2011 |
| WO | WO-2011/138689 | A2 | 11/2011 |
| WO | WO-2012/006657 | A1 | 1/2012 |
| WO | WO-2012/021801 | A2 | 2/2012 |
| WO | WO-2012/027148 | A1 | 3/2012 |
| WO | WO-2012/028695 | | 3/2012 |
| WO | WO-2012/030368 | A1 | 3/2012 |
| WO | WO-2012/073998 | A1 | 6/2012 |
| WO | WO-2012/125770 | | 9/2012 |
| WO | WO-2012/138671 | A2 | 10/2012 |
| WO | WO-2012/142852 | A1 | 10/2012 |
| WO | WO-2013/016445 | A1 | 1/2013 |
| WO | WO-2013/048063 | A1 | 4/2013 |
| WO | WO-2013/138137 | A1 | 9/2013 |
| WO | WO-2013/138698 | A1 | 9/2013 |
| WO | WO-2013/142133 | | 9/2013 |
| WO | WO-2013/151799 | | 10/2013 |
| WO | WO-2013/152179 | A1 | 10/2013 |
| WO | WO-2014/038600 | A1 | 3/2014 |
| WO | WO-2014/084861 | A1 | 6/2014 |
| WO | WO2014084856 | * | 6/2014 |
| WO | WO-2014/159043 | | 10/2014 |
| WO | WO-2014/168629 | A1 | 10/2014 |
| WO | WO-2015/030698 | A1 | 3/2015 |
| WO | WO-2015/110277 | | 7/2015 |
| WO | WO-2015/116946 | | 8/2015 |
| WO | WO-2015/138736 | A1 | 9/2015 |
| WO | WO-2015/138752 | A1 | 9/2015 |
| WO | WO-2015/138771 | A1 | 9/2015 |
| WO | WO-2015/197217 | | 12/2015 |
| WO | WO-2016/102003 | | 6/2016 |

OTHER PUBLICATIONS

AE Search and Examination Report for United Arab Emirates Application No. P186/13 dated Oct. 4, 2016.
Agenor et al., "Renal tubular dysfunction in human visceral leishmaniasis (Kala-azar)," Clinical Nephrology 71(5): 492-500 (May 2009) (available online Mar. 21, 2011).
Albert et al., "Ringer's lactate is compatible with the rapid infusion of AS-3 preserved packed red blood cells," Can. J. Anaesth. 56(5): 352-356 (May 2009) (available online Apr. 2, 2009).
Aluru et al. "Modeling electronics on the nanoscale." Handbook of nanoscience, engineering and technology Goddard W, Brenner D, Lyshevski S, Iafrate GJ (2002): 11-1.
Alvarenga, "Carbon nanotube materials for aerospace wiring" Rochester Institute of Technology, 2010.
AMI Applied Membranes Inc., "Filmtec Nanofiltration Membrane Elements", Retrieved from appliedmembranes.corn/nanofiltration_elements.htm, accessed Apr. 28, 2015 (2 Pages).
Aso et al., "Comparison of serum high-molecular weight (HMW) adiponectin with total adiponectin concentrations in type 2 diabetic patients with coronary artery using a novel enzyme-linked immunosorbent assay to detect HMW adiponectin," Diabetes 55(7): 1954-1960 (Jul. 2006).
AU Examination Report for Australian Patent Application No. 2013235234, dated Jan. 13, 2017, 4 pages.
AU Notice of Acceptance for Australian Application No. 2011293742 dated Jan. 13, 2016.
Axelsson et al., "Acute hyperglycemia induces rapid, reversible increases in glomerular permeability in nondiabetic rats," AM. J. Physiol. Renal Physiol. 298(6): F1306-F1312 (Jun. 2010) (available online Mar. 17, 2010).
Bae et al. "Roll-to-roll production of 30-inch graphene films for transparent electrodes." Nature nanotechnology 5.8 (2010): 574-578.
Bains et al., "Novel lectins from rhizomes of two Acorus species with mitogenic activity and inhibitory potential towards murine cancer cell lines," Int'l Immunopharmacol. 5(9): 1470-1478 (Aug. 2005) (available online May 12, 2005).
Baker, "Membrane Technology and Applications", Membrane Technology and Applications; Apr. 14, 2004; pp. 92-94.
Barreiro et al. "Transport properties of graphene in the high-current limit." Physical review letters 103.7 (2009): 076601.
Bazargani et al. "Low molecular weight heparin improves peritoneal ultrafiltration and blocks complement and coagulation," Peritoneal Dialysis Int'l 25(4): 394-404 (Jul. 2005-Aug. 2005).
Bazargani, "Acute inflammation in peritoneal dialysis: experimental studies in rats. Characterization of regulatory mechanisms," Swedish Dental J. Supp. 171: 1-57, i (2005).
Beppu et al., "Antidiabetic effects of dietary administration of Aloe arborescens Miller components on multiple low-dose streptozotocin-induced diabetes in mice: investigation on hypoglycemic action and systemic absorption dynamics of aloe components," J. Ethnopharmacol. 103(3): 468-77 (Feb. 20, 2006) (available online Jan. 6, 2006).
Bieri et al. "Two-dimensional Polymer Formation on Surfaces: Insight into the Roles of Precursor Mobility and Reactivity" JACS, 2010, vol. 132, pp. 16669-16676.
Bruin et al., "Maturation and function of human embryonic stem cell-derived pancreatic progenitors in macroencapsulation devices following transplant into mice", Diabetologia (2013), vol. 56: 1987-1998 (Jun. 16, 2013).
Chu Ju, et al. "Modern Biotechnology" East China University of Technology Press, (Sep. 2007), vol. 1; pp. 306-307, ISBN 978-7-5628-2116-8.
Clochard, "Track-Etched Polymer Membranes," Laboratory of Irradiated Solids, Ecole Polytechnique, retrieved from http://www.lsi.polytechnique.fr/home/research/physics-and-chemistry-of-nano-objects/trac..., Accessed Jul. 30, 2015 (2 pages).
CN Notification of Grant for Chinese Application No. 201180049184.5 dated Jun. 6, 2016.
CN Office Action for Chinese Application No. 201380014845.X dated Jul. 8, 2016.
CN Office Action for Chinese Application No. 201380014845.X dated Sep. 2, 2015.
CN Office Action for Chinese Application No. 201380019165.5 dated Aug. 25, 2015.
CN Office Action for Chinese Application No. 201380073141.X dated Jun. 8, 2016.
CN Office Action for Chinese Application No. 201380073141.X dated Mar. 21, 2017.
CN Office Action for Chinese Application No. 201480015372.X dated Aug. 2, 2016.
CN Office Action for Chinese Application No. 20118004918.5 dated Jun. 15, 2015.
CN Office Action for Chinese Application No. 201180049184.5 dated Jul. 30, 2014.
CN Office Action for Chinese Application No. 201180049184.5 dated Mar. 4, 2016.
CN Office Action for Chinese Application No. 201380014845.X dated Dec. 23, 2016.
CN Office Action for Chinese Application No. 201380017644.5 dated Feb. 7, 2017.
CN Office Action for Chinese Application No. 201380017644.5 dated May 26, 2016.
CN Office Action for Chinese Application No. 201380017644.5 dated Sep. 29, 2015.
CN Office Action in Chinese Application No. 201380013988.9 dated Oct. 27, 2015.
Daniel et al. "Implantable Diagnostic Device for Cancer Monitoring." Biosens Bioelectricon. 24(11): 3252-3257 (Jul. 15, 2009).
Database WPI, Week 201238, Thomson Scientific, London, GB; AN 2012-D49442.
De Lannoy et al., "Aquatic Biofouling Prevention by Electrically Charged Nanocomposite Polymer Thin Film Membranes", 2013 American Water Work Association membrane Technology Conference; Environmental science & technology 47.6 (2013): 2760-2768.
Deng et al., "Renal protection in chronic kidney disease: hypoxia-inducible factor activation vs. angiotensin II blockade," Am. J. Physiol. Renal Physiol. 299(6): F1365-F1373 (Dec. 2010) (available online Sep. 29, 2010).

(56) References Cited

OTHER PUBLICATIONS

Edwards, "Large Sheets of Graphene Film Produced for Transparent Electrodes (w/ Video)"; (Jun. 21, 2010), PhysOrg.com, retrieved on May 15, 2017 from https://phys.org/news/2010-06-large-sheets-graphene-transparentelectrodes.html (2 pages).
EP Office Action for European Application No. 13715529.7 dated Jun. 24, 2016.
Fayerman, "Canadian scientists use stem cells to reverse diabetes in mice", The Telegraph-Journal (New Brunswick), 1-2 (Jun. 29, 2012).
Fayerman, "Diabetes reversed in mice; University of B.C. scientists use embryonic stem cells to deal with Type 1 disease", The Vancouver Sun (British Columbia), 1-2 (Jun. 28, 2012).
Fejes et al. "A review of the properties and CVD synthesis of coiled carbon nanotubes." Materials 3.4 (2010): 2618-2642.
Franzen, C. "MIT Setting Up Industrial-Scale Graphene Printing Press" Sep. 23, 2011, retrieved from http://talkingpointsmemo.com/idealab/mit-setting-up-industrial-scale-graphene-printing-press (2 pages).
Freedman et al., "Genetic basis of nondiabetic end-stage renal disease," Semin. Nephrol. 30(2): 101-110 (Mar. 2010).
Garcia-Lopez et al., "Determination of high and low molecular weight molecules of icodextrin in plasma and dialysate, using gel filtration chromatography, in peritoneal dialysis patients," Peritoneal Dialysis Int'l 25(2): 181-191 (Mar. 2005-Apr. 2005).
Georgakilas et al., "Functionalization of Graphene: Covalent and Non-Covalent Approaches, Derivatives and Applications," Chem. Rev., (2012) 112(11), pp. 6156-6214.
Gnudi "Molecular mechanisms of proteinuria in diabetes," Biochem. Soc. Trans. 36(5): 946-949 (Oct. 2008).
Gotloib et al., "Peritoneal dialysis in refractory end-stage congestive heart failure: a challenge facing a no-win situation," Nephrol. Dialysis. Transplant. 20(Supp. 7): vii32-vii36 (Jul. 2005).
Harvey "Carbon as conductor: a pragmatic view." Proceedings of the 61st IWCS Conference, http://www. iwcs. org/archives/56333-iwcs-2012b-1.1584632. vol. 1. 2012.
Hashimoto et al. "Direct evidence for atomic defects in graphene layers." Nature 430.7002 (2004): 870-873.
He, et al. "The attachment of Fe3 O4 nanoparticles to graphene oxide by covalent bonding." Carbon 48.11 (2010): 3139-3144.
Hone et al. "Graphene has record-breaking strength" Physicsworld.com, Jul. 17, 2008.
Huang et al., "Gene expression profile in circulating mononuclear cells afterexposure to ultrafine carbon particles," Inhalation Toxicol. 22(10): 835-846 (Aug. 2010).
Humplik, et al. "Nanostructured materials for water desalination." Nanotechnology 22.29 (2011): 292001.
International Search Report and Written Opinion dated Jan. 5, 2012 for related International Application No. PCT/US11/47800.
International Search Report and Written Opinion dated Mar. 12, 2014 for International Application No. PCT/US2013/074942.
International Search Report and Written Opinion for International Application No. PCT/US2011/047800 dated Jan. 5, 2012.
International Search Report and Written Opinion for PCT Application No. PCT/US2014/023027 dated Jun. 26, 2014.
International Search Report and Written Opinion in International Application No. PCT/US2013/030344 dated Jun. 19, 2013.
International Search Report and Written Opinion in International Application No. PCT/US2013/033035 dated Jun. 28, 2013.
International Search Report and Written Opinion in International Application No. PCT/US2013/033400, dated Jun. 28, 2013.
International Search Report and Written Opinion in International Application No. PCT/US2013/033403 dated Jun. 28, 2013.
International Search Report and Written Opinion in PCT/US2014/041766, dated Sep. 30, 2014.
International Search Report and Written Opinion dated Jun. 5, 2014 in International Application No. PCT/US2014/021677.
International Search Report and Written Opinion dated Jun. 6, 2014 in International Application No. PCT/US2014/023043.
International Search Report and Written Opinion dated Dec. 16, 2014, for International Application No. PCT/US2014/051011.
International Search Report and Written Opinion dated Jun. 19, 2015, in International Application No. PCT/US2015/020287.
Inui et al. "Molecular dynamics simulations of nanopore processing in a graphene sheet by using gas cluster ion beam." Applied Physics A: Materials Science & Processing 98.4 (2010): 787-794.
Israelachvili, "Intermolecular and Surface Forces," 3rd ed., Chap. 7.1, Sizes of Atoms, Molecules, and Ions, 2011, 1 page.
Jiao et al., "Castration differentially alters basal and leucine-stimulated tissue protein synthesis in skeletal muscle and adipose tissue," Am. J. Physiol. Endocrinol. Metab. 297(5): E1222-1232 (Nov. 2009) (available online Sep. 15, 2009).
JP Office Action in Japanese Application No. 2015-501729 dated Dec. 9, 2016 (English translation).
JP Office Action in Japanese Application No. 2015-501867 dated Oct. 11, 2016 (English translation).
JP Office Action in Japanese Application No. 2015-503405 dated Nov. 14, 2016 (English translation).
JP Office Action in Japanese Application No. 2015-503406 dated Dec. 6, 2016(English translation).
Kang et al., "Effect of eplerenone, enalapril and their combination treatment on diabetic nephropathy in type II diabetic rats," Nephrol. Dialysis Transplant. 24(1): 73-84 (Jan. 2009).
Kang et al., "Efficient Transfer of Large-Area Graphene Films onto Rigid Substrates by Hot Pressing," American Chemical Society Nano, 6(6): 5360-5365(May 28, 2012).
Kar et al., "Effect of glycation of hemoglobin on its interaction with trifluoperazine," Protein J. 25(3): 202-211 (Apr. 2006) (available online Jun. 6, 2006).
Kawamoto et al., "Serum high molecular weight adiponectin is associated with mild renal dysfunction in Japanese adults," J. Atherosclerosis Thrombosis 17(11): 1141-1148 (Nov. 27, 2011).
Khun et al. "From Microporous Regular Frameworks to Mesoporous Materials with Ultrahigh Surface Area: Dynamic reorganization of Porous Polymer Networks" JACS, 2008; vol. 130; pp. 13333-13337.
Krupka et al., "Measurements of the Sheet Resistance and Conductivity of Thin Epitaxial Graphene and SiC Films" Applied Physics Letters 96, 082101-I; Feb. 23, 2010.
Kumar et al., "Modulation of alpha-crystallin chaperone activity in diabetic rat lens by curcumin," Molecular Vision 11: 561-568 (Jul. 26, 2005).
Lathuiliere et al., "Encapsulated Cellular Implants for Recombinant Protein Delivery and Therapeutic Modulation of the Immune System," Journal of Applied Physics, Int. J. Mol. Sci., 16: 10578-10600 (May 8, 2015).
Lee, et al. "Measurement of the elastic properties and intrinsic strength of monolayer graphene." science 321.5887 (2008): 385-388.
Lucchese et al. "Quantifying ion-induced defects and Raman relaxation length in graphene." Carbon 48.5 (2010): 1592-1597.
MacLeod et al. "Supramolecular Orderinng in Oligothiophene-Fullerene Monolayers" JACS, 2009, vol. 131, pp. 16844-16850.
Mattevi et al. "A review of chemical vapour deposition of graphene on copper." Journal of Materials Chemistry 21.10 (2011): 3324-3334.
Miao et al. "Chemical vapor deposition of grapheme" INTECH Open Access Publisher, 2011.
MIT/MTL Center for Graphene Devices and 2D Systems, retrieved from: http://www-mtl.mit.edu/wpmu/graphene/ [retrieved from Aug. 21, 2014 archive] (3 pages).
MIT/MTL Center for Graphene Devices and 2D Systems, retrieved from: http://www-mtl.mit.edu/wpmu/graphene/ [retrieved from Mar. 4, 2015 archive] (3 pages).
Myunwoong Kim, et al, Fabrication and characterization of Large-Area, Semiconducting Nanoperforated Graphene Materials,American Chemical Society vol. 10, 1125-1131 (2010).
Nafea, et al. "Immunoisolating semi-permeable membranes for cell encapsulation: focus on hydrogels." J Control Release. 154(2): 110-122 (Sep. 5, 2011).
Nezlin, "Circulating non-immune IgG complexes in health and disease," Immunol. Lett. 122(2); 141-144 (Feb. 21, 2009) (available online Feb. 2, 2009).

(56) References Cited

OTHER PUBLICATIONS

Norata et al., "Plasma adiponectin levels in chronic kidney disease patients: relation with molecular inflammatory profile and metabolic status," Nutr. Metab. Cardiovasc. Dis. 20(1): 56-63 (Jan. 2010) (available online Apr. 9, 2009).
Ogawa et al., "Exosome-like vesicles in Gloydius blomhoffii blomhoffii venom," Toxicon 51(6): 984-993 (May 2008) (available online Feb. 19, 2008).
Ohgawara et al. "Assessment of pore size of semipermeable membrane for immunoisolation on xenoimplatntation of pancreatic B cells using a diffusion chamber." Transplant Proc. (6): 3319-3320. 1995.
Oki et al., "Combined acromegaly and subclinical Cushing disease related to high-molecular-weight adrenocorticotropic hormone," J. Neurosurg. 110(2): 369-73 (Feb. 2009).
Osorio et al., "Effect of treatment with losartan on salt sensitivity and SGLT2 expression in hypertensive diabetic rats," Diabetes Res. Clin. Pract. 86(3): e46-e49 (Dec. 2009) (available online Oct. 2, 2009).
Osorio et al., "Effect of phlorizin on SGLT2 expression in the kidney of diabetic rats," J. Nephrol. 23(5): 541-546 (Sep.-Oct. 2010).
Padidela et al., "Elevated basal and post-feed glucagon-like peptide 1 (GLP-1) concentrations in the neonatal period," Eur. J. Endocrinol. 160(1): 53-58 (Jan. 2009) (available online Oct. 24, 2008).
Pall Corporation, "Pall Water Processing Disc-Tube Filter Technology", Retrieved on Feb. 10, 2015, Retrieved from http://www.pall.com/pdfs/Fuels-and-Chemicals/Disc-Tube_FilterTechnology-DT100b.pdF (15 Pages).
Plant et al. "Size-dependent propagation of Au nanoclusters through few-layer grapheme," The Royal Society of Chemistry 2013, Nanoscale.
Pollard, "Growing Graphene via Chemical Vapor" Department of Physics, Pomona College; May 2, 2011.
Rafael et al. "Cell Transplantation and Immunoisolation: Studies on a macroencapsultaion device." From the Departments of Transplantation Pathology: Stockholm, Sweden (1999).
Rezania et al., "Enrichment of Human Embryonic Stem Cell-Derived NKX6.1-Expressing Pancreatic Progenitor Cells Accelerates the Maturation of Insulin-Secreting Cells In Vivo", Stem Cells Regenerative Medicine, vol. 31: 2432-2442 (Jul. 29, 2013).
Rezania et al., "Maturation of Human Embryonic Stem Cell-Derived Pancreatic Progenitors Into Functional Islets Capable of Treating Pre-existing Diabetes in Mice", Diabetes Journal, vol. 61: 2016-2029 (Aug. 1, 2012).
Ribeiro et al., "Binary Mutual Diffusion Coefficients of Aqueous Solutions of Sucrose, Lactose, Glucose, and Fructose in the Temperature Range from (298.15 to 328.15) K," J. Chem. Eng. Data 51(5): 1836-1840 (Sep. 2006) (available online Jul. 20, 2006).
Rippe et al., "Size and charge selectivity of the glomerular filter in early experimental diabetes in rats," Am. J. Physiol. Renal Physiol. 293(5): F1533-F1538 (Nov. 2007)(available online Aug. 15, 2007).
SA Final Rejection for Saudi Arabia Application No. 113340400 dated Jan. 28, 2016.
SA First Examination Report for Saudi Arabia Application No. 113340401 dated Apr. 28, 2015.
SA First Examination Report for Saudi Arabia Application No. 113340424 dated May 10, 2015.
SA First Examination Report for Saudi Arabia Application No. 113340426 dated May 12, 2015.
SA First Examination Report in Saudi Arabia Application No. 113340400 dated Apr. 13, 2015.
SA Second Examination Report for Saudi Arabia Application No. 113340400 dated Aug. 11, 2015.
Sanchez, et al. "Biological Interactions of Graphene-Family Nanomaterials—An Interdisciplinary Review." Chem Res Toxicol. 25(1): 15-34 (Jan. 13, 2012).
Sethna et al., "Serum adiponectin levels and ambulatory blood pressure monitoring in pediatric renal transplant recipients," Transplantation 88(8): 1030-1037 (Oct. 27, 2009).
Sullivan et al., "Microarray analysis reveals novel gene expression changes associated with erectile dysfunction in diabetic rats," Physiol. Genom. 23(2): 192-205 (Oct. 17, 2005) (available online Aug. 23, 2005).
Swett et al, "Imagining and Sculpting Graphene on the atomic scale" Oak Ridge National Laboratory's (ORNL) Center for Nanophase Materials Sciences (CNMS) Biannual Review. 1 page.
Swett et al, "Supersonic Nanoparticle Interaction with Suspended CVD Graphene", Microsc. Microanal. 22 (Suppl 3): 1670-1671 (Jul. 25, 2016).
Takata et al., "Hyperresistinemia is associated with coexistence of hypertension and type 2 diabetes," Hypertension 51. 2 (Feb. 2008): 534-9.
Tamborlane et al., "Continuous Glucose Monitoring and Intensive Treatment of Type 1 Diabetes" N Engl J Med 359;14: 1464-1476 (Oct. 2, 2008).
Tanugi et al., "Nanoporous Graphene Could Outperform Best Commercial Water Desalination Techniques," ; ACS 2012; Jun. 25, 2012; Weftec 2012; Sep. 29-Oct. 3.
Totani et al. "Gluten binds cytotoxic compounds generated in heated frying oil." Journal of oleo science 57.12 (2008): 683-690.
Tsukamoto et al. "Purification, characterization and biological activities of a garlic oliqosaccharide," Journal of UOEH 30.2 (Jun. 1, 2008): 147-57.
TW Office Action in Taiwanese Application No. 102146079 dated Apr. 14, 2017. 9 Pages.(English translation).
TW Search Report in Taiwanese Application No. 102146079 dated Apr. 14, 2017. 1 page.
Umea Universitet "Graphene nanoscrolls are formed by decoration of magnetic nanoparticles." ScienceDaily. Aug. 15, 2013. https://www.sciencedaily.com/releases/2013/08/130815084402.htm (3 pages).
U.S. Notice of Allowance for U.S. Appl. No. 12/868,150 dated Sep. 25, 2012.
U.S. Notice of Allowance for U.S. Appl. No. 13/548,539 dated Aug. 18, 2015.
U.S. Notice of Allowance for U.S. Appl. No. 13/548,539 dated Jul. 23, 2015.
U.S. Notice of Allowance for U.S. Appl. No. 13/719,579 dated May 20 ,2016.
U.S. Notice of Allowance for U.S. Appl. No. 13/795,276 dated Oct. 7, 2016.
U.S. Notice of Allowance for U.S. Appl. No. 13/802,896 dated Apr. 1, 2015.
U.S. Notice of Allowance for U.S. Appl. No. 13/803,958 dated Aug. 29, 2016.
U.S. Notice of Allowance for U.S. Appl. No. 13/803,958 dated Jun. 2, 2016.
U.S. Notice of Allowance for U.S. Appl. No. 13/803,958 dated Sep. 12, 2016.
U.S. Notice of Allowance for U.S. Appl. No. 13/804,085 dated Jan. 15, 2015.
U.S. Notice of Allowance for U.S. Appl. No. 13/804,085 dated Mar. 12, 2015.
U.S. Notice of Allowance for U.S. Appl. No. 13/923,503 dated Oct. 14, 2016.
U.S. Notice of Allowance for U.S. Appl. No. 13/923,503 dated Oct. 5, 2016.
U.S. Notice of Allowance for U.S. Appl. No. 14/200,195 dated Jul. 5, 2016.
U.S. Notice of Allowance for U.S. Appl. No. 14/200,530 dated Aug. 1, 2016.
U.S. Notice of Allowance for U.S. Appl. No. 14/203,655 dated Dec. 9, 2016.
U.S. Notice of Allowance in U.S. Appl. No. 12/868,150 dated Sep. 25, 2012.
U.S. Notice of Allowance in U.S. Appl. No. 13/795,276 dated Jan. 19, 2017.
U.S. Notice of Allowance in U.S. Appl. No. 13/803,958 dated Aug. 29, 2016.
U.S. Notice of Allowance in U.S. Appl. No. 13/803,958 dated Sep. 12, 2016.
U.S. Notice of Allowance in U.S. Appl. No. 14/610,770 dated May 5, 2017.

(56) References Cited

OTHER PUBLICATIONS

U.S. Notice of Allowance in U.S. Appl. No. 14/656,580 dated May 8, 2017.
U.S. Notice of Allowance in U.S. Appl. No. 14/819,273 dated Jun. 9, 2017.
U.S. Notice of Allowance in U.S. Appl. No. 15/099,464 dated Jun. 16, 2017.
U.S. Office Action for U.S. Appl. No. 13/548,539 dated Feb. 6, 2015.
U.S. Office Action for U.S. Appl. No. 13/719,579 dated Jul. 8, 2015.
U.S. Office Action for U.S. Appl. No. 13/719,579 dated May 4, 2016.
U.S. Office Action for U.S. Appl. No. 13/795,276 dated Apr. 22, 2016.
U.S. Office Action for U.S. Appl. No. 13/795,276 dated Oct. 6, 2015.
U.S. Office Action for U.S. Appl. No. 13/802,896 dated Sep. 24, 2014.
U.S. Office Action for U.S. Appl. No. 13/803,958 dated Aug. 11, 2014.
U.S. Office Action for U.S. Appl. No. 13/803,958 dated May 28, 2015.
U.S. Office Action for U.S. Appl. No. 13/803,958 dated Nov. 18, 2015.
U.S. Office Action for U.S. Appl. No. 13/923,503 dated Mar. 22, 2016.
U.S. Office Action for U.S. Appl. No. 14/031,300 dated Jan. 20, 2016.
U.S. Office Action for U.S. Appl. No. 14/031,300 dated Jul. 7, 2015.
U.S. Office Action for U.S. Appl. No. 14/200,195 dated Mar. 21, 2016.
U.S. Office Action for U.S. Appl. No. 14/200,195 dated Nov. 4, 2015.
U.S. Office Action for U.S. Appl. No. 14/200,530 dated Feb. 29, 2016.
U.S. Office Action for U.S. Appl. No. 14/203,655 dated Aug. 10, 2016.
U.S. Office Action for U.S. Appl. No. 14/656,190 dated May 18, 2017.
U.S. Office Action for U.S. Appl. No. 14/686,452 dated Jun. 9, 2017.
U.S. Office Action for U.S. Appl. No. 14/856,471 dated May 31, 2017.
U.S. Office Action for U.S. Appl. No. 14/858,741 dated Dec. 1, 2016.
U.S. Office Action for U.S. Appl. No. 15/289,944 dated Feb. 9, 2017.
U.S. Office Action for U.S. Appl. No. 15/336,545 dated Dec. 19, 2016.
U.S. Office Action for U.S. Appl. No. 15/453,441 dated Jun. 5, 2017.
U.S. Office Action in U.S. Appl. No. 14/193,007 dated Apr. 24, 2017.
U.S. Office Action in U.S. Appl. No. 14/656,617 dated Apr. 4, 2017.
U.S. Office Action in U.S. Appl. No. 14/193,007 dated Jul. 1, 2016.
U.S. Office Action on U.S. Appl. No. 14/656,335 dated Apr., 25 2017.
U.S. Office Action on U.S. Appl. No. 15/332,982 dated Jan. 30, 2017.
U.S. Supplemental Notice of Allowance for U.S. Appl. No. 13/795,276 dated Nov. 29, 2016.
Vallon, "Micropuncturing the nephron," Pflugers Archiv : European journal of physiology 458. 1 (May 2009): 189-201.
Van Der Zande et al. "Large-scale arrays of single-layer graphene resonators." Nano letters 10.12 (2010): 4869-4873.
Verdonck, P., "Plasma Etching", in Oficina de Microfabricao: Projeto e Construcao de CI's MOS, Swart, J.W., Ed., Campinas (Sao Paulo, Brazil): UNICAMP, 2006, ch. 10, p. 9.
Vlassiouk et al. "Large scale atmospheric pressure chemical vapor deposition of graphene." Carbon 54 (2013): 58-67.
Vriens et al. "Methodological considerations in quantification of oncological FDG PET studies." European journal of nuclear medicine and molecular imaging 37.7 (2010): 1408-1425.
Wang et al., "Direct Observation of a Long-Lived Single-Atom Catalyst Chiseling Atomic Structures in Graphene," Nano Lett., 2014, pp. A-F.
Wang et al., "Porous Nanocarbons: Molecular Filtration and Electronics," Advances in Graphene Science, Edited by Mahmood Aliofkhazraei, (2013) ISBN 978-953-51-1182-5, Publisher: InTech; Chapter 6, pp. 119-160.
Wang et al.,"What is the role of the second "structural " NADP+-binding site in human glucose 6-phosphate dehydrogenase? ,"Protein science a publication of the Protein Society 17.8 (Aug. 2008): 1403-11.
Wei et al., "Synthesis of N-doped graphene by chemical vapor deposition and its electrical properties", Nano Lett. 2009 9 1752-58.
Xiaogan Liang et al., Formation of Bandgap and Subbands in Graphene Nanomeshes with Sub-10nm Ribbon Width Fabricated via Nanoimprint Lithography., Nano Letters, Jun. 11, 2010, pp. 2454-2460.
Xie et al., "Fractionation and characterization of biologically-active polysaccharides from Artemisia tripartite," Phytochemistry 69. 6 (Apr. 2008): 1359-71.
Xie, et al. "Controlled fabrication of high-quality carbon nanoscrolls from monolayer graphene." Nano letters 9.7 (2009): 2565-2570.
Yagil et al. "Nonproteinuric diabetes-associated nephropathy in the Cohen rat model of type 2 diabetes" Diabetes 54. 5 (May 2005): 1487-96.
Zan et al. "Interaction of Metals with Suspended Graphene Observed by Transmission Electron Microscopy", J. Phys. Chem. Lett., Mar. 8, 2012, 3, 953-958.
Zhang et al. "Effect of Chemical Oxidation on the Structure of Single-Walled Carbon Nanotubes", J. Phys. Chem., Feb. 12, 2003, B 107 3712-8.
Zhang et al. "Method for anisotropic etching of graphite or graphene" Institute of Physics, Chinese Academy of Sciences; PEOP. Rep. China; Mar. 30, 2011.
Zhang et al. "Production of Graphene Sheets by Direct Dispersion with Aromatic Healing Agents", Small, May 6, 2010, vol. 6, No. 10, 1100-1107.
Zhang et al. "Isolation and activity of an alpha-amylase inhibitor from white kidney beans," Yao xue xue bao=Acta pharmaceutica Sinica 42. 12 (Dec. 2007): 1282-7.
Zhao, et al. "Efficient preparation of large-area graphene oxide sheets for transparent conductive films." ACS nano 4.9 (2010): 5245-5252.
Zhou, K., et al., "One-pot preparation of graphene/ Fe3O4 composites by a solvothermal reaction," New J. Chem., 2010, 34, 2950.
Zhu et al. "Carbon Nanotubes in Biomedicine and Biosensing", Carbon Nanotubes-Growth and Applications, InTech, (Aug. 9, 2011) Chapter 6: pp. 135-162. Available from: https://www.intechopen.com/books/carbon-nanotubes-growth-and-applications/carbon-nanotubes-in-biomedicine-and-biosensing.
Ziegelmeier et al. "Adipokines influencing metabolic and cardiovascular disease are differentially regulated in maintenance hemodialysis," Metabolism: clinical and experimental 57. 10 (Oct. 2008): 1414-21.
Zirk et al. "A refractometry-based glucose analysis of body fluids," Medical engineering & physics 29. 4 (May 2007): 449-58.
Zyga "Nanoporous Graphene Could Outperform Best Commercial Water Desalination Techniques," Phys.org., Jun. 22, 2012, Retrieved from http://www.phys.org/pdf259579929.pdf [Last Accessed Dec. 3, 2014] (3 pages).
International Search Report and Written Opinion dated Jul. 5, 2017 from related PCT application PCT/US2017/024147.
U.S. Office Action for U.S. Appl. No. 14/843,944 dated Jun. 23, 2017.
EPO Extended Search Report for European Application No. 171684883.5 dated Jul. 25, 2017 (8 pages).
EPO Supplementary Search Report for European Application No. 15762019.6 dated Aug. 9, 2017 (16 pages).
U.S. Notice of Allowance in U.S. Appl. No. 14/610,770 dated Sep. 26, 2017. (12 pages).

(56) References Cited

OTHER PUBLICATIONS

U.S. Notice of Allowance in U.S. Appl. No. 15/332,982 dated Sep. 21, 2017. (5 pages).
U.S. Office Action in U.S. Appl. No. 15/099,099 dated Oct. 5, 2017 (11 pages).
U.S. Office Action in U.S. Appl. No. 15/099,447 dated Oct. 3, 2017 (21 pages).
Weisen, et al., "Fabrication of nanopores in a graphene sheet with heavy ions: A molecular dynamics study", Journal of Applied Physics 114, 234304 (2013), pp. 234304-1 to 234304-6.
U.S. Notice of Allowance in U.S. Appl. No. 14/610,770 dated Jan. 23, 2017.
U.S. Notice of Allowance in U.S. Appl. No. 14/856,198 dated Feb. 10, 2017.
U.S. Notice of Allowance in U.S. Appl. No. 14/856,198 dated Mar. 01, 2017.
U.S. Office Action in U.S. Appl. No. 14/609,325 dated Feb. 16, 2017.
U.S. Office Action in U.S. Appl. No. 14/193,007 dated Mar. 23, 2017.
U.S. Office Action in U.S. Appl. No. 14/656,580 dated Feb. 9, 2017.
U.S. Office Action in U.S. Appl. No. 14/843,944 dated Jan. 6, 2017.
U.S. Office Action in U.S. Appl. No. 15/099,464 dated Mar. 10, 2017.
Australian Office Action in Application No. 2013235234 dated Dec. 19, 2017 (5 pages).
Japanese Office Action in Application No. 2017-002652 dated Nov. 24, 2017 (with English translation) (7 pages).
Chu, L., et al., "Porous graphene sandwich/poly(vinylidene fluoride) composites with high dielectric properties," Composites Science and Technology, 86, (2013), pp. 70-75.
European Extended Search Report in Application No. 15743307.9 dated Nov. 15, 2017 (14 pages).
European Extended Search Report in Application No. 15755350.4 dated Oct. 30, 2017 (9 pages).
European Extended Search Report in Application No. 15762019.6 dated Nov. 20, 2017 (12 pages).
European Extended Search Report in Application No. 15762213.5 dated Oct. 10, 2017 (8 pages).
Gu et al., "One-step synthesis of porous graphene-based hydrogels containing oil droplets for drug delivery", Royal Society of Chemistry (RSC), vol. 4, No. 7, Jan. 1, 2014, pp. 3211-3218.
Japanese Office Action in Application No. 2015-549508 dated Nov. 7, 2017 (with English translation) (2 pages).
Kim et al., "Selective Gas Transport Through Few-Layered Graphene and Graphene Oxide Membranes", Science, vol. 342, Oct. 4, 2013, pp. 91-95 (6 total pages).
Singapore Search Report and Written Opinion in Application No. 11201609272T dated Oct. 5, 2017 (11 pages).
U.S. Notice of Allowance in U.S. Appl. No. 15/099,464 dated Nov. 16, 2017 (5 pages).
U.S. Notice of Allowance in U.S. Appl. No. 15/332,982 dated Nov. 1, 2017 (9 pages).
U.S. Office Action in U.S. Appl. No. 14/707,808 dated Nov. 6, 2017 (27 pages).
U.S. Office Action in U.S. Appl. No. 15/099,193 dated Dec. 28, 2017 (25 pages).
Wang, M., et al., "Interleaved Porous Laminate Composed of Reduced Graphene Oxide Sheets and Carbon Black Spacers by In-Situ Electrophoretic Deposition," The Royal Society of Chemistry (2014), pp. 1-3.
Wimalasiri, Y., et al., "Carbon nanotube/graphene composite for enhanced capacitive deionization performance," Carbon 59 (2013), pp. 464-471.
U.S. Appl. No. 14/858,741, filed Sep. 18, 2015.
U.S. Appl. No. 15/308,351, filed Nov. 1, 2016.
U.S. Appl. No. 15/336,545, filed Oct. 27, 2016.
U.S. Appl. No. 15/289,944, filed Oct. 10, 2016.
U.S. Pat. No. 9,193,587 U.S. Appl. No. 13/548,539, Nov. 24, 2015 filed Jul. 13, 2012.
U.S. Appl. No. 13/422,753, filed Mar. 16, 2012.
U.S. Pat. No. 8,361,321 U.S. Appl. No. 12/868,150, Jan. 29, 2013 filed Aug. 25, 2010.
U.S. Pat. No. 9,475,709 U.S. Appl. No. 13/719,579, Oct. 25, 2016 filed Dec. 19, 2012.
U.S. Pat. No. 9,028,663 U.S. Appl. No. 13/804,085, May 12, 2015 filed Mar. 14, 2013.
U.S. Appl. No. 14/686,452, filed Apr. 14, 2015.
U.S. Pat. No. 9,463,421 U.S. Appl. No. 13/803,958, Oct. 11, 2016 filed Mar. 14, 2013.
U.S. Pat. No. 9,095,823 U.S. Appl. No. 13/802,896, Aug. 4, 2015 filed Mar. 14, 2013.
U.S. Pat. No. 9,592,475 U.S. Appl. No. 14/203,655, Mar. 14, 2017 filed Mar. 11, 2014.
U.S. Pat. No. 9,480,952 U.S. Appl. No. 14/200,195, Nov. 1, 2016 filed Mar. 7, 2014.
U.S. Pat. No. 9,567,224 U.S. Appl. No. 13/795,276, Feb. 14, 2017 filed Mar. 12, 2013.
U.S. Appl. No. 14/031,300, filed Sep. 19, 2013.
U.S. Pat. No. 9,505,192 U.S. Appl. No. 14/200,530, Nov. 29, 2016 filed Mar. 7, 2014.
U.S. Pat. No. 9,572,918 U.S. Appl. No. 13/923,503, Feb. 21, 2017 filed Jun. 21, 2013.
U.S. Appl. No. 13/779,963, filed Feb. 28, 2013.
U.S. Pat. No. 9,610,546 U.S. Appl. No. 14/856,198, Apr. 4, 2017 filed Sep. 16, 2015.
U.S. Appl. No. 14/656,335, filed Mar. 12, 2015.
U.S. Appl. No. 14/656,617, filed Mar. 12, 2015.
U.S. Pat. No. 9,242,865 U.S. Appl. No. 14/192,796, Jan. 26, 2016 filed Feb. 27, 2014.
U.S. Appl. No. 15/589,135, filed May 8, 2017.
U.S. Appl. No. 15/332,982, filed Oct. 24, 2016.
U.S. Appl. No. 15/410,457, filed Jan. 19, 2017.
U.S. Appl. No. 15/453,441, filed Mar. 8, 2017.
U.S. Appl. No. 14/971,922, filed Dec. 16, 2015.
U.S. Pat. No. 9,169,575 U.S. Appl. No. 14/195,802, Oct. 27, 2015 filed Mar. 3, 2014.
Office Action for Indian Appl. Ser. No. 1566/DELNP/2013 dated Feb. 2, 2018 (7 pages).
Office Action for Japanese Appl. Ser. No. 2016-521448 dated Mar. 16, 2018 (5 pages).
Skrzypek et al., "Pancreatic islet macroencapsulation using microwell porous membranes", Scientific Reports, 7: 9186 | DOI:10.1038/s41598-017-09647-7, Aug. 23, 2017 (12 pages).
U.S. Notice of Allowance for U.S. Appl. No. 15/099,464 dated Feb. 28, 2018 (5 pages).
U.S. Office Action for U.S. Appl. No. 15/099,276 dated Mar. 22, 2018 (13 pages).
U.S. Office Action for U.S. Appl. No. 15/453,441 dated Mar. 22, 2018 (7 pages).
European Extended Search Report in Application No. 15837617.8 dated Mar. 22, 2018 (9 pages).
Singapore Written Opinion for Appl. Ser. No. 11201607584P dated Jun. 8, 2018 (7 pages).
U.S. Non-Final Office Action for U.S. Appl. No. 15/099,410 dated Jun. 13, 2018 (15 pages).
U.S. Notice of Allowance for U.S. Appl. No. 15/453,441 dated Jun. 12, 2018 (8 pages).
U.S. Office Action for U.S. Appl. No. 15/099,056 dated May 29, 2018 (33 pages).
U.S. Office Action for U.S. Appl. No. 15/099,289 dated Jun. 7, 2018 (16 pages).
Bose et al.,"Microfabricated immune-isolating devices for transplanting therapeutic cells in vivo", Koch Institute of Integrative Cancer Research, Massachusetts Institute of Technology, Undated (1 page).
Indian Office Action for Appl. Ser. No. 7731/DELNP/2014 dated Jul. 26, 2018 (6 pages).
Japanese Office Action for Appl. Ser. No. 2017-002652 dated Jul. 3, 2018 (8 pages).
Linnert, "Welding Metallurgy—Carbon and Alloy Steels", vol. I—Fundamentals (4th Edition), Chapter 2—The Structure of Metals, GML Publications, American Welding Society (AWS), Year:

(56) References Cited

OTHER PUBLICATIONS 1994, pp. 17-74. Retrieved from app.knovel.com/hotlink/pdf/id:kt0095RCL3/welding-metallurgy-carbon/structure-metals.
U.S. Final Office Action for U.S. Appl. No. 14/707,808 dated Jun. 27, 2018 (28 pages).
U.S. Final Office Action for U.S. Appl. No. 15/099,482 dated Aug. 27, 2018 (10 pages).
U.S. Non-Final Office Action for U.S. Appl. No. 15/099,239 dated Jul. 12, 2018 (31 pages).
U.S. Notice of Allowance for U.S. Appl. No. 15/099,420 dated Aug. 8, 2018 (8 pages).
Vatanpour et al., "Fabrication and characterization of novel antifouling nanofiltration membrane prepared from oxidized multiwalled carbon nanotube/polyethersulfone nanocomposite", Journal of Membrane Science, vol. 375, Elsevier, Apr. 6, 2011, pp. 284-294.
Zhang et al., "Synergetic effects of oxidized carbon nanotubes and graphene oxide on fouling control and anti-fouling mechanism of polyvinylidene fluoride ultrafiltration membranes", Journal of Membrane Science, vol. 448, Elsevier, Aug. 7, 2013, pp. 81-92.
Canadian Office Action for Appl. Ser. No. 2,865,648 dated Jan. 16, 2019 (4 pages).
EPO Office Action for Appl. Ser. No. 13714806.0 dated Dec. 5, 2018 (6 pages).
EPO Office Action for Appl. Ser. No. 15786691.4 dated Dec. 5, 2018 (6 pages).
Extended European Search Report for Appl. Ser. No. 16833431.6 dated Feb. 25, 2019 (16 pages).
Koenig et al., "Selective Molecular Sieving Through Porous Graphene", Nature Nanotechnology, vol. 7, No. 11, pp. 728-732 (Including Supplementary Informaton) (23 pages).
U.S. Advisory Action for U.S. Appl. No. 15/099,289 dated Jan. 8, 2019 (6 pages).
U.S. Final Office Action for U.S. Appl. No. 14/686,452 dated Dec. 13, 2018 (6 pages).
U.S. Final Office Action for U.S. Appl. No. 15/099,099 dated Jan. 2, 2019 (13 pages).
U.S. Final Office Action for U.S. Appl. No. 15/099,239 dated Feb. 21, 2019 (26 pages).
U.S. Non-Final Office Action for U.S. Appl. No. 14/609,325 dated Jan. 14, 2019 (7 pages).
U.S. Non-Final Office Action for U.S. Appl. No. 15/099,482 dated Jan. 31, 2019 (13 pages).
U.S. Notice of Allowance for U.S. Appl. No. 15/099,289 dated Jan. 18, 2019 (7 pages).
U.S. Notice of Allowance for U.S. Appl. No. 15/099,410 dated Jan. 3, 2019 (9 pages).
U.S. Final Office Action for U.S. Appl. No. 14/609,325 dated Sep. 12, 2018 (8 pages).
U.S. Final Office Action for U.S. Appl. No. 15/099,289 dated Oct. 15, 2018 (14 pages).
U.S. Non-Final Office Action for U.S. Appl. No. 14/656,657 dated Oct. 10, 2018 (6 pages).
U.S. Non-Final Office Action for U.S. Appl. No. 14/707,808 dated Nov. 15, 2018 (34 pages).
U.S. Non-Final Office Action for U.S. Appl. No. 15/099,099 dated Sep. 27, 2018 (13 pages).
U.S. Non-Final Office Action for U.S. Appl. No. 15/099,269 dated Oct. 5, 2018 (11 pages).
U.S. Non-Final Office Action for U.S. Appl. No. 15/099,276 dated Nov. 1, 2018 (13 pages).
U.S. Notice of Allowance for U.S. Appl. No. 15/099,056 dated Nov. 16, 2018 (8 pages).
Extended European Search Report for Appl. Ser. No. 16833429.0 dated Aug. 9, 2019 (14 pages).
Farah et al., "Long-Term Implant Fibrosis Prevention in Rodents and Non-Human Primates Using Crystallized Drug Formulations", Nature Materials, vol. 18, Aug. 2019, pp. 892-904.
Japanese Office Action for Appl. Ser. No. 2017-511982 dated Jul. 9, 2019 (6 pages).
Raimondo et al., "Functional muscle recovery with nanoparticle-directed M2 macrophage polarization in mice", Proceedings of the National Academy of Sciences of the United States of America (PNAS), Sep. 4, 2018, pp. 1-6.
University of Massachusetts Medical School, "Fibrosis Mitigation Pathway", PowerPoint Presentation, date of presentation unknown (6 pages).
U.S. Non-Final Office Action for U.S. Appl. No. 15/589,135 dated Aug. 1, 2019 (11 pages).
U.S. Notice of Allowance for U.S. Appl. No. 14/609,325 dated Jul. 30, 2019 (7 pages).
U.S. Notice of Allowance for U.S. Appl. No. 15/410,457 dated Aug. 14, 2019 (8 pages).
Yang et al., "Large-area graphene-nanomesh/carbon-nanotube hybrid membranes for ionic and molecular nanofiltration", Science, vol. 364, Jun. 14, 2019, pp. 1057-1062 (7 pages).
Zhang et al., "Rapid and Long-Term Glycemic Regulation with a Balanced Charged Immune-Evasive Hydrogel in T1DM Mice", Advanced Functional Materials, Advanced Science News, Jan. 30, 2019, pp. 1-9.
Zhang et al., "Rapid and Long-Term Glycemic Regulation with a Balanced Charged Immune-Evasive Hydrogel in T1DM Mice", Advanced Functional Materials, Advanced Science News, Jan. 30, 2019, Supporting Information (13 pages).
U.S. Appl. No. 61/452,704, filed Mar. 15, 2011, Russo et al.
Apel et al. "Effect of nanosized surfactant molecules on the etching oF ion tracks: New degrees or freedom in design of pore shape", Nuclear Instruments and Methods in Physics Research Section B: Beam Interactions with Materials and Atoms, vol. 209, Aug. 2003, pp. 329-334.
Australian Office Action for Appl. Ser. No. 2015252784 dated Mar. 25, 2019 (11 pages).
Australian Office Action for Appl. Ser. No. 2015255756 dated Feb. 22, 2019 (5 pages).
Extended European Search Report for Appl. Ser. No. 16833430.8 dated Apr. 25, 2019 (11 pages).
Extended European Search Report for Appl. Ser. No. 16833432.4 dated Apr. 16, 2019 (14 pages).
Extended European Search Report for Appl. Ser. No. 16833433.2 dated Mar. 4, 2019 (15 pages).
International Search Report and Written Opinion for PCT Appl. Ser. No. PCT/US2018/065514 (16 pages).
Japanese Office Action for Appl. Ser. No. 2016-565216 dated Feb. 26, 2019 (7 pages).
Kim et al., "High quality reduced graphene oxide through repairing with multi-layered graphene ball nanostructures", Scientific Reports, vol. 3, No. 1, Nov. 19, 2013, pp. 1-6.
Singapore Written Opinion for Appl. Ser. No. 11201800845X dated Feb. 26, 2019 (8 pages).
Singapore Written Opinion for Appl. Ser. No. 11201800883R dated Feb. 22, 2019 (7 pages).
Singapore Written Opinion for Appl. Ser. No. 11201800968Q dated Feb. 19, 2019 (6 pages).
U.S. Final Office Action for U.S. Appl. No. 15/099,269 dated Apr. 18, 2019 (7 pages).
U.S. Non-Final Office Action for U.S. Appl. No. 14/656,657 dated Mar. 28, 2019 (9 pages).
U.S. Non-Final Office Action for U.S. Appl. No. 14/686,452 dated May 3, 2019 (7 pages).
U.S. Non-Final Office Action for U.S. Appl. No. 15/099,193 dated May 2, 2019 (19 pages).
U.S. Non-Final Office Action for U.S. Appl. No. 15/410,457 dated Feb. 28, 2019 (13 pages).
CN Office Action in Chinese Application No. 201580006829.5 dated Aug. 1, 2017. (English translation) (8 pages).
EP Office Action for European Application No. 15743307.9 dated Aug. 8, 2017. (17 pages).
European Search Report dated Aug. 28, 2017 from related EP application 15743750.0. (7 pages).
International Search Report and Written Opinion dated Aug. 14, 2017 from related PCT application PCT/US2017/031537. (12 pages).

(56) References Cited

OTHER PUBLICATIONS

Jiang, L. et al., Design of advanced porous grapheme materials: from grapheme nanomesh to 3D architectures. Nanoscale, Oct. 16, 2013, vol. 6, pp. 1922-1945.
JP Office Action in Japanese Application No. 2015-503405 dated Jun. 28, 2017. (English translation) (6 pages).
JP Office Action in Japanese Application No. 2015-549508 dated Jun. 27, 2017. (English translation) (7 pages).
Li, R.H. "Materials for immunoisolated cell transplantation". Adv. Drug Deliv. Rev. 33, 87-109 (1998). (23 pages).
Schweitzer, Handbook of Separation Techniques for Chemical Engineers, 1979, McGraw-Hill Book Company, pp. 2-5 to 2-8.
Search Report and Written Opinion dated Aug. 14, 2017 for Singapore Application No. 11201606287V. (10 pages).
Search Report and Written Opinion dated Aug. 22, 2017 for Singapore Application No. 11201607584P. (7 pages).
Sears et al., "Recent Developments in Carbon Nanotube Membranes for Water Purification and Gas Separation" Materials, vol. 3 (Jan. 4, 2010), pp. 127-149.
U.S. Notice of Allowance in U.S. Appl. No. 14/193,007 dated Sep. 6, 2017. (9 pages).
U.S. Notice of Allowance in U.S. Appl. No. 14/656,580 dated Sep. 5, 2017. (8 pages).
U.S. Office Action for U.S. Appl. No. 14/609,325 dated Aug. 25, 2017. (7 pages).
U.S. Office Action for U.S. Appl. No. 15/099,193 dated Jul. 19, 2017. (13 pages).
U.S. Office Action for U.S. Appl. No. 15/289,944 dated Jul. 13, 2017. (18 pages).
U.S. Office Action for U.S. Appl. No. 15/332,982 dated Aug. 18, 2017. (9 pages).
Allen et al., "Craters on silicon surfaces created by gas cluster ion impacts," Journal of Applied Physics, 92(7): 3671-3678 (Oct. 2002).
Atmeh et al., "Albumin Aggregates: Hydrodynamic Shape and Physico-Chemical Properties," Jordan Journal of Chemistry, 2(2): 169-182 (2007).
Chen et al., "Mechanically Strong, Electrically Conductive, and Biocompatible Graphene Paper," Adv. Mater., 20(18): 3557-3561 (Sep. 2008) (available online Jul. 2008).
CN Office Action in Chinese Application No. 201380013988.9 dated Aug. 18, 2016 (English translation not readily available).
Fuertes, "Carbon composite membranes from Matrimid® and Kapton® polyimides for gas separation," Microporous and Mesoporous Materials, 33: 115-125 (1991).
Galashev, "Computer study of the removal of Cu from the graphene surface using Ar clusters," Computational Materials Science, 98: 123-128 (Feb. 2015) (available online Nov. 2014).
International Search Report and Written Opinion in PCT/US2015/013599 dated Jul. 20, 2015.
International Search Report and Written Opinion in PCT/US2015/013805 dated Apr. 30, 2015.
International Search Report and Written Opinion in PCT/US2015/018114 dated Jun. 3, 2015.
International Search Report and Written Opinion in PCT/US2015/020246 dated Jun. 10, 2015.
International Search Report and Written Opinion in PCT/US2015/020296 dated Jun. 17, 2015.
International Search Report and Written Opinion in PCT/US2015/028948 dated Jul. 16, 2015.
International Search Report and Written Opinion in PCT/US2015/029932 dated Oct. 6, 2015.
Inui et al., "Molecular dynamics simulations of nanopore processing in a graphene sheet by using gas cluster ion beam," Appl. Phys. A, 98: 787-794 (Mar. 2010) (available online Dec. 2009).
Koh et al., "Sensitive NMR Sensors Detect Antibodies to Influenza," NIH PA Author Manuscript PMC (Apr. 2009), also published in Angew. Chem. Int'l Engl, 47(22): 4119-4121 (May 2008) (available online Apr. 2008).
Lehtinen et al., "Cutting and controlled modification of graphene with ion beams," Nanotechnology, 22: 175306 (8 pages) (Mar. 2011).
Matteucci et al., "Transport of gases and Vapors in Glass and Rubbery Polymers," in Materials Science of Membranes for Gas and Vapor Separation. (Yampolskii et al., eds. 2006) (available online Jun. 2006).
O'Hern et al., "Development of process to transfer large areas of LPCVD graphene from copper foil to a porous support substrate," 1-62 (M.S. Thesis, Massachusetts Institute of Technology, Thesis) (Sep. 2011).
Plant et al. "Size-dependent propagation of Au nanoclusters through few-layer graphene," Nanoscale, 6: 1258-1263 (2014) (available online Oct. 2013).
Popok. "Cluster Ion Implantation in Graphite and Diamond: Radiation Damage and Stopping of Cluster Constituents," Reviews on Advanced Materials Science, 38(1): 7-16 (2014).
Russo et al., "Atom-by-atom nucleation and growth of graphene nanopores," PNAS 109(16): 5953-5957 (Apr. 2012).
U.S. Notice of Allowance in U.S. Appl. No. 14/610,770 dated Aug. 12, 2016.
U.S. Office Action in U.S. Appl. No. 14/656,190 dated Aug. 29, 2016.
U.S. Office Action for U.S. Appl. No. 14/656,580 dated Jun. 2, 2016.
U.S. Office Action in U.S. Appl. No. 14/819,273 dated Jul. 6, 2016.
U.S. Office Action for U.S. Appl. No. 14/856,198 dated Jun. 3, 2016.
Yoon, "Simulations show how to turn graphene's defects into assets," Sciencedaily (Oct. 4, 2016), www.sciencedaily.com/releases/2016/10/161004120428.htm.
Zabihi et al., "Formation of nanopore in a suspended graphene sheet with argon cluster bombardment: A molecular dynamics simulation study," Nuclear Instruments and Methods in Physics Research B, 343: 48-51: (Jan. 2015) (available online Nov. 2014).
Zhang et al. Modern Thin-Film Technology 284-285 (Metallurgical Industry Press, 1st ed. 2009) (English translation not readily available).
Zhao et al. (2012), "Effect of SiO2 substrate on the irradiation-assisted manipulation of supported graphene: a molecular dynamics study," Nanotechnology 23(28): 285703 (Jul. 2012) (available online Jun. 2012).
Zhao et al. (May 2012), "Drilling Nanopores in Graphene with Clusters: A Molecular Dynamics Study," J. Phys. Chem. C, 116(21): 11776-11178 (2012) (available online May 2012).
U.S. Appl. No. 14/193,007, filed Feb. 28, 2014.
U.S. Appl. No. 14/856,471, filed Sep. 16, 2015.
U.S. Appl. No. 15/099,295, filed Apr. 14, 2016.
U.S. Appl. No. 15/099,410, filed Apr. 14, 2016.
U.S. Appl. No. 15/099,420, filed Apr. 14, 2016.
U.S. Appl. No. 15/099,289, filed Apr. 14, 2016.
U.S. Appl. No. 15/099,447, filed Apr. 14, 2016.
U.S. Appl. No. 15/099,269, filed Apr. 14, 2016.
U.S. Appl. No. 15/099,239, filed Apr. 14, 2016.
U.S. Appl. No. 15/099,464, filed Apr. 14, 2016.
U.S. Appl. No. 15/099,276, filed Apr. 14, 2016.
U.S. Appl. No. 15/099,482, filed Apr. 14, 2016.
U.S. Appl. No. 15/099,056, filed Apr. 14, 2016.
U.S. Appl. No. 15/099,099, filed Apr. 14, 2016.
U.S. Appl. No. 14/656,190, filed Mar. 12, 2015.
U.S. Appl. No. 15/099,304, filed Apr. 14, 2016.
U.S. Appl. No. 15/099,588, filed Apr. 14, 2016.
U.S. Appl. No. 14/707,808, filed May 8, 2015.
U.S. Appl. No. 14/819,273, filed Aug. 5, 2015.
U.S. Appl. No. 14/856,198, filed Sep. 16, 2015.
U.S. Appl. No. 14/754,531, filed Jun. 29, 2015.
U.S. Appl. No. 14/610,770, filed Jan. 30, 2015.
U.S. Appl. No. 14/656,657, filed Mar. 12, 2015.
U.S. Appl. No. 14/609,325, filed Jan. 29, 2015.
U.S. Appl. No. 14/656,580, filed Mar. 12, 2015.
U.S. Appl. No. 13/480,569, filed May 25, 2012.
PCT/US2015/028948, May 1, 2015.
PCT/US2015/018114, Feb. 27, 2015.

(56) References Cited

OTHER PUBLICATIONS

U.S. Appl. No. 14/843,944, filed Sep. 2, 2015.
U.S. Appl. No. 15/099,193, filed Apr. 14, 2016.
Dong et al., "Growth of large-sized graphene thin-films by liquid precursor-based chemical vapor deposition under atmospheric pressure," Carbon 49(11): 3672-3678 (May 2011).
Hong et al., "Graphene multilayers as gates for multi-week sequential release of proteins from surfaces," NIH-PA Author Manuscript PMC (Jun. 1, 2014), also published in ACS Nano, Jan. 24, 2012; 6(1): 81-88 (first published online Dec. 29, 2011).
Hu et al., "Enabling graphene oxide nanosheets as water separation membranes," Environmental Science & Technology, 47(8): 3715-3723 (Mar. 14, 2013).
International Search Report and Written Opinion of the International Searching Authority dated Jul. 22, 2016, from related international patent application PCT/US2016/027607.
International Search Report and Written Opinion of the International Searching Authority dated Jul. 22, 2016, from related international patent application PCT/US2016/027616.
International Search Report and Written Opinion of the International Searching Authority dated Jul. 22, 2016, from related PCT application PCT/US2016/027596.
International Search Report and Written Opinion of the International Searching Authority dated Jul. 22, 2016, from related PCT application PCT/US2016/027603.
International Search Report and Written Opinion of the International Searching Authority dated Jul. 22, 2016, from related PCT application PCT/US2016/027610.
International Search Report and Written Opinion of the International Searching Authority dated Jul. 22, 2016, from related PCT application PCT/US2016/027612.
International Search Report and Written Opinion of the International Searching Authority dated Jun. 22, 2016, from related PCT application PCT/US2016/027637.
Kurapati et al., "Graphene oxide based multilayer capsules with unique permeability properties: facile encapsulation of multiple drugs," Chemical Communication 48: 6013-6015 (Apr. 25, 2012).
Li et al., "3D graphene oxide-polymer hydrogel: near-infrared light-triggered active scaffold for reversible cell capture and on-demand release," Advanced Materials 25: 6737-6743 (Oct. 7, 2013).
Marquardt et al., "Hybrid materials of platinum nanoparticles and thiol-functionalized graphene derivatives," Carbon 66: 285-294 (Jan. 2014; first published online Sep. 12, 2013).
Nam et al., "Monodispersed PtCo nanoparticles on hexadecyltrimethylammonium bromide treated graphene as an effective oxygen reduction reaction catalyst for proton exchange membrane fuel cells," Carbon 50: 3739-3747 (Aug. 2012; first published online Apr. 5, 2012).
Nandamuri et al., "Chemical vapor deposition of graphene films," Nanotechnology 21(14): 1-4 (Mar. 10, 2010).
Nayini et al., "Synthesis and characterization of functionalized carbon nanotubes with different wetting behaviors and their influence on the wetting properties of carbon nanotubes/polymethylmethacrylate coatings," Progress in Organic Coatings 77(6): 1007-1014 (Mar. 2014).
Sun et al., "Growth of graphene from solid carbon sources," Nature 468(7323): 549-552 (Nov. 25, 2010; including corrigendum in Nature 471(7336): 124 (Mar. 2011).
Tang et al., "Highly wrinkled cross-linked graphene oxide membranes for biological and charge-storage applications," Small 8(3): 423-431 (Feb. 6, 2012; first published online Dec. 13, 2011).
Adiga et al., "Nanoporous Materials for Biomedical Devices," JOM 60: 26-32 (Mar. 25, 2008).
AMI Applied Membranes Inc. (undated). FilmTec Nanofiltration Membrane Elements. Retrieved Jun. 1, 2016, from http://www.appliedmembranes.com/filmtec-nanofiltration-membrane-elements.html.
Apel, "Track etching technique in membrane technology," Radiation Measurements 34(1-6): 559-566 (Jun. 2001).
Bae et al., "Roll-to-roll production of 30-inch graphene films for transparent electrodes," Nature Nanotechnology 5: 574-578 (Jun. 20, 2010).
Bai et al., "Graphene nanomesh," Nature Nanotechnology 5: 190-194 (Feb. 14, 2010).
Baker. (2004). Track-etch Membranes. In Membrane Technology and Applications (2nd ed., pp. 92-94). West Sussex, England: John Wiley & Sons.
Butler et al. "Progress, Challenges, and Opportunities in Two-Dimensional Materials Beyond Graphene", Materials Review 7(4): 2898-2926 (Mar. 6, 2013).
Chhowalla et al., "The chemistry of two-dimensional layered transition metal dichalcogenide nanosheets," Nature Chemistry 5: 263-275 (Mar. 20, 2013).
Childres et al., "Effect of oxygen plasma etching on graphene studied using Raman spectroscopy and electronic transport measurements," New Journal of Physics 13 (Feb. 10, 2011).
Clochard. (undated). Radiografted track-etched polymer membranes for research and application [Scholarly project]. In Laboratoire Des Solides Irradiés. Retrieved Jun. 2, 2016, from http://iramis.cea.fr/radiolyse/5juin2015/Clochard.pdf.
Cohen-Tanugi et al, "Water Desalination across Nanoporous Graphene," ACS Nano Letters 12(7): 3602-3608 (Jun. 5, 2012).
Cohen-Tanugi, "Nanoporous graphene as a water desalination membrane," Thesis: Ph.D., Massachusetts Institute of Technology, Department of Materials Science and Engineering (Jun. 2015).
Colton, "Implantable biohybrid artificial organs," Cell Transplantation 4(4): 415-436 (Jul.-Aug. 1995).
Desai et al., "Nanoporous microsystems for islet cell replacement," Advanced Drug Delivery Reviews 56: 1661-1673 (Jul. 23, 2004).
Fischbein et al., "Electron beam nanosculpting of suspended graphene sheets," Applied Physics Letters 93(113107): 1-3, (Sep. 16, 2008).
Fissell et al., "High-Performance Silicon Nanopore Hemofiltration Membranes," NIH-PA Author Manuscript, PMC, (Jan. 5, 2010), also published in J. Memb. Sci. 326(1): 58-63 (Jan. 5, 2009).
Gimi et al., "A Nanoporous, Transparent Microcontainer for Encapsulated Islet Therapy," J. Diabetes Sci. Tech. 3(2): 1-7 (Mar. 2009).
Jiang et al., "Porous Graphene as the Ultimate Membrane for Gas Separation," Nano Letters 9(12): 4019-4024 (Sep. 23, 2009).
Joshi et al., "Precise and ultrafast molecular sieving through graphene oxide membranes", Science 343(6172): 752-754 (Feb. 14, 2014).
Kanani et al., "Permeability—Selectivity Analysis for Ultrafiltration: Effect of Pore Geometry," NIH-PA Author Manuscript, PMC, (Mar. 1, 2011), also published in J. Memb. Sci. 349(1-2): 405 (Mar. 1, 2010).
Karan et al., "Ultrafast Viscous Permeation of Organic Solvents Through Diamond-Like Carbon Nanosheets," Science 335: 444-447 (Jan. 27, 2012).
Kim et al., "Fabrication and Characterization of Large Area, Semiconducting Nanoperforated Graphene Materials," Nano Letters 10(4): 1125-1131 (Mar. 1, 2010).
Kim et al., "The structural and electrical evolution of graphene by oxygen plasma-induced disorder," Nanotechnology IOP 20(375703): 1-8 (Aug. 26, 2009).
Koski and Cui, "The New Skinny in Two-Dimensional Nanomaterials", ACS Nano 7(5): 3739-3743 (May 16, 2013).
Liu et al., "Atomically Thin Molybdenum Disulfide Nanopores with High Sensitivity for DNA Translocation," ACS Nano 8(3): 2504-2511 (Feb. 18, 2014).
Liu et al., "Graphene Oxidation: Thickness-Dependent Etching and Strong Chemical Doping," Nano Letters 8(7): 1965-1970 (Jun. 19, 2008).
Mishra et al., "Functionalized Graphene Sheets for Arsenic Removal and Desalination of Sea Water," Desalination 282: 39-45 (Nov. 1, 2011).
Morse, "Scalable Synthesis of Semiconducting Nanopatterned Graphene Materials," InterNano Resources for Nanomanufacturing (undated). Retrieved Jun. 2, 2016 from: http://www.internano.org/node/345.
Nair et al., "Unimpeded Permeation of Water Through Helium-Leak-tight Graphene-Based Membranes," Science 335: 442-444 (Jan. 27, 2012).

(56) References Cited

OTHER PUBLICATIONS

O'Hern et al. "Selective Molecular Transport through Intrinsic Defects in a Single Layer of CVD Graphene," ACS Nano, 6(11): 10130-10138 (Oct. 2, 2012).
O'Hern et al., "Selective Ionic Transport through Tunable Subnanometer Pores in Single-Layer Graphene Membranes," Nano Letters 14(3): 1234-1241 (Feb. 3, 2014).
Paul, "Creating New Types of Carbon-Based Membranes," Science 335: 413-414 (Jan. 27, 2012).
Schweicher et al., "Membranes to achieve immunoprotection of transplanted islets," NIH-PA Author Manuscript, PMC, (Nov. 13, 2014), also published in Frontiers in Bioscience (Landmark Ed) 19: 49-76 (Jan. 1, 2014).
Sint et al., "Selective Ion Passage through Functionalized Graphene Nanopores," JACS 130: 16448-16449 (Nov. 14, 2008).
Suk et al., "Water Transport Through Ultrathin Graphene," Journal of Physical Chemistry Letters 1(10): 1590-1594 (Apr. 30, 2010).
Tan et al., "Beta-cell regeneration and differentiation: how close are we to the 'holy grail'?" J. Mol. Encodrinol. 53(3): R119-R129 (Dec. 1, 2014).
Vlassiouk et al., "Versatile ultrathin nanoporous silicon nitride membranes," Proc. Natl. Acad. Sci. USA 106(50): 21039-21044 (Dec. 15, 2009).
Wadvalla, "Boosting agriculture through seawater," Nature Middle East (Jul. 2, 2012). Retrieved Jun. 1, 2016 from: natureasia.com/en/nmiddleeast/article/10.1038/nmiddleeast.2012.92?WT.mc_id=FBK NatureMEast].
Wikipedia, "Ion track." Jun. 1, 2016. Retrieved Jun. 1, 2016 from: en.wikipedia.org/wiki/ion_track.
Xu et al., "Graphene-like Two-Dimensional Materials", Chemical Reviews 113: 3766-3798 (Jan. 3, 2013).
Zan et al., "Graphene Reknits Its Holes," Nano Lett. 12(8): 3936-3940 (Jul. 5, 2012).
Zhao et al. "Two-Dimensional Material Membranes: An Emerging Platform for Controllable Mass Transport Applications," Small 10(22): 4521-4542 (Sep. 10, 2014).
Barreiro et al. "Understanding the catalyst-free transformation of amorphous carbon into graphene by current-induced annealing," Scientific Reports, 3 (Article 1115): 1-6 (Jan. 2013).
Botari et al., "Graphene healing mechanisms: A theoretical investigation," Carbon, 99: 302-309 (Apr. 2016) (published online Dec. 2015).
Chen et al., "Defect Scattering in Graphene," Physical Review Letters, 102: 236805-1-236805-4 (Jun. 2009).
Chen et al., "Self-healing of defected graphene," Applied Physics Letters, 102(10): 103107-1-103107-5 (Mar. 2013).
Cheng et al., "Ion Transport in Complex Layered Graphene-Based Membranes with Tuneable Interlayer Spacing," Science Advances, 2(2): e1501272 (9 pages) (Feb. 2016).
Crock et al., "Polymer Nanocomposites with Graphene-Based Hierarchical Fillers as Materials for Multifunctional Water Treatment Membranes," Water Research, 47(12): 3984-3996 (Aug. 2013) (published online Mar. 2013).
Han et al., "Ultrathin Graphene Nanofiltration Membrane for Water Purification," Advanced Functional Materials, 23(29): 3693-3700 (Aug. 2013).
International Search Report and Written Opinion in PCT/US2016/027583 dated Jan. 13, 2017.
Written Opinion in PCT/US2016/027590 dated Jan. 6, 2017.
International Search Report and Written Opinion in PCT/US2016/027594 dated Jan. 13, 2017.
1. International Search Report and Written Opinion in PCT/US2016/027628 dated Jan. 9, 2017.
International Search Report and Written Opinion in PCT/US2016/027631 dated Jan. 13, 2017.
International Search Report and Written Opinion in PCT/US2016/027632 dated Jan. 9, 2017.
Written Opinion in PCT/US2016/052010 dated Dec. 20, 2016.
International Search Report in PCT/US2016/027629 dated Dec. 8, 2016.
International Search Report in PCT/US2016/052007 dated Dec. 27, 2016.
Kjeldsen, T., "Yeast secretory expression of insulin precursors," Appl Microbiol Biotechnol, 54: 277-286 (May 2000).
Lin et al., "A Direct and Polymer-Free Method for Transferring Graphene Grown by Chemical Vapor Deposition to Any Substrate," ACSNANO, 8(2): 1784-1791 (Jan. 2014).
Liu et al. "Synthesis of high-quality monolayer and bilayer graphene on copper using chemical vapor deposition," Carbon, 49(13): 4122-4130 (Nov. 2011) (published online May 2011).
O'Hern et al., "Nanofiltration across defect-sealed nanoporous monolayer graphene," Nano Letters, 15(5): 3254-3260 (Apr. 2015).
U.S. Corrected Notice of Allowance in U.S. Appl. No. 13/480,569 dated May 26, 2015.
U.S. Notice of Allowance for U.S. Appl. No. 14/610,770 dated Apr. 25, 2016.
U.S. Notice of Allowance in U.S. Appl. No. 14/819,273 dated Dec. 14, 2016.
U.S. Notice of Allowance in U.S. Appl. No. 13/480,569 dated Feb. 27, 2015.
U.S. Office Action in U.S. Appl. No. 13/480,569 dated Jul. 30, 2014.
U.S. Office Action in U.S. Appl. No. 14/856,471 dated Dec. 1, 2016.
U.S. Restriction Requirement in U.S. Appl. No. 14/193,007 dated Jul. 17, 2015.
Wang et al., "Graphene Oxide Membranes with Tunable Permeability due to Embedded Carbon Dots," Chemical Communications, 50(86): 13089-13092 (Nov. 2014) (published online Sep. 2014).
Xu et al., "Graphene Oxide-$TiO_2$ Composite Filtration Membranes and their Potential Application for Water Purification," Carbon, 62: 465-471 (Oct. 2013) (published online Jun. 2013).
Zhao et al., "A glucose-responsive controlled release of insulin system based on enzyme multilayers-coated mesoporous silica particles," Chem. Commun., 47: 9459-9461 (Jun. 2011).
Notice of Allowance for U.S. Appl. No. 14/819,273 dated Oct. 28, 2016.
U.S. Office Action for U.S. Appl. No. 14/193,007 dated Oct. 21, 2016.
U.S. Office Action for U.S. Appl. No. 14/193,007 dated Dec. 21, 2015.
U.S. Office Action for U.S. Appl. No. 14/193,007 dated Jul. 1, 2016.
International Search Report dated Dec. 4, 2015, in related international application PCT/US2015/048205.
International Search Report dated Jun. 10, 2015, from related international application PCT/US15/20201.
Chen et al., "Hierarchically porous graphene-based hybrid electrodes with excellent electrochemical performance", Journal of Materials Chemistry A: Materials for Energy and Sustainability, vol. 1, No. 33, Jan. 1, 2013, pp. 9409-9413.
Chinese Office Action in Application No. 201580006829.5 dated Jan. 23, 2018 (with English translation) (13 pages).
European Extended Search Report in Application No. 15786691.4 dated Dec. 1, 2017 (10 pages).
European Extended Search Report in Application No. 15789852.9 dated Dec. 6, 2017 (8 pages).
Japanese Office Action in Application No. 2017-042023 dated Jan. 9, 2018 (with English translation) (9 pages).
Singapore Search Report and Written Opinion in Application No. 11201701654U dated Dec. 6, 2017 (6 pages).
Taiwanese Office Action in Application No. 102146079 dated Dec. 12, 2017 (with English translation) (4 pages).
U.S. Notice of Allowance in U.S. Appl. No. 14/843,944 dated Feb. 9, 2018 (9 pages).
U.S. Office Action for U.S. Appl. No. 15/099,482 dated Feb. 23, 2018 (9 pages).
U.S. Office Action in U.S. Appl. No. 14/609,325 dated Jan. 16, 2018 (11 pages).
U.S. Office Action in U.S. Appl. No. 14/656,190 dated Jan. 10, 2018 (14 pages).
U.S. Office Action in U.S. Appl. No. 14/856,471 dated Jan. 11, 2018 (36 pages).
U.S. Office Action in U.S. Appl. No. 15/099,099 dated Feb. 15, 2018 (13 pages).

(56) References Cited

OTHER PUBLICATIONS

U.S. Office Action in U.S. Appl. No. 15/099,588 dated Feb. 1, 2018 (6 pages).
Wang et al., "Preparation of high-surface-area carbon nanoparticle/graphene composites", Carbon, Elsevier, Oxford, GB, vol. 50, No. 10, Apr. 8, 2012, pp. 3845-3853.
Anasori et al., "2D metal carbides and nitrides (MXenes) for energy storage", Nature Reviews, vol. 2, Article No. 16098, Jan. 17, 2017, pp. 1-17.
Australian Office Action for Appl. Ser. No. 2018200090 dated Apr. 30, 2019 (4 pages).
Huang et al., "Ultrathin Carbon Molecular Sieve Films and Room-Temperature Oxygen Functionalization for Gas-Sieving", ACS Applied Maters & Interfaces 2019, vol. 11, Apr. 16, 2019, pp. 16729-16736.
Japanese Office Action for Appl. Ser. No. 2016-566751 dated Jun. 7, 2019 (8 pages).
Mojtabavi et al., "Single-Molecule Sensing Using Nanopores in Two-Dimensional Transition Metal Carbide (MXene) Membranes", American Chemical Society, ACS Nano 2019, vol. 13, Mar. 7, 2019, pp. 3042-3053.
Neumann et al., "Bottom-Up Synthesis of Graphene Monolayers with Tunable Crystallinity and Porosity", American Chemical Society, ACS Nano, May 21, 2019, pp. A-M (13 pages).
Pang et al., "Applications of 2D MXenes in energy conversion and storage systems", Chemical Society Review, 2019, vol. 48, No. 1, Jun. 25, 2018, pp. 72-133.
U.S. Advisory Action for U.S. Appl. No. 15/099,239 dated Jun. 21, 2019 (7 pages).
U.S. Final Office Action for U.S. Appl. No. 14/707,808 dated Jun. 26, 2019 (37 pages).
U.S. Non-Final Office Action for U.S. Appl. No. 15/308,351 dated Jun. 3, 2019 (9 pages).
U.S. Notice of Allowance for U.S. Appl. No. 15/099,269 dated Jun. 6, 2019 (8 pages).

\* cited by examiner

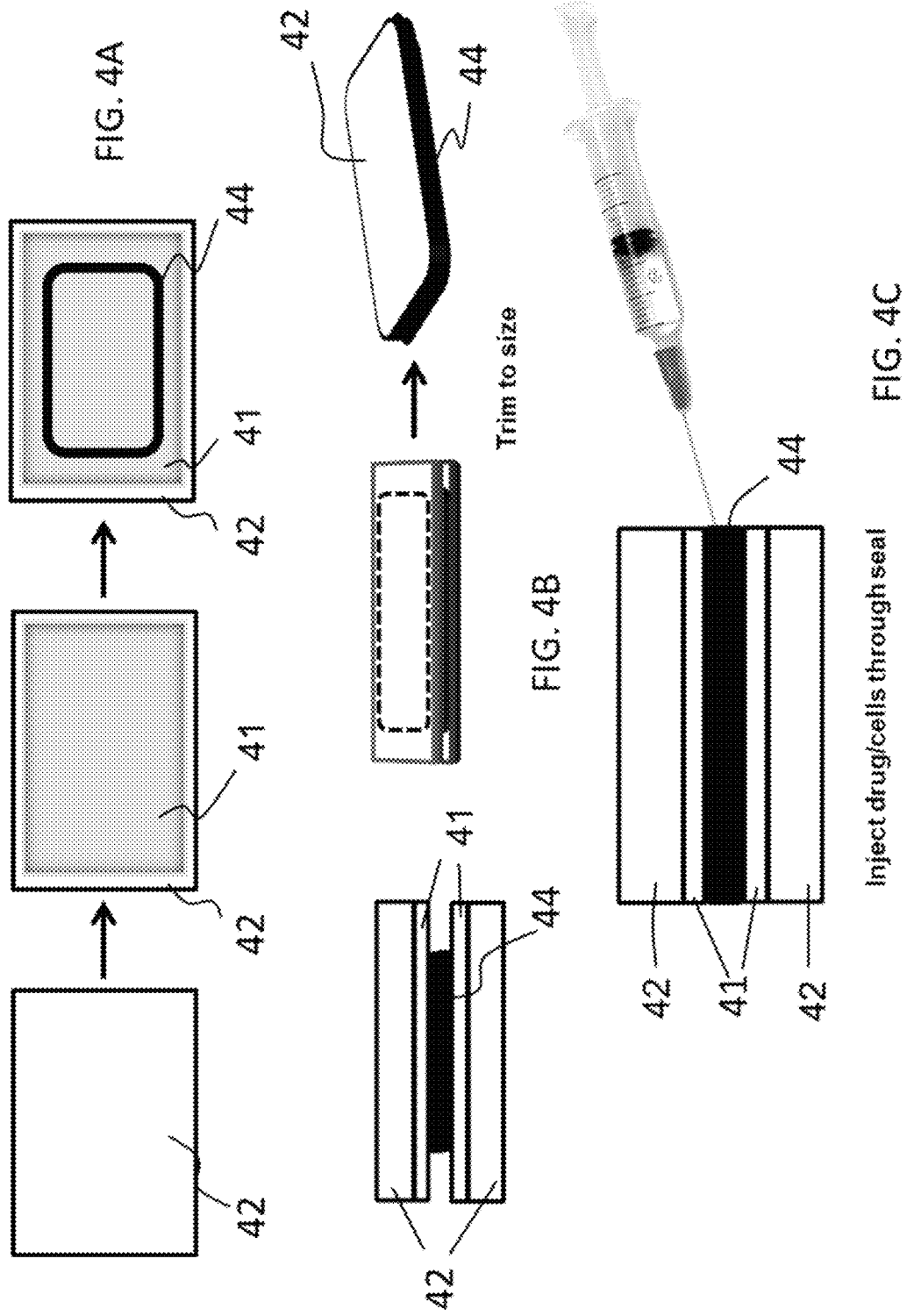

METHODS FOR IN VIVO AND IN VITRO USE OF GRAPHENE AND OTHER TWO-DIMENSIONAL MATERIALS

BACKGROUND

Drug and cell delivery in both immune competent and immune incompetent organisms is a problem in medical research and practice today. Recent studies use polymeric devices and hydrogels as a delivery vehicle. Some examples include polytetrafluoroethylene (e.g., expanded PTFE) with a backing of unwoven polyester mesh, silicone, hydrogels, alginate, cellulose sulfate, collagen, gelatin, agarose, chitosan and the like. Current delivery vehicles and devices are challenged by biofouling, biocompatibility issues, and delayed response. The thickness of current state devices can limit efficacy, due in part to limited diffusion of nutrients into the devices and/or impeded transfer of substances into and out of the device. Low permeability, at least in part, due to thickness and mechanical stability in view of physical stress and osmotic stress can also be problematic. Moreover, replicating the cellular walls, selective channels, and the semi-permeance that biological membranes provide has long proven to be a challenge for synthetic membranes or semi-permeable walls, especially when integrating those membranes in vitro or in vivo. In addition, current membranes insufficiently achieve immunoisolation, especially in the context of xenogenic, allogenic, and autogenic transplants.

In view of the foregoing, improved techniques for transportation, delivery, separation, and forming selective barriers of substances under a variety of conditions, including in a biological environment, would be of considerable benefit in the art.

SUMMARY

Some embodiments comprise devices comprising a first enclosure and a second enclosure, wherein the first enclosure and the second enclosure are in direct fluid communication with one another, wherein the enclosures independently comprise a perforated two-dimensional material encapsulating a compartment, or a portion thereof, with at least one substance, and wherein the first enclosure and/or second enclosure allows release of the substance to an environment external to the device via passage across the perforated two-dimensional material. In some embodiments, the substance can be released to an environment external to the enclosure by passage through holes in the perforated two-dimensional material. In some embodiments, the first enclosure and the second enclosure are in direct fluid contact with one another.

In some embodiments, the first enclosure and the second enclosure are connected by microfluidic channels. In some embodiments, the first enclosure and the second enclosure are in direct fluid contact via microfluidic channels.

In some embodiments, the device comprises more than two enclosures, wherein each enclosure is in direct fluid contact with at least one other enclosure.

In some embodiments, fluids and/or the substance pass between the first enclosure and the second enclosure. In some embodiments, the fluids and/or the substance pass between the first enclosure and the second enclosure via osmosis, applied electric potential, concentration gradients, diffusion, piston-induced transport, triggered movement, or a combination thereof. In some embodiments, the device comprises an osmotic pump that promotes passage fluids and/or the substance between the first enclosure and the second enclosure.

In some embodiments, substances in the first enclosure are released into an environment external to the device at a different rate and/or at different relative concentration than substances in the second enclosure.

In some embodiments, the first enclosure is in direct fluid communication with an environment external to the device. In some embodiments, the second enclosure is in direct fluid communication with the first enclosure, and the second enclosure is not in direct fluid communication with the environment external to the device.

In some embodiments, each enclosure comprises a single compartment that does not contain sub-compartments. In some embodiments, the first enclosure and second enclosure independently comprise two or more sub-compartments, wherein at least one sub-compartment is in direct fluid communication with an environment external to the device. In some embodiments, each sub-compartment comprises a perforated two-dimensional material.

In some embodiments, the substance in the compartment is selected from the group consisting of atoms, ions, molecules, macromolecules, viruses, cells, particles, biological molecules, DNA, RNA, proteins, nucleic acids, pharmaceuticals, drugs, medicaments, therapeutics, biologics, small molecules, and combinations thereof. In some embodiments, cells are enclosed in the compartment. In some embodiments, the perforated two-dimensional material has pores with a size sufficient to retain the cell within the compartment and to exclude immune cells and immune complexes in the environment external to the compartment from entering the compartment.

Some embodiments comprise methods of releasing a substance comprising exposing a device to an environment to thereby release into the environment at least one substance enclosed in the device, wherein the device comprises a first enclosure and a second enclosure, wherein the enclosures independently comprise a perforated two-dimensional material encapsulating independent compartments, or portions thereof, with the substance. In some embodiments, the first enclosure and the second enclosure are in direct fluid communication with one another. In some embodiments, the environment is a biological environment. In some embodiments, the substance is a pharmaceutical. In some embodiments, at least one compartment contains cells which are not released from the respective enclosure. In some embodiments, the cells produce the substance released from the enclosure.

Some embodiments comprise an artificial liver comprising a first enclosure and a second enclosure in direct fluid contact with one another, wherein the enclosures independently comprise a perforated two-dimensional material encapsulating a compartment, or a portion thereof, with at least one substance, wherein the first enclosure and/or second enclosure allows release of the substance to an environment external to the device via passage across the perforated two-dimensional material, and wherein the first enclosure and the second enclosure are in direct fluid contact with one another.

Some embodiments comprise devices comprising a first enclosure and a second enclosure, wherein the enclosures independently comprise a perforated two-dimensional material encapsulating independent compartments, or portions thereof, and a means for moving substances and/or fluids between the first enclosure and the second enclosure. In some embodiments, the means comprises osmosis, applied electric potential, concentration gradients, diffusion, piston-induced transport, triggered movement, or a combination thereof.

Some embodiments comprise enclosures formed from perforated graphene or other perforated two-dimensional materials. The enclosures can house various substances therein allowing bi-directional movement of selected substances to and from the interior of the enclosure, retaining other selected substances therein and preventing entry of yet other selected substances into the enclosure. The enclosure can be employed to release one or more selected substances into an environment external to the enclosure, to allow entry into the enclosure of one or more selected substances from an environment external to the enclosure, to inhibit and preferably prevent entry of one or more selected substances from the external environment into the enclosure, to retain (inhibit or preferably prevent exit) one or more selected substances within the enclosure or a combination of these applications. The hole or aperture size or range of sizes can be selected based on the specific application of the enclosure. The term enclosure refers to a space for receiving one or more substances formed at least in part by perforated two-dimensional material, such as a graphene-based material, where one or more substances in the enclosure can exit the enclosure by passage through the perforated two-dimensional material. In some embodiments, one or more substances from the external environment can enter the enclosure by passage through the perforated two-dimensional material. In some embodiments the external environment is a biological environment, including an in vivo biological environment or an in vitro biological environment.

In some embodiments, an enclosure comprises one or more than one sub-compartments, and each sub-compartment can comprise a perforated two-dimensional material, such that at least a portion of the walls or sides forming the sub-compartment comprise perforated two-dimensional material. Fluid communication can be achieved by selective passage of one or more substances in and/or out of the enclosure or sub-compartment thereof. The fluid may be liquid or gas and includes fluids having entrained gases. Substances may be dissolved or suspended or otherwise carried in a fluid. The fluid can be aqueous. A sub-compartment can be in direct fluid communication with adjacent sub-compartments or the external environment (where adjacent sub-compartments share at least one wall or side). In some embodiments, one or more sub-compartments can be in direct fluid communication with adjacent sub-compartments, but not in direct fluid communication with the external environment. In some embodiments, at least one sub-compartment in an enclosure is in direct fluid communication with an external environment. An enclosure can have various configurations of sub-compartments. A sub-compartment can have any shape. A sub-compartment may, for example, be spherical, cylindrical or rectilinear. In some embodiments, sub-compartments can be nested. For example, such nested sub-compartments may be used as reservoirs of reactants, nutrients and the like within a compartment or sub-compartment. In some embodiments, the enclosure can have a central sub-compartment which shares a wall or side with a plurality of surrounding sub-compartments. In some embodiments, sub-compartments may be linearly aligned within the enclosure. In some embodiments, an enclosure contains two-sub-compartments. In some embodiments, an enclosure contains three, four, five or six sub-compartments. In some embodiments, a sub-compartment may be fully contained within another sub-compartment, wherein the inner sub-compartment is in direct fluid communication with the outer sub-compartment and the outer-sub-compartment is in direct fluid communication with the external environment. Thus, in some embodiments the inner sub-compartment is in indirect rather than direct fluid communication with the external environment. In some embodiments where an enclosure contains a plurality of sub-compartments, at least one sub-compartment is in direct fluid communication with the external environment and remaining sub-compartments are in direct fluid communication with an adjacent sub-compartment, but may not all be in direct fluid communication with the external environment. In some embodiments where an enclosure contains a plurality of sub-compartments, all sub-compartments may be in direct fluid communication with the external environment.

An enclosure encapsulates at least one substance. In some embodiments, an enclosure can contain more than one different substance. Different substances may be in the same or in different sub-compartments. In some embodiments, not all of the different substances in the enclosure are released to an environment external to the enclosure. In some embodiments, all of the different substances in the enclosure are released to an external environment. In some embodiments, the rate of release of different substances from the enclosure into an external environment is the same. In some embodiments, the rate of release of different substances from the enclosure into an external environment is different. In some embodiments, the relative amounts of different substances released from the enclosure can be the same or different. The rate of release of substances from the enclosure can be based on concentration gradients and/or relative diffusivities, and/or can be controlled by choice of hole size, hole shape, hole functionalization, surface functionalization, or a combination thereof.

In some embodiments, an enclosure comprises perforated two-dimensional material encapsulating a substance, such that the substance is released to an environment external to the enclosure by passage through the holes in the perforated two-dimensional material, wherein the enclosure comprises a port for loading or unloading the substance to/from the enclosure.

In some embodiments, a device for delivering a substance to an environment comprises a sheath for receiving an enclosure, the enclosure comprising perforated two-dimensional material encapsulating a substance, such that the substance is released to an environment external to the enclosure by passage through the holes in the perforated two-dimensional material.

Methods for transporting and delivering substances in a biological environment are also described. In some embodiments, the methods can include introducing an enclosure comprising graphene or other two-dimensional material into a biological environment, and releasing at least a portion of a substance in the enclosure to the biological environment. In some embodiments, the methods can include introducing an enclosure formed from graphene into a biological environment, and receiving a substance from the biological environment into the enclosure.

In some embodiments, the invention provides a method comprising: introducing an enclosure comprising perforated two-dimensional material to a an environment, the enclosure containing at least one substance; and releasing at least a portion of at least one substance through the holes of the two-dimensional material to the environment external to the enclosure.

In some embodiments, the invention provides a method comprising: introducing an enclosure comprising perforated two-dimensional material to an environment, the enclosure containing at least one substance and a port for loading or unloading the at least one substance to/from the enclosure; and releasing at least a portion of at least one substance through the holes of the two-dimensional material to the environment external to the enclosure.

In some embodiments, the invention provides a method comprising: introducing an enclosure comprising perforated two-dimensional material to an environment, the enclosure containing at least one first substance; and receiving a second substance from the environment into the enclosure. In some embodiments, the first substance is cells, a second substance is nutrients and another second substance is oxygen.

In some embodiments, the invention provides a method comprising: introducing an enclosure comprising perforated two-dimensional material to an environment, the enclosure containing at least one first substance; and receiving a second substance from the environment into the enclosure. In some embodiments, the first substance is cells, a second substance is nutrients and another second substance is oxygen.

In some embodiments, the invention provides a method of using a device to deliver a substance to an environment comprising: implanting a sheath in a subject; and inserting an enclosure in the sheath, wherein the enclosure comprises perforated two-dimensional material encapsulating a substance, such that the substance is released to an environment external to the enclosure by passage through the holes in the perforated two-dimensional material. In some embodiments, the sheath is substantially rigid or able to withstand pressures less than or equal to 10 psi.

BRIEF DESCRIPTION OF THE DRAWINGS

FIGS. 4A-C illustrate some embodiments for preparing an enclosure.

DETAILED DESCRIPTION

Figure 1:
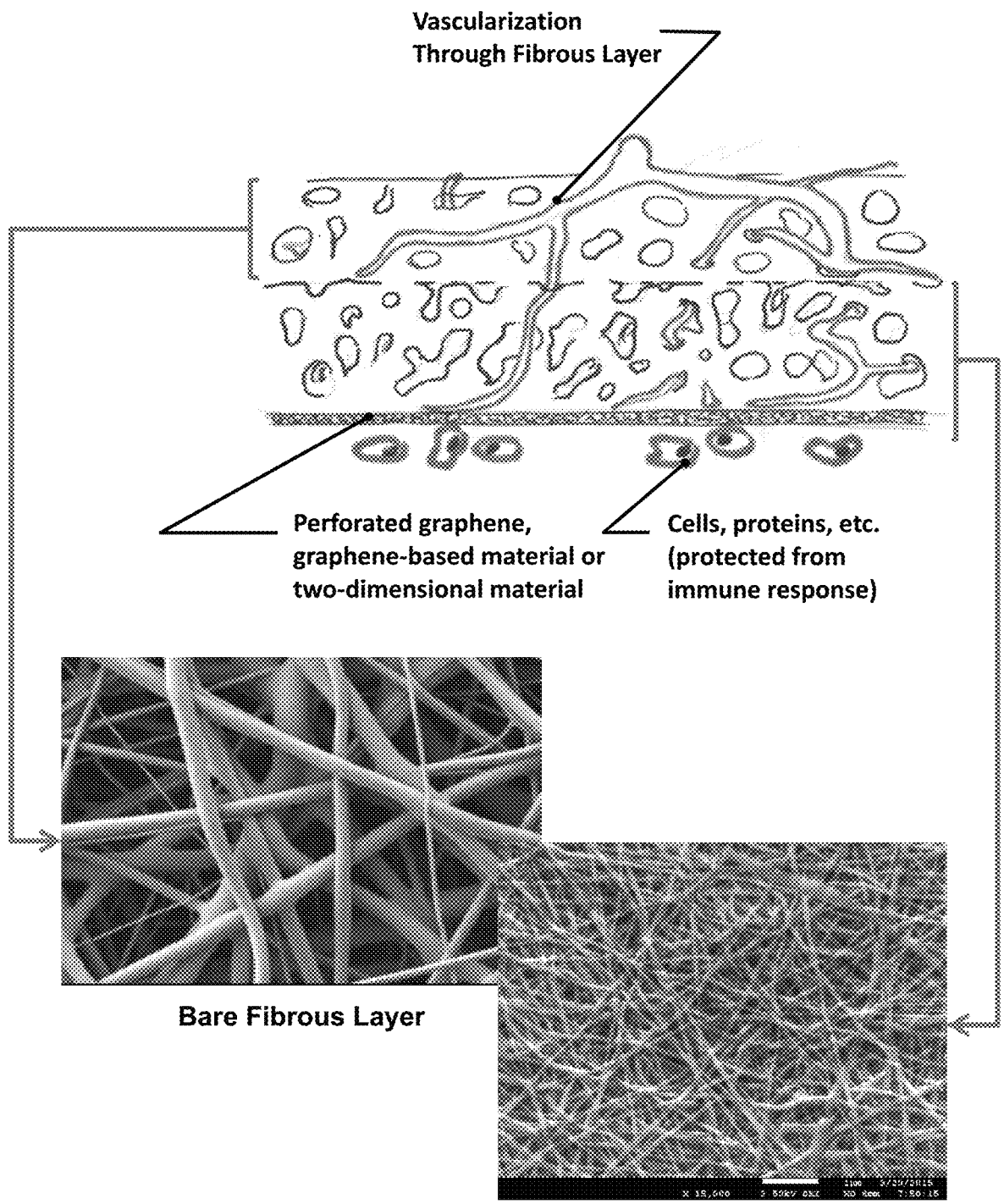
FIG. 1 shows an illustrative schematic of some embodiments of a composite structure comprising a two-dimensional material and a two fibrous layers. The fibrous layers allow for capillary ingrowth that brings the blood supply close to the two-dimensional material to facilitate exchange of molecules with the cells, proteins, tissue or the like on the opposite side of the two-dimensional material. SEM micrographs show embodiments with fibrous layers that have different pore sizes.

Methods of some embodiments comprise using graphene-based materials and other two-dimensional materials to transport, deliver, and or separate substances. Some embodiments comprise to enclosures formed from graphene-based materials and other two-dimensional materials on or suspended across a suitable substrate or substrates which can be porous or non-porous, which can serve as a delivery vehicle in an environment external to the enclosure, particularly in a biological environment. Some embodiments comprise enclosures formed from graphene-based materials or other two-dimensional materials containing cells, pharmaceuticals, therapeutic agents and other medicaments.

In some embodiments, enclosures are configured for long-term in vivo implantation for the delivery of pharmaceuticals, therapeutic agents or other medicaments directly to a biological environment can improve compliance with a dosing regimen relative to traditional oral and intravenous delivery methods that require patient or medical personnel intervention. In some embodiments, enclosures may be configured as oral capsules or suppositories. In some embodiments, an enclosure may be provided in a gelatin capsule for ease of swallowing. In some embodiments, enclosures may be physically coupled with or integrated into a device that ensures contact of the enclosure with the skin of a subject for transdermal drug delivery. For example, a device for ensuring contact between an enclosure and skin may comprise a pocket for receiving the enclosure and microneedles or other relief features for penetrating the stratum cornea and anchoring the device and enclosure to the skin of a subject. In some embodiments, a sheath or vascularization device may be provided or surgically placed within a subject and enclosures may be inserted into and removed from the sheath or vascularization device. The sheath or vascularization device may, for example, be tubular and rigid, perforated or permeable, so long as it is capable of withstanding forces provided in an in vivo environment. In some embodiments, a sheath or vascularization device is biocompatible. In some embodiments, a sheath or vascularization device comprises graphene. Enclosures disposed in a sheath or vascularization device may be exchanged in a minimally invasive manner when their contents are depleted, damaged, or otherwise compromised, or when an enclosure captures an analyte for ex vivo analysis. For example, an interior of an enclosure may comprise a molecule, protein (e.g., antibody), or other substance (e.g., chelating agent) that ionically, covalently or electrostatically binds the analyte, thereby producing a chemical complex having a diameter too large to escape from the enclosure. In some embodiments, the analyte may be bound to an interior surface of an enclosure. In some embodiments, enclosures that capture analytes for ex vivo analysis may be used without a sheath or vascularization device. For example, an enclosure for capturing an analyte may be surgically inserted into a subject at a specific site for a period of time, then surgically removed, or an enclosure for capturing an analyte may be ingested and passed through the digestive system.

In some embodiments, enclosures can be configured to deliver pharmaceuticals, therapeutic agents or other medicaments directly to a biological environment. In some embodiments, enclosure are used for treating medical conditions (including chronic medical conditions) requiring a substantially continuous release and/or slow release of a pharmaceutical, therapeutic agent, or other medicament. In some embodiments, enclosures elute drugs to a biological environment at a rate that is substantially constant, e.g., in accordance with zero-order kinetics. In some embodiments, the enclosures elute drugs with a delayed release profile. In some embodiments, implanted or ingested enclosures elute drugs with a delayed release profile.

Graphene represents an atomically thin layer of carbon in which the carbon atoms reside as closely spaced atoms at regular lattice positions, and can possess favorable mechanical and electrical properties, including optical properties, thinness, flexibility, strength, conductivity (e.g., for potential electrical stimulation), tunable porosity when perforated, and permeability. The regular lattice positions can have a plurality of defects present therein, which can occur natively or be intentionally introduced to the graphene basal plane. Such defects will also be equivalently referred to herein as "pores," "apertures," "perforations," or "holes." Aside from such apertures, graphene and other two-dimensional materials can represent an impermeable layer to many substances. Therefore, when sized properly, the apertures in the impermeable layer of such materials can be useful for ingress and egress to an enclosure formed from the impermeable layer.

Some embodiments comprise graphene-based enclosures that are capable of delivering a target to an in vivo or in vitro location while maintaining a barrier (e.g., an immunoisolation barrier) in an organism or similar biological environment. Encapsulation of molecules or cells with bi-directional transport across a semi-permeable membrane, such as perforated graphene or other two-dimensional materials, while sequestering cells or the like in a biological environment (such as in an organism) can enable treatments to overcome graft rejection, the need for repeated dosages of drugs (e.g., drugs with short half-lives), and excess surgical intervention. The foregoing can be accomplished by providing technology to allow xenogenic and allogenic tissue transplants, autogenic transplants for subjects with autoimmune disorders, long term low-dose therapeutic levels of a drug, and even sense-response paradigms to treat aliments after surgical intervention, thereby reducing complications from multiple surgeries at the same site.

Some embodiments comprise enclosures formed by two-dimensional materials configured for deployment within a tissue or organ, e.g., spanning a space between walls of a tissue or organ. For example, enclosures may be suspended inside or adjacent to an artery or an organ. In some embodiments, inlet and outlet ports of an enclosure may be aligned with fluid flow within a blood vessel such that the device is configured in-line or in parallel with the fluid flow.

Some embodiments comprise enclosures formed by two-dimensional materials where the enclosure or a compartment thereof comprises at least one opening. For example, a doughnut-shaped or toroid-shaped enclosure comprising an opening can receive vasculature, nerves or nerve bundles, heart valves, bones and the like through the opening, which may anchor or secure the enclosure at a site in need of therapeutic agents contained within the enclosure.

Some embodiments comprise enclosures formed by two-dimensional materials, where the enclosure or a component thereof comprises a lumen in the form of a tube or port for introducing or removing cells, pharmaceuticals, therapeutic agents and other substances into/from the enclosure. Such a lumen, tube, or port can be joined with the two-dimensional material of the enclosure, for example, by physical methods of clamping or crimping and/or chemical methods implementing a sealant (e.g., silicone). In some embodiments, the lumen, tube, or port can be joined with an impermeable region (which, e.g., can be non-graphene) that is connected or sealed to the two-dimensional material. In some embodiments, a lumen comprises a self-sealing end for receiving the substance via syringe.

In some embodiments, perforated graphene and other two-dimensional materials can readily facilitate the foregoing while surpassing the performance of current delivery vehicles and devices, including immune-isolating devices. Without being bound by theory, it is believed that graphene can accomplish the foregoing due to its thinness, flexibility, strength, conductivity (for potential electrical stimulation), tunable porosity, and permeability in the form of perforations therein. The thinness and subsequent transport properties across the graphene membrane surface can allow a disruptive time response to be realized compared to the lengthy diffusion seen with thicker polymeric membranes of comparable size performance.

Two-dimensional materials include those which are atomically thin, with thickness from single-layer sub-nanometer thickness to a few nanometers, and which generally have a high surface area. Two-dimensional materials include metal chalogenides (e.g., transition metal dichalogenides), transition metal oxides, hexagonal boron nitride, graphene, silicene and germanene (see: Xu et al. (2013) "Graphene-like Two-Dimensional Materials) Chemical Reviews 113: 3766-3798). Graphene represents a form of carbon in which the carbon atoms reside within a single atomically thin sheet or a few layered sheets (e.g., about 20 or less) of fused six-membered rings forming an extended sp2-hybridized carbon planar lattice. In its various forms, graphene has garnered widespread interest for use in a number of applications, primarily due to its favorable combination of high electrical and thermal conductivity values, good in-plane mechanical strength, and unique optical and electronic properties. Other two-dimensional materials having a thickness of a few nanometers or less and an extended planar lattice are also of interest for various applications. In some embodiments, a two dimensional material has a thickness of 0.3 to 1.2 nm or 0.34 to 1.2 nm. In some embodiments, a two dimensional material has a thickness of 0.3 to 3 nm or 0.34 to 3 nm.

In various embodiments, the two-dimensional material comprises a sheet of a graphene-based material. In some embodiments, the sheet of graphene-based material is a sheet of single or multilayer graphene or a sheet comprising a plurality of interconnected single or multilayer graphene domains. In some embodiments, the multilayer graphene domains have 2 to 5 layers or 2 to 10 layers. In some embodiments, the layer comprising the sheet of graphene-based material further comprises non-graphenic carbon-based material located on the surface of the sheet of graphene-based material. In some embodiments, the amount of non-graphenic carbon-based material is less than the amount of graphene. In some embodiments, the amount of graphene in the graphene-based material is from 60% to 95% or from 75% to 100%.

In some embodiments, the characteristic size of the perforation is from 0.3 to 10 nm, from 1 to 10 nm, from 5 to 10 nm, from 5 to 20 nm, from 5 to 25 nm, from 5 to 30 nm, from 7 to 25 nm, from 7 to 20 nm, from 10 to 25 nm, from 15 to 25 nm, from 10 nm to 50 nm, from 50 nm to 100 nm, from 50 nm to 150 nm, from 100 nm to 200 nm, or from 100 nm to 500 nm. In some embodiments, the average pore size is within the specified range. In some embodiments, 70% to 99%, 80% to 99%, 85% to 99% or 90 to 99% of the perforations in a sheet or layer fall within a specified range, but other pores fall outside the specified range.

The technique used for forming the graphene or graphene-based material is not believed to be particularly limited, and may be used to form single-layer graphene or graphene-based materials (SLG) or few-layer graphene or graphene-based materials (FLG). For example, in some embodiments, CVD graphene or graphene-based material can be used. In various embodiments, the CVD graphene or graphene-based material can be liberated from its growth substrate (e.g., Cu) and transferred to a polymer backing. Likewise, the techniques for introducing perforations to the graphene or graphene-based material are also not believed to be particularly limited, other than being chosen to produce perforations within a desired size range. Suitable techniques are described, for example, in U.S. Patent Pub. Nos. 2013/0249147, 2014/0272286 and 2015/0221474, each of which is incorporated by reference herein in its entirety. Perforations are sized to provide desired selective permeability of a species (atom, ion, molecule, DNA, RNA, protein, virus, cell, etc.) for a given application. Selective permeability relates to the propensity of a porous material or a perforated two-dimensional material to allow passage (or transport) of one or more species more readily or faster than other species. Selective permeability allows separation of species which exhibit different passage or transport rates. In two-dimensional materials selective permeability correlates to the dimension or size (e.g., diameter) of apertures and the relative effective size of the species. Selective permeability of the perforations in two-dimensional materials such as graphene-based materials can also depend on functionalization (e.g., of perforations if any, or the surface of the graphene-based material) and the specific species that are to be separated. Selective permeability can also depend on the voltage applied across the membrane. Separation of two or more species in a mixture includes a change in the ratio(s) (weight or molar ratio) of the two or more species in the mixture after passage of the mixture through a perforated two-dimensional material.

Graphene-based materials include, but are not limited to, single layer graphene, multilayer graphene or interconnected single or multilayer graphene domains and combinations thereof. In some embodiments, graphene-based materials also include materials which have been formed by stacking single or multilayer graphene sheets. In some embodiments, multilayer graphene includes 2 to 20 layers, 2 to 10 layers or 2 to 5 layers. In some embodiments, graphene is the dominant material in a graphene-based material. For example, a graphene-based material comprises at least 20% graphene, at least 30% graphene, or at least 40% graphene, or at least 50% graphene, or at least 60% graphene, or at least 70% graphene, or at least 80% graphene, or at least 90% graphene, or at least 95% graphene. In some embodiments, a graphene-based material comprises a range of graphene selected from 30% to 95%, or from 40% to 80% from 50% to 70%, from 60% to 95% or from 75% to 100%.

As used herein, a "domain" refers to a region of a material where atoms are uniformly ordered into a crystal lattice. A domain is uniform within its boundaries, but different from a neighboring region. For example, a single crystalline material has a single domain of ordered atoms. In some embodiments, at least some of the graphene domains are nanocrystals, having domain size from 1 to 100 nm or 10-100 nm. In some embodiments, at least some of the graphene domains have a domain size greater than 100 nm to 1 micron, or from 200 nm to 800 nm, or from 300 nm to 500 nm. Some embodiments comprise a domain size up to about 1 mm. "Grain boundaries" formed by crystallographic defects at edges of each domain differentiate between neighboring crystal lattices. In some embodiments, a first crystal lattice may be rotated relative to a second crystal lattice, by rotation about an axis perpendicular to the plane of a sheet, such that the two lattices differ in "crystal lattice orientation".

In some embodiments, the sheet of graphene-based material comprises a sheet of single or multilayer graphene or a combination thereof. In some embodiments, the sheet of graphene-based material is a sheet of single or multilayer graphene or a combination thereof. In some embodiments, the sheet of graphene-based material is a sheet comprising a plurality of interconnected single or multilayer graphene domains. In some embodiments, the interconnected domains are covalently bonded together to form the sheet. When the domains in a sheet differ in crystal lattice orientation, the sheet is polycrystalline.

In some embodiments, the thickness of the sheet of graphene-based material is from 0.34 to 10 nm, from 0.34 to 5 nm, or from 0.34 to 3 nm. In some embodiments, a sheet of graphene-based material comprises intrinsic or native defects. Intrinsic or native defects are those resulting from preparation of the graphene-based material in contrast to perforations which are selectively introduced into a sheet of graphene-based material or a sheet of graphene. Such intrinsic or native defects include, but are not limited to, lattice anomalies, pores, tears, cracks or wrinkles. Lattice anomalies can include, but are not limited to, carbon rings with other than 6 members (e.g. 5, 7 or 9 membered rings), vacancies, interstitial defects (including incorporation of non-carbon atoms in the lattice), and grain boundaries.

In some embodiments, the layer comprising the sheet of graphene-based material further comprises non-graphenic carbon-based material located on the surface of the sheet of graphene-based material. In some embodiments, the non-graphenic carbon-based material does not possess long range order and may be classified as amorphous. In some embodiments, the non-graphenic carbon-based material further comprises elements other than carbon and/or hydrocarbons. Non-carbon elements which may be incorporated in the non-graphenic carbon include, but are not limited to, hydrogen, oxygen, silicon, copper and iron. In some embodiments, the non-graphenic carbon-based material comprises hydrocarbons. In some embodiments, carbon is the dominant material in non-graphenic carbon-based material. For example, a non-graphenic carbon-based material comprises at least 30% carbon, or at least 40% carbon, or at least 50% carbon, or at least 60% carbon, or at least 70% carbon, or at least 80% carbon, or at least 90% carbon, or at least 95% carbon. In some embodiments, a non-graphenic carbon-based material comprises a range of carbon selected from 30% to 95%, or from 40% to 80%, or from 50% to 70%.

Nanomaterials that contain pores in its basal plane, regardless of whether they are intrinsically or natively present or intentionally created, will be referred to herein as "perforated two-dimensional materials." Exemplary perforated two-dimensional materials include perforated graphene-based materials and/or other perforated graphene. The term "perforated graphene-based materials" is used herein to denote a two-dimensional material comprising a graphene sheet with defects in its basal plane, regardless of whether the defects are intrinsically or natively present or intentionally produced. Perforated graphene-based materials include perforated graphene.

In some embodiments, the perforated two-dimensional material contains a plurality of holes of size (or size range) appropriate for a given enclosure application. The size distribution of holes may be narrow, e.g., limited to a 1-10%±3% deviation in size, or a 1-20%±5% deviation in size, or a 1-30%±5% deviation in size. In some embodiments, the characteristic dimension of the holes is selected for the application. For circular holes, the characteristic dimension is the diameter of the hole. In some embodiments relevant to non-circular pores, the characteristic dimension can be taken as the largest distance spanning the hole, the smallest distance spanning the hole, the average of the largest and smallest distance spanning the hole, or an equivalent diameter based on the in-plane area of the pore. These examples illustrate that various pore geometries or shapes may be implemented in a two-dimensional membrane, such as circular, oval, diamond, slits and the like. As used herein, perforated graphene-based materials include materials in which non-carbon atoms have been incorporated at the edges of the pores.

In various embodiments, the two-dimensional material comprises graphene, molybdenum disulfide, or hexagonal boron nitride. In more particular embodiments, the two-dimensional material can be graphene. Graphene can includes single-layer graphene, multi-layer graphene, or any combination thereof. Other nanomaterials having an extended two-dimensional molecular structure can also constitute the two-dimensional material in the some embodiments. For example, molybdenum disulfide is a representative chalcogenide having a two-dimensional molecular structure, and other various chalcogenides can constitute the two-dimensional material in some embodiments. Choice of a suitable two-dimensional material for a particular application can be determined by a number of factors, including the chemical and physical environment into which the graphene or other two-dimensional material is to be terminally deployed. In some embodiments, materials employed in making an enclosure are biocompatible or can be made biocompatible. In some embodiments, combinations of two-dimensional materials may be used in a multilayer or multi-sheet configuration to make an enclosure. For example, a first two-dimensional material in the multilayer or multi-sheet configuration, nearer an interior of an enclosure, could provide structural support while a second two-dimensional material of the multilayer or multi-sheet configuration, nearer the external environment, could impart biocompatibility.

The process of forming holes in graphene and other two-dimensional materials will be referred to herein as "perforation," and such nanomaterials will be referred to herein as being "perforated." In a graphene sheet an interstitial aperture is formed by each six carbon atom ring structure in the sheet and this interstitial aperture is less than one nanometer across. In particular, this interstitial aperture is believed to be about 0.3 nanometers across its longest dimension (the center to center distance between carbon atoms being about 0.28 nm and the aperture being somewhat smaller than this distance). Perforation of sheets comprising two-dimensional network structures typically refers to formation of holes larger than the interstitial apertures in the network structure.

Due to the atomic-level thinness of graphene and other two-dimensional materials, it can be possible to achieve high liquid throughput fluxes during separation or filtration processes, even with holes that are in the ranges of from 0.3 to 10 nm, from 1 to 10 nm, from 5 to 10 nm, from 5 to 20 nm, from 10 nm to 50 nm, from 50 nm to 100 nm, from 50 nm to 150 nm, from 100 nm to 200 nm, or from 100 nm to 500 nm.

Chemical techniques can be used to create holes in graphene and other two-dimensional materials. Exposure of graphene or another two-dimensional material to ozone or atmospheric pressure plasma (e.g., an oxygen/argon or nitrogen/argon plasma) can effect perforation.

In some embodiments, holes can be created using focused ion beam drilling, ion bombardment, nanoparticle bombardment, and combinations thereof. In some embodiments, lithographic techniques can be used to remove matter from the planar structure of two-dimensional materials to create holes.

In various embodiments, the holes produced in the graphene or other two-dimensional material can range from about 0.3 nm to about 50 nm in size. In some embodiments, hole sizes can range from 1 nm to 50 nm. In some embodiments, hole sizes can range from 1 nm to 10 nm. In some embodiments, hole sizes can range from 5 nm to 10 nm. In some embodiments, hole sizes can range from 1 nm to 5 nm. In some embodiments, the holes can range from about 0.5 nm to about 2.5 nm in size. In some embodiments, the hole size is from 0.3 to 0.5 nm. In some embodiments, the hole size is from 0.5 to 10 nm. In some embodiments, the hole size is from 5 nm to 20 nm. In some embodiments, the hole size is from 0.7 nm to 1.2 nm. In some embodiments, the hole size is from 10 nm to 50 nm. In some embodiments where larger hole sizes are preferred, the hole size is from 50 nm to 100 nm, from 50 nm to 150 nm, or from 100 nm to 200 nm.

The term substance is used generically herein to refer to atoms, ions, molecules, macromolecules, viruses, cells, particles and aggregates thereof. Substances of particular interest are molecules of various size, including biological molecules, such as DNA, RNA, proteins and nucleic acids. Substances can include pharmaceuticals, drugs, medicaments and therapeutics, which include biologics and small molecule drugs.

FIG. 1 shows an illustrative schematic demonstrating the thickness of graphene in comparison to conventional drug delivery vehicles and devices. The biocompatibility of graphene can further promote this application, particularly by functionalizing the graphene to be compatible with a particular biological environment (e.g., via available edge bonds, bulk surface functionalization, pi-bonding, and the like). Functionalization can provide membranes having added complexity for use in treating local and systemic disease. FIG. 1 illustrates a wall of an enclosure formed with perforated two-dimensional material having hole sizes in the range of 400-700 nm which will retain active cells. The external biological environment abutting the enclosure (the full enclosure is not shown) is illustrated with an optional porous substrate layer adjacent and external to the perforated two-dimensional material and an optional woven support material external to the perforated two-dimensional material. As illustrated, implantation of such an enclosure contemplates vascularization into any such substrate layer materials. In some embodiments intended to provide immunoisolation, hole sizes can be tailored to prevent entrance of antibodies into the enclosure.

In various embodiments, sealed enclosures, primarily formed from a two-dimensional material, such as graphene, that remain capable of bi-directional transportation of materials. In various embodiments, at least one section or panel of the enclosure contains appropriately sized perforations in the two-dimensional material to allow ingress and egress, respectively, of materials of a desired size to and from the interior of the enclosure.

In some embodiments, the two-dimensional material, such as graphene, can be affixed to a suitable porous substrate. Suitable porous substrates can include, for example, thin film polymers; ceramics and inorganic materials, such as $Si_3N_4$, $SiO_2$, Si; thin metal films (e.g., Ti, Au); track-etched polyimide; polycarbonate; PET; and combinations thereof.

In some embodiments, the enclosure comprises two or more two-dimensional material layers. In some embodiments, an intermediate layer is positioned between two separate two-dimensional layers. In some embodiments, the intermediate layer is porous. In some embodiments, the intermediate layer comprises carbon nanotubes, lacey carbon, nanoparticles, lithographically patterned low-dimensional materials, silicon and silicon nitride micromachined material, a fine mesh, such as a transmission electron microscopy grid, or combinations of these.

In some embodiments, the intermediate layer is functionalized. In some embodiments, functionalization comprises surface charges (e.g., sulfonates) attached to or embedded in the intermediate layer. Without being bound by theory, it is believed that surface charges can impact molecules and/or ions that can traverse the membrane. In some embodiments, functionalization comprises specific binding sites attached to or embedded in the intermediate layer. In some embodiments, functionalization comprises proteins or peptides attached to or embedded in the intermediate layer. In some embodiments, functionalization comprises antibodies and/or antigens (e.g., IgG-binding antigens) or an antibody-binding fragment thereof attached to or embedded in the intermediate layer. In some embodiments, functionalization comprises adsorptive substances attached to or embedded in the intermediate layer. In some embodiments, functionalization involves catalytic and/or regenerative substances or groups. In some embodiments, functionalization comprise a negatively or partially negatively charged group (e.g., oxygen) attached to or embedded in the intermediate layer. In some embodiments, functionalization comprises a positively or partially positively charged group attached to or embedded in the intermediate layer. In some embodiments, the functionalization moieties are free to diffuse within the intermediate layer. In some embodiments, the functionalization moieties are trapped between two two-dimensional material layers, but are not restricted to a single position in the channel (i.e., they are mobile within the intermediate layer, but are inhibited from traversing the two-dimensional material layers, e.g., based the size of the pores in the two-dimensional material layers). In some embodiments, functionalization of the intermediate layer functions as an entrainment layer, and inhibits substances from traversing the membrane that would be able to traverse the membrane absent the functionalization. Thus, in some embodiments functionalization imparts a selective permeability upon the membrane based on properties of potential permeants such as charge, hydrophobicity, structure, etc.

In some embodiments, a substrate layer is disposed on one or both surfaces of the graphene-based material layer. Without being bound by theory, it is believed that the substrate layer can improve biocompatibility of membranes, for instance by reducing biofouling; preventing protein adsorption-related problems; enhancing vascularization and/or tissue ingrowth or distribution; supporting cells; and/or separating cells to prevent or inhibit clumping or agglomerating. In some embodiments, the substrate layer can increase vascularization near the enclosure, thus prompting the formation of blood vessels and/or tissue ingrowth in close proximity to the enclosure.

In some embodiments, the substrate is disposed directly on the graphene-based material layer. In some embodiments, the substrate is disposed indirectly on the graphene-based material layer; for instance, an intermediate layer can be positioned between the substrate layer and the graphene-based material layer. In some embodiments, the graphene-based material layer is suspended on a substrate layer. In some embodiments, the substrate layer is affixed to the graphene-based material layer.

The substrate layer can be porous and/or nonporous. In some embodiments, the substrate layer contains porous and nonporous sections. In some embodiments the substrate layer comprises a porous or permeable fibrous layer. Porous substrates include, for example, one or more of ceramics and thin film polymers. Exemplary ceramics include nanoporous silica (silicon dioxide), silicon, SiN, and combinations thereof. In some embodiments, the substrate layer comprises track-etched polymers, expanded polymers, patterned polymers, woven polymers, and/or non-woven polymers. In some embodiments, the substrate layer comprises a plurality of polymer filaments. In some embodiments, the polymer filaments can comprise a thermopolymer, thermoplastic or melt polymer, e.g., that can be molded or set in an optional annealing step. In some embodiments, the polymer filaments are hydrophobic. In some embodiments, the polymer filaments are hydrophilic. In some embodiments, the substrate layer comprises a polymer selected from the group consisting of polysulfones, polyurethane, polymethylmethacrylate (PMMA), polyglycolid acid (PGA), polylactic acid (PLA), polyethylene glycol (PEG), polylactic-co-glycolic acid (PLGA), polyamides (such as nylon-6,6, supramid and nylamid), polyimides, polypropylene, polyethersulfones (PES), polyvinylidine fluoride (PVDF), cellulose acetate, polyethylene, polypropylene, polycarbonate, polytetrafluoroethylene (PTFE) (such as Teflon), polyvinylchloride (PVC), polyether ether ketone (PEEK), mixtures and block co-polymers of any of these, and combinations and/or mixtures thereof. In some embodiments, the polymers are biocompatible, bioinert and/or medical grade materials.

In some embodiments, the substrate layer comprises a biodegradable polymer. In some embodiments, a substrate layer forms a shell around the enclosure. In some embodiments, the substrate layer shell, or a portion thereof, can be dissolved or degraded, e.g., in vitro.

Suitable techniques for depositing or forming a porous or permeable polymer on the graphene-based material layer include casting or depositing a polymer solution onto the graphene-based material layer or intermediate layer using a method such as spin-coating, curtain coating, doctor-blading, immersion coating, electrospinning, or other similar techniques. Electrospinning technique are described, e.g., in US 2009/0020921 and/or U.S. application Ser. No. 14/609,325, both of which are hereby incorporated by reference in their entirety.

In some embodiments, the process for forming a substrate layer includes an electrospinning process in which a plurality of polymer filaments are laid down to form a porous mat, e.g., on the graphene-based material layer. In some embodiments, the mat has pores or voids located between deposited filaments of the fibrous layer. FIG. 5 shows an illustrative SEM micrograph of a graphene or graphene-based film deposited upon a plurality of electrospun PVDF fibers. In some embodiments, the electrospinning process comprises a melt electrospinning process or a solution electrospinning process, such as a wet electrospinning process or a dry electrospinning process. (See, e.g., Sinha-Ray et al. *J. Membrane Sci.* 485, 1 Jul. 2015, 132-150.) In some embodiments, the polymer can be present in a spin dope at a concentration of 2 wt. % to 15 wt. %, or 5 wt. % to 10 wt. %, or about 7 wt. %. Suitable solvents for the spin dope include any solvent that dissolves the polymer to be deposited and which rapidly evaporates, such as m-cresol, formic acid, dimethyl sulfoxide (DMSO), ethanol, acetone, dimethylacetamide (DMAC), dimethylformamide (DMF), water, and combinations thereof. In some embodiments, the spin dope solvent is biocompatible and/or bioinert. In some embodiments, the amount of solvent used can influence the morphology of the substrate layer. In dry electrospinning processes, the spun fibers of the fibrous layer can remain as essentially discrete entities once deposited. In some embodiments, wet electrospinning processes deposit the spun fibers such that they are at least partially fused together when deposited. In some embodiments, the size and morphology of the deposited fiber mat (e.g., degree of porosity, effective pore size, thickness of fibrous layer, gradient porosity) can be tailor based on the electrospinning process used.

The porosity of the fibrous layer can include effective porosity values—i.e., void space values—(e.g. measured via imagery or porometry methods) of up to about 95% (i.e., the layer is 95% open), about 90%, about 80%, or about 60% with a broad range of pore sizes. In some embodiments, a single spinneret can be moved to lay down a mat of the fibrous layer. In other embodiments, multiple spinnerets can be used for this purpose. In some embodiments, the spun fibers in an electrospun fibrous layer can have a fiber diameter ranging from about 1 nm to about 100 µm, or about 10 nm to about 1 µm, or about 10 nm to about 500 nm, or about 100 nm to about 200 nm, or about 50 nm to about 120 nm, or about 1 µm to about 5 µm, or about 1 µm to about 6 µm, or about 5 µm to about 10 µm. In some embodiments, the fiber diameter is directly correlated with a depth (Z-axis) of a pore abutting the graphene-based material layer (disposed in the X-Y plane), and large diameter fibers can lead to large unsupported spans of material.

In some embodiments, the substrate layer can have pores with an effective pore size of from about 1 nm to about 100 µm, or about 10 nm to about 1 µm, or about 10 nm to about 500 nm, or about 100 nm to about 200 nm, or about 50 nm to about 120 nm, or about 1 µm to about 5 µm, or about 1 µm to about 6 µm, or about 5 µm to about 10 µm. Pore diameters in the substrate layer can be measure, for example, via a bubble point method.

In some embodiments, the substrate layer can have an average pore size gradient throughout its thickness. "Pore size gradient," describes a layer with a plurality of pores, where the average diameter of the pores increases or decreases based on the proximity of the pore to the graphene-based material layer. For example, a fibrous layer can have an average pore size gradient that decreases nearer the surface of a graphene-based material. In some embodiments, an average pore size of the fibrous layer is smaller nearer the surface of the graphene-based material than at an opposite surface of the fibrous layer. For example, the fibrous layer can have effective pore diameters of from about 1 µm to about 6 µm close to the intermediate layer or the graphene-based material layer which can increase to greater than 100 µm at the maximum distance away from the intermediate layer or graphene-based material layer.

In some embodiments, the fibrous layer can have a "porosity gradient" throughout its thickness, which can be measured for instance using imagery. "Porosity gradient," as used herein, describes a change, along a dimension of the fibrous layer, in the porosity or total pore volume as a function of distance from the graphene-based material layer. For example, throughout the thickness of the porous fibrous layer, the porosity can change in a regular or irregular manner. A porosity gradient can decrease from one face of the fibrous layer to the other. For example, the lowest porosity in the fibrous layer can be located spatially closest to the graphene-based material layer, and the highest porosity can be located farther away (e.g., spatially closer to an external environment). A porosity gradient of this type can be achieved by electrospinning fibers onto a graphene-based material layer such that a fiber mat is denser near the surface of the graphene-based material layer and less dense further from the surface of the graphene-based material layer. In some embodiments, a substrate layer can have a relatively low porosity close to the graphene-based material layer, a higher porosity at a mid-point of the fibrous layer thickness (which can, for example, contain a supporting mesh for reinforcement or other particles), and return to a relatively low porosity at an external surface distal to the graphene-based material layer.

In some embodiments, the substrate layer can have a "permeability gradient" throughout its thickness. "Permeability gradient," as used herein, describes a change, along a dimension of the fibrous layer, in the "permeability" or rate of flow of a liquid or gas through a porous material. For example, throughout the thickness of the fibrous layer, the permeability can change in a regular or irregular manner. A permeability gradient can decrease from one face of the fibrous layer to the other. For example, the lowest permeability in the fibrous layer can be located spatially closest to the graphene-based material layer, and the highest permeability can be located farther away. Those of skill in the art will understand that permeability of a layer can increase or decrease without pore diameter or porosity changing, e.g., in response to chemical functionalization, applied pressure, voltage, or other factors.

It should also be noted that in some embodiments, the enclosure can be supported by one or more support structures. In some embodiments, the support structure can itself have a porous structure wherein the pores are larger than those of the graphene-based material layer. In some embodiments, the support structure is entirely porous (i.e., the support structure is formed as a frame at a perimeter of a graphene-based material layer). In some embodiments, the support structure is at least in part non-porous comprising some structure interior to a perimeter of a graphene-based material layer.

In some embodiments, the thickness and structure of the substrate layer can be chosen to convey a desired degree of structural support (e.g., to prevent tearing and/or buckling) to the graphene-based material layer. In various embodiments, the substrate layer can have a thickness of about 1 mm or less, or about 1 µm or less. In some embodiments, a thickness of the substrate layer can range from about 100 nm to about 100 or about 1 µm to about 50 µm, or about 10 µm to about 20 µm, or about 15 µm to about 25 µm. In some embodiments, the substrate layer has a thickness greater than about 5 µm, or greater than about 10 µm, or greater than about 15 µm. In some embodiments, the substrate layer has a thickness of less than 1 µm.

In some embodiments, both the graphene-based material layer and the substrate layer include a plurality of pores therein. In some embodiments, both the graphene-based material layer and the substrate layer contain pores, and the pores in the graphene-based material layer are smaller, on average, than the pores in the substrate layer. In some embodiments, the median pore size in the graphene-based material layer are smaller than the median pore size in the substrate layer. For example, in some embodiments, the substrate layer can contain pores with an average and/or median diameter of about 1 µm or larger and the graphene-based material layer can contain pores with an average and/or median diameter of about 10 nm or smaller. Accordingly, in various embodiments, the average and/or median diameter of pores in the graphene-based material layer are at least about 10-fold smaller than are the average and/or median diameter of pores in the substrate layer. In some embodiments, the average and/or median diameter of pores in the graphene-based material layer are at least about 100-fold smaller than are the average and/or media diameter of pores in the substrate layer.

In some embodiments, the substrate layer can provide a scaffold for tissue growth, cell growth, support, and/or vascularization. In some embodiments, the substrate layer or wall comprises additives, such as pharmaceuticals, cells, growth factors (e.g., VEGF), signaling molecules, cytokines, clotting factors, blood thinners, immunosuppressants, antimicrobial agents, hormones, antibodies, minerals, nutrients or combinations thereof. In some embodiments, additives such as pharmaceuticals, cells, growth factors, clotting factors, blood thinners, immunosuppressants, antimicrobial agents, hormones, antibodies, antigens (e.g., IgG-binding antigens) or an antibody-binding fragment thereof, minerals, nutrients or combinations thereof are positioned on the inside of the disclosure. In some embodiments, the substrate layer or wall comprises materials toxic to bacteria or cells (without being bound by theory, it is believed that incorporating toxic materials into the wall will prevent passage of potentially dangerous cells across the wall).

In some embodiments, additives beneficially promote cell or tissue viability or growth, reduce or prevent infection, improve vascularization to or near the enclosure, improve biocompatibility, reduce biofouling, and/or reduce the risk of adverse reactions. In some embodiments, additives can modulate properties, such as hydrophobicity or hydrophilicity, of the substrate layer. In some embodiments, additives can be used to modulate elution of a substance from a compartment in the enclosure. For instance, additives can confer shell-like properties to a substrate layer, such that degradation or removal of the additives allows substances in the compartment to escape the enclosure (and, by extension, substances from the external environment to enter to enclosure).

Figure 2A:
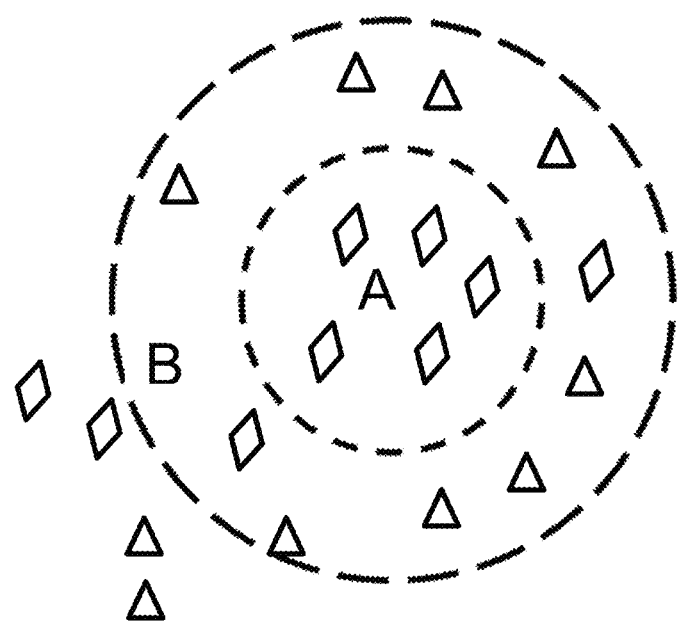
FIGS. 2A-F illustrate some embodiments with various configurations of enclosure configurations.

In some embodiments, the enclosures have a single compartment without sub-compartments. In some embodiments, the enclosures can have a plurality of sub-compartments within the main enclosure each sub-compartment comprises perforated two-dimensional material to allow passage of one or more substance into or out of the sub-compartment. In such embodiments, sub-compartment can have any useful shape or size. In some embodiments, 2 or 3 sub-compartments are present. Several examples of enclosure sub-compartments are illustrated in FIGS. 2A-2F. In FIG. 2A, a nested configuration is illustrated, the main enclosure B completely contains a smaller enclosure A, such that substances in the centermost enclosure A can pass into the main enclosure B, and potentially react with or within the main compartment during ingress and egress therefrom. In this embodiment, one or more substance in A can pass into B and one or more substance in A can be retained in A and not to B. Two sub compartments in which one or more substance can pass directly between the sub-compartments are in direct fluid communication. Passage between sub-compartments and between the enclosure and the external environment is via passage through the holes of a perforated two-dimensional material. The barrier (membrane, i.e. perforated two-dimensional material) between compartment A and B can be permeable to all substances in A or selectively permeable to certain substances in A. The barrier (membrane) between B and the external environment can be permeable to all substances in B or selectively permeable to certain substances in B. In FIG. 2A, sub-compartment A is in direct fluid communication with sub-compartment B which in turn is in direct fluid communication with the external environment. Compartment A in this nested configuration is only in indirect fluid communication with the external environment via intermediate passage into sub-compartment B. The two-dimensional materials employed in different sub-compartments of a given enclosure may be the same or different materials and the perforations or hole sizes in the two-dimensional material of different sub-compartments may be the same or different dependent upon the substances involved and the application.

Figure 2B:
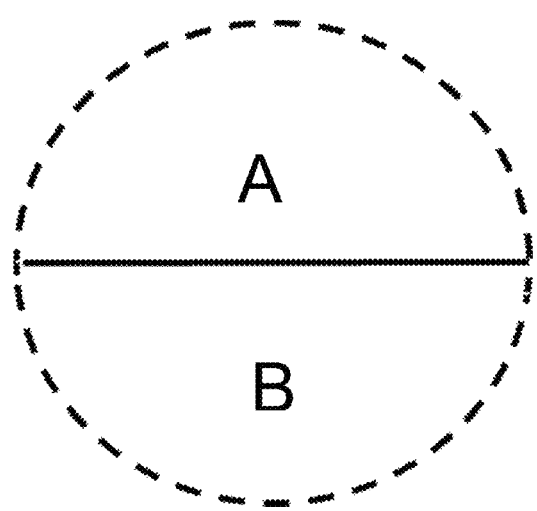

In FIG. 2B the enclosure is bisected with an impermeable wall (e.g., formed of non-porous or non-permeable sealant) forming sub-compartments A and B, such that both sections have access to the egress location independently, but there is no direct or indirect passage of substances from A to B. (It will be appreciated, however, that substances exiting A or B may enter the other sub-compartment indirectly via the external environment.)

Figure 2C:
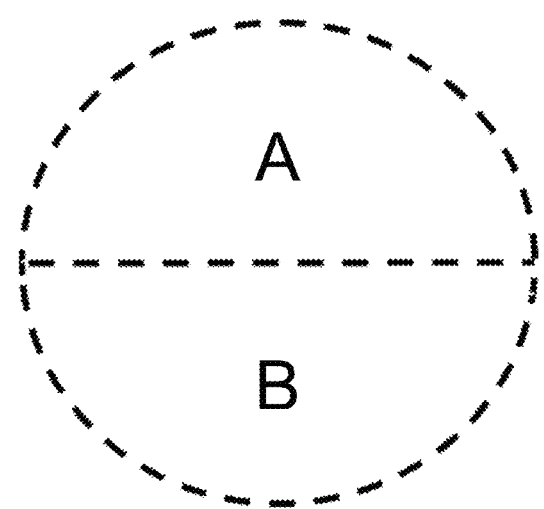

In FIG. 2C the main enclosure is again bisected into sub-compartments A and B, but with a perforated material forming the barrier between the sub-compartments. Both sub-compartments not only have access to the egress location independently, but in some embodiments also can interact with one another, i.e. the sub-compartments are in direct fluid communication. In some embodiments, the barrier (membrane) between compartments A and B is selectively permeable, for example allowing at least one substance in A to pass into B, but not allowing the substances originating in B to pass to A.

Figure 2D:
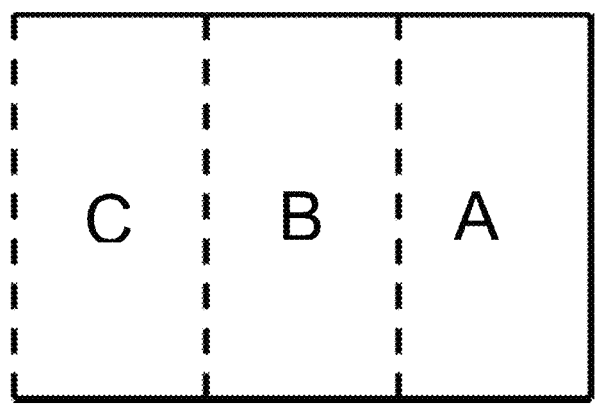

FIG. 2D illustrates an enclosure having three compartments. The enclosure is illustrated with sub-compartment A having egress into sub-compartment B, which in turn has egress into sub-compartment C, which in turn has egress to the external environment. Compartments A and B have no egress to the external environment, i.e. they are not in direct fluid communication with the external environment. Adjacent sub-compartments A and B and adjacent sub-compartments B and C are each separated by a perforated two-dimensional material and are thus in direct fluid communication with each other. Sub-compartment A is only in indirect fluid communication with compartment C and the external environment via sub-compartment B or B and C, respectively. Various other combinations of semi-permeable barrier (membranes) or non-permeable barriers can be employed to separate compartments in the enclosures. Various perforation size constraints can change depending on how the enclosure is ultimately configured (e.g., if one enclosure is within another versus side-by-side). Regardless of the chosen configuration, the boundaries or at least a portion thereof, of the enclosure can be constructed from a two-dimensional material in order to realize the benefits thereof, specifically such that the thickness of the active membrane is less than the diameter of the target to be passed selectively across the membrane. In some embodiments, the pore size of the two-dimensional material can range between about 0.3 nm to about 10 nm in size. Larger pore sizes are also possible.

Figure 2E:
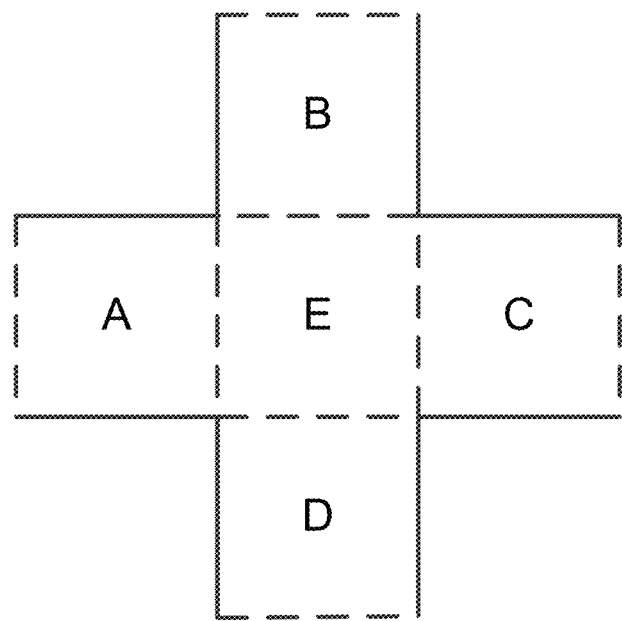

FIG. 2E illustrates an enclosure having multiple compartments in a radial array around a central compartment. In the embodiment shown, central compartment E is surrounded by four compartments A-D. Top and bottom surfaces of compartment E may also be joined to compartments that are not shown. In addition to a square or rectangular shape for compartment E, the central compartment of a radial array may have a hexagonal, octahedral, decahedral, dodecahedral or circular shape to increase the number of connection points for the radially arranged compartments.

The enclosure of FIG. 2E is illustrated with compartment E having egress into compartments A-D, which in turn have egress to the external environment. Compartment E does not have egress to the external environment, i.e. it is not in direct fluid communication with the external environment. Compartments A-D have egress to the external environment through at least one section of permeable two-dimensional membrane, but in some embodiments compartments A-D may be formed entirely by a permeable two-dimensional membrane.

Figure 2F:
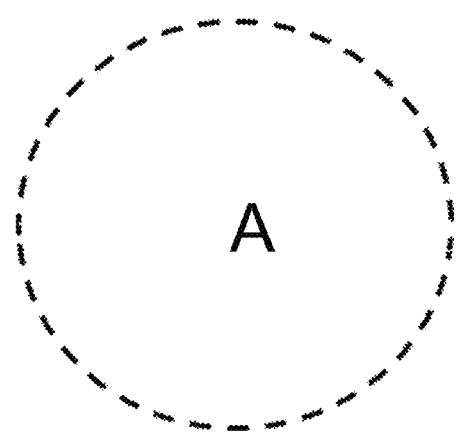

FIG. 2F illustrates an enclosure having a single compartment (A) and no sub-compartments. In the Figure, the compartment is in direct fluid communication with an environment external to the enclosure.

In an example of the operation of an enclosure configured as a radial array, compartment E may independently transfer molecules to, receive molecules from, or exchange molecules with compartments A, B, C and/or D. In some embodiments, compartment E may contain a biological organism producing a molecule that is transferred to one or more of compartments A-D, which may contain different molecules capable of reacting with the molecule produced in the central compartment. In some embodiments, central compartment E may receive one or more molecules from one or more of the radial compartments A-D, such that compartment E acts as a reaction chamber. In such an embodiment, it may be useful for compartments A-D to only have egress to an external environment through central compartment E. The perforated two-dimensional material separating the central compartment from each of the radially arranged compartments may be the same or different in terms of composition and hole size.

In some embodiments, the sub-compartments are connected by microfluidic channels. In some embodiments, the microfluidic channels comprise valves. In some embodiments, substances can diffuse between sub-compartments. In some embodiments, substances can pass between sub-compartments via a tortuous path membrane. In some embodiments, reaction rates between substances in two sub-compartments can be controlled by modulating the ability of the substances to pass from the first sub-compartment to the second sub-compartment, and vice versa.

Some embodiments comprise a device comprising more than one enclosure (such as 2, 3, 4, 5, 6, 7, 8, 9, 10, or more than 10 enclosures), where at least a portion of the enclosures are connected such that a reservoir is formed between the enclosures. In some embodiments, at least a portion of the enclosures are connected by microfluidic channels. In some embodiments, the microfluidic channels comprise valves. In some embodiments, substances can diffuse between at least a portion of the enclosures. In some embodiments, substances can pass between at least a portion of the enclosures via a tortuous path membrane. In some embodiments, reaction rates between substances in different enclosures can be controlled by modulating the ability of the substances to pass from one enclosure to the other enclosure, and vice versa.

Some embodiments comprise two or more enclosures configured in a similar manner to the sub-compartments described above. For instance, two enclosures can be positioned in a nested configuration, where only the outer enclosure is in fluid communication with an environment external to the enclosure. In some embodiments with a nested enclosure configuration, the outermost enclosure comprises a substance that is released over a period of days, weeks, months, or years. In some embodiments, the innermost enclosure comprises a substance that is released after the substance in the outermost enclosure is substantially depleted, at which point the substance from the innermost enclosure can pass through the outermost enclosure and into the external environment. In some embodiments, a polymer protective shell (e.g., a polymer coating) surrounding the inner enclosure is degraded after a certain time period, for instance after the substance in the outermost enclosure is depleted. In some embodiments, devices with more than two nested enclosures can be used. Without being bound by theory, it is believed that a nested enclosure configuration can be used for sustained substance release and/or weaning a subject off a pharmaceutical product.

Some embodiments comprise a means for moving substances and/or fluid between sub-compartments. Some embodiments comprise a means for moving substances and/or fluid between enclosures and/or reservoirs positioned between the enclosures. For instance, passage of substances and/or fluids can be in response to a concentration gradient, electric potential, or pressure difference. In some embodiments, passage of substances and/or fluids can be in response to activating or deactivating electrically gated pores.

In some embodiments, passage of substances and/or fluid is via osmosis. In some embodiments, an osmotic engine is used to influence passage of substances and/or fluids. In some embodiments, osmosis is triggered based on a change in basal cell chemistry. For instance, the presence of antibodies or an immune-mediated response can trigger the release of substances from the enclosure (for example, an immune response could trigger release of antibiotics from the enclosure device).

In some embodiments, a piston is used to influence passage of substances and/or fluids (e.g., the piston can be used to push out or draw in substances/fluids from an enclosure and/or reservoir). In some embodiments, passage of substances and/or fluid between enclosures and/or reservoirs is via an automated or triggered release of the substances and/or fluid. In some embodiments, the passage is triggered by a microchip positioned in or on the device. In some embodiments, the microchip is triggered by a triggering device located external to the enclosure device.

It should also be noted that in some embodiments, the enclosure can be supported by one or more support structures. In some embodiments, the support structure can itself have a porous structure wherein the pores are larger than those of the two-dimensional material. In some embodiments, the support structure is entirely porous. In some embodiments, the support structure is at least in part non-porous.

The multiple physical embodiments for the enclosures and their uses can allow for various levels of interaction and scaled complexity of problems to be solved. For example, a single enclosure can provide drug elution for a given time period, or there can be multiple sizes of perforations to restrict or allow movement of distinct targets, each having a particular size.

In some embodiments, added complexity with multiple sub-compartments can allow for interaction between target compounds to catalyze or activate a secondary response (i.e., a "sense-response" paradigm). For example, if there are two sections of an enclosure that have access to egress independently, exemplary compound A may undergo a constant diffusion into the body, or either after time or only in the presence of a stimulus from the body. In such embodiments, exemplary compound A can activate exemplary compound B, or inactivate functionalization blocking exemplary compound B from escaping. The bindings to produce the foregoing effects can be reversible or irreversible. In some embodiments, exemplary compound A can interact with chemical cascades produced outside the enclosure, and a metabolite subsequent to the interaction can release exemplary compound B (by inactivating functionalization). Further examples utilizing effects that take place in a similar manner include using source cells (non-host, allogenic)

contained in an enclosure, within which secretions from the cell can produce a "sense-response" paradigm.

In some embodiments, growth factors and/or hormones can be loaded in the enclosure to encourage vascularization (see FIG. 1). In the foregoing embodiments, cell survival can be far superior as a result of bi-directional transport of nutrients and waste.

In some embodiments, the relative thinness of graphene can enable bi-directional transport across the membrane enclosure in close proximity to blood vessels, particularly capillary blood vessels, and other target cells. In some embodiments, using a graphene-based enclosure can provide differentiation over other solutions accomplishing the same effect because the graphene membrane is not appreciably limiting the permeability. Thus, in some embodiments the diffusion of molecules through the medium or interstitial connections can limit the movement of a target.

In some embodiments, a "sense-response" paradigm with graphene is enabled by a superior time response. The biocompatibility of graphene can further enhance this application. Further, due to its extreme thinness, graphene is less susceptible to biofouling and clogging than traditional permeable materials and adsorbed species may be removed by electrification of graphene. Expansion to functionalized graphene membranes for added complexity in treating local and systemic disease is also predicted to lower the degree of biofouling, due to electrostatic repulsion by the functional moieties. Additionally, the mechanical stability of graphene can make it suitable to withstand physical stresses and osmotic stresses within the body.

Figure 3A:
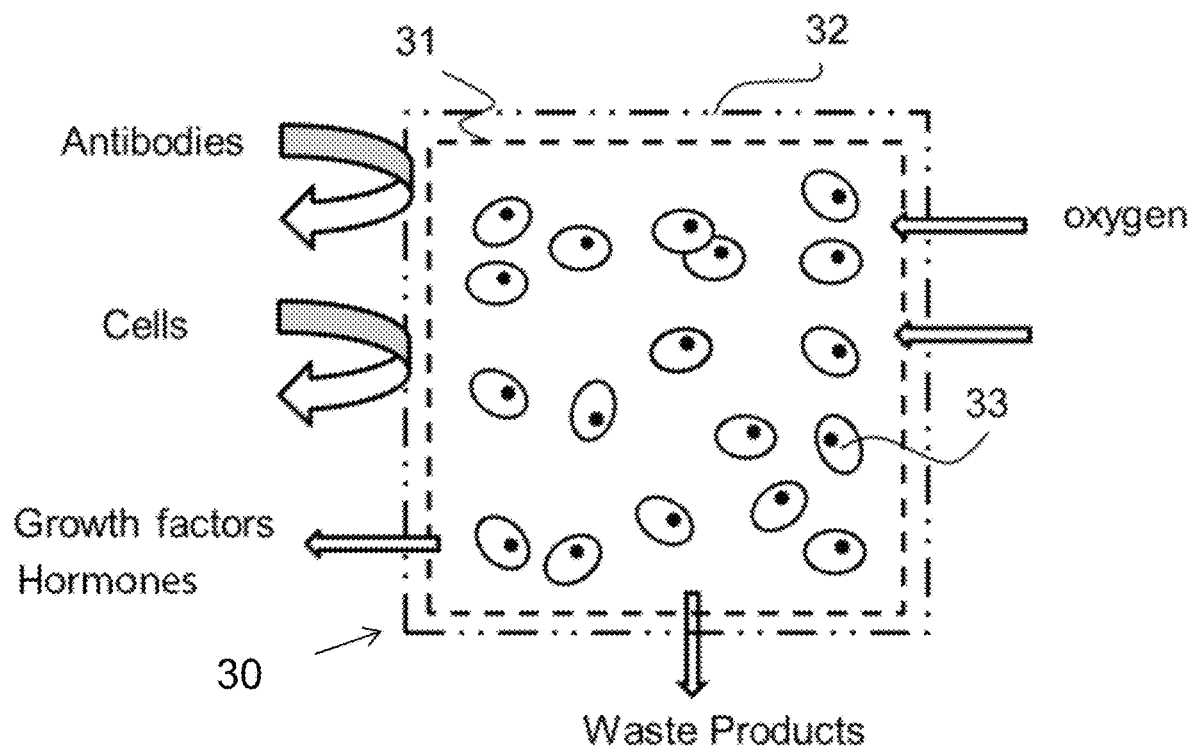
FIGS. 3A and 3B are schematic illustrations of some embodiments of an enclosure implemented for immunoisolation of living cells.
Figure 3B:
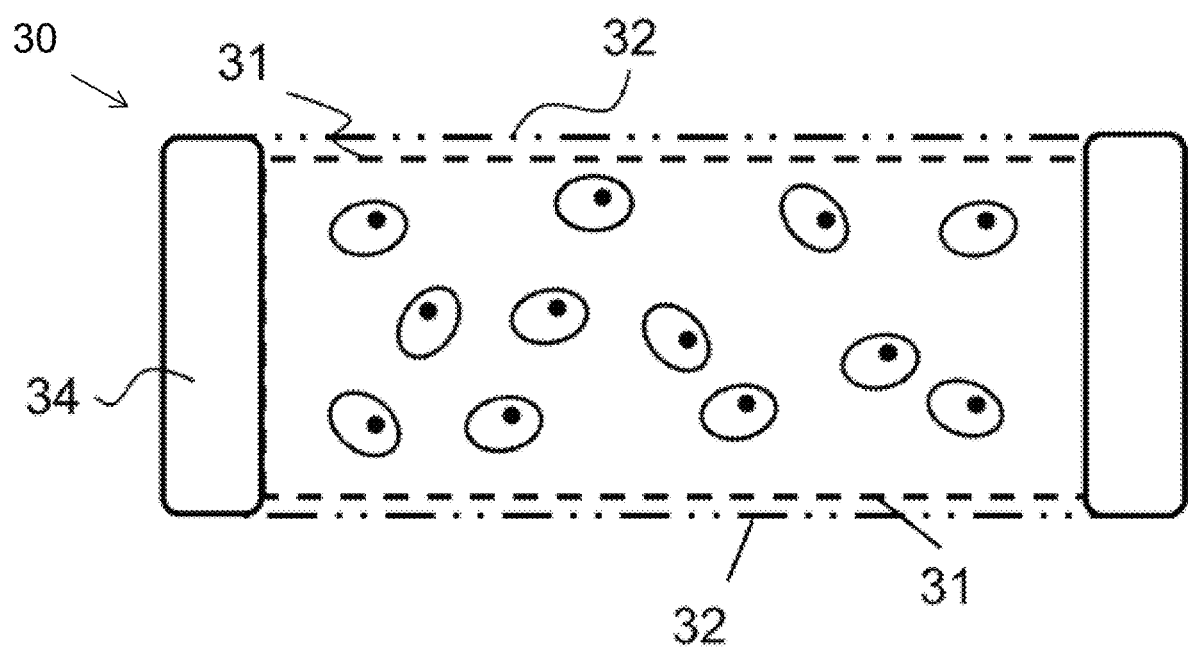

FIGS. 3A and 3B provide a schematic illustration of enclosures with a single compartment for immunoisolation (it will be appreciated that the enclosure can having a plurality of sub-compartments, for example, two or three sub-compartments). The enclosure (30) of FIG. 3A is shown as a cross-section formed by an inner sheet or layer (31) comprising perforated two-dimensional material, such as a graphene-based material, and an outer sheet or layer (32) of a substrate material (though in some embodiments, the inner layer comprises the substrate material, and the outer layer comprises the perforate two-dimensional material). The substrate material can be porous, selectively permeable or non-porous, and/or and non-permeable. However at least a portion of the support material is porous or selectively permeable. The enclosures in FIG. 3 contain selected living cells (33). FIG. 3B provides an alternative cross-section of the enclosure of FIG. 3A, showing the space or cavity formed between a first composite layer (32/31) and a second composite layer (32/31) (in the figure, the cavity is depicted to contain roughly circular symbols, which can be cells or any other substance) where a sealant 34 is illustrated as sealing the edges of the composite layers. It will be appreciated that seals at the edges of the composite layers can be formed employing physical methods, such as clamping, crimping, or with adhesives. Methods and materials for forming the seals at the edges are not particularly limiting. In some embodiments, the sealing material provides a non-porous and non-permeable seal or closure. In some embodiments, a portion of the enclosure is formed from a sealant, such as a silicone, epoxy, polyurethane or similar material. In some embodiments, the sealant is biocompatible. For instance, in some embodiments the seal does not span the entire length or width of the device. In some embodiments, the seal forms a complete loop around the cavity. In some embodiments, the seal is formed as a frame at a perimeter of a two-dimensional material. In some embodiments, the seal is positioned, at least in in part, interior to a perimeter of a two-dimensional material.

If cells are placed within the enclosure, at least a portion of the enclosure can be permeable to oxygen and nutrients sufficient for cell growth and maintenance and permeable to waste products. In some embodiments, the enclosure is not permeable to cells (such as immune cells), viruses, bacteria, antibodies, and/or complements of the immune system. Thus, in some embodiments, cells from the external environment cannot enter the enclosure and cells in the enclosure are retained. In some embodiments, the enclosure is permeable to desirable products, such as growth factors produced by the cells. The cells within the enclosure are immune-isolated. In some embodiments, hole sizes in perforated two-dimensional materials useful for immunoisolation range in size from about 1-20 nm, about 1-10 nm, about 3-10 nm, or about 3-5 nm. In some embodiments, the holes are from about 1 nm to about 30 nm in size, such as about 30 nm, about 20 nm, about 18 nm, about 15 nm, about 10 nm, about 5 nm, or about 3 nm. See, e.g., Song et al., *Scientific Reports*, 6: 23679, doi: 10.1038/srep23679 (2016), which is incorporated herein by reference in its entirety.

FIGS. 4A-4C illustrate an exemplary method for forming an enclosure and introducing selected substances, for example cells therein. The method is illustrated with use of a sealant for forming the enclosure. The exemplary enclosure has no sub-compartment. Enclosures with sub-compartments, for example nested or adjacent sub-compartments can be readily prepared employing the illustrated method. As illustrated in FIG. 4A, a first composite layer or sheet is formed by placing a sheet or layer of two-dimensional material, particularly a sheet of graphene-based material or a sheet of graphene (41), in contact with a support layer (42). At least a portion of the support layer (42) of the first composite is porous or permeable. Pore size of the support layer is generally larger than the holes or apertures in the two-dimensional material employed and may be tuned for the environment (e.g. body cavity). A layer of sealant (44), e.g. silicone, is applied on the sheet or layer of perforated two-dimensional material outlining a compartment of the enclosure wherein the sealant will form a non-permeable seal around a perimeter of the enclosure. Formation of a single compartment is illustrate in FIGS. 4A-4C, however, it will be appreciated that multiple independent compartments within an enclosure can be formed by an analogous process. A second composite layer formed in the same way as the first can be prepared and positioned with the sheet or layer of perforated two dimensional materials in contact with the sealant. (Alternatively, a sealant can be applied to a portion of composite layer and the layer can be folded over in contact with the sealant to form an enclosure. A seal is then formed between the two composite layers. Appropriate pressure may be applied to facilitate sealing without damaging the two-dimensional material or its support. It will be appreciated that an alternative enclosure can be formed by applying a sheet or layer of non-porous and non-permeable support material in contact with the sealant. In this case only a portion of the enclosure is porous and permeable. Sealed composite layers are illustrated in FIG. 4B where it is shown that the sealed layers can be trimmed to size around the sealant to form the enclosure.) The enclosure formed is shown to have an external porous support layer 42, the sheet or layer of perforated two-dimensional material (41) being positioned as an internal layer, with sealant 44 around the perimeter of the enclosure. As illustrated in FIG. 4C, cells or other substances that would be excluded from passage through the perforated to-dimensional sheet or layer can be introduced into the enclosure after it formed by injection through the sealant layer. Any perforation formed by such injection can be sealed as needed. It will be appreciated that substances and cells can be introduced into the enclosure prior to formation of the seal. Those in the art will appreciate that sterilization methods appropriate for the application envisioned may be employed during or after the preparation of the enclosure.

In some embodiments, the invention provides an enclosure comprising perforated two-dimensional material encapsulating a substance, such that the substance is released to an environment external to the enclosure by passage through the holes in the perforated two-dimensional material. In some embodiments, the enclosure encapsulates more than one different substance. In some embodiments, not all of the different substances are released to an environment external to the enclosure. In some embodiments, all of the different substances are released into an environment external to the enclosure. In some embodiments, different substances are released into an environment external to the enclosure at different rates. In some embodiments, different substances are released into an environment external to the enclosure at the same rates.

In some embodiments, the enclosure comprises two or more sub-compartments, wherein at least one sub-compartment is in direct fluid communication with an environment external to the enclosure through holes in a two-dimensional material of the sub-compartment. In some embodiments, each sub-compartment comprises a perforated two-dimensional material and each sub-compartment is in direct fluid communication with an environment external to the enclosure, through holes in the two-dimensional material of each sub-compartment.

In some embodiments, an enclosure is subdivided into two sub-compartments separated from each other at least in part by perforated two-dimensional material, such that the two-sub-compartments are in direct fluid communication with each other through holes in two-dimensional material. In some embodiments, the enclosure is subdivided into two-sub-compartments each comprising two-dimensional material which sub-compartments are in direct fluid communication with each other through holes in two-dimensional material and only one of the sub-compartments is in direct fluid communication with an environment external to the enclosure. In some embodiments, the enclosure is subdivided into two-sub-compartments each comprising two-dimensional material which sub-compartments are in direct fluid communication with each other through holes in two-dimensional material and both of the sub-compartments are also in direct fluid communication with an environment external to the enclosure.

In some embodiments, the enclosure has an inner sub-compartment and an outer sub-compartment each comprising a perforated two-dimensional material, wherein the inner sub-compartment is entirely enclosed within the outer sub-compartment, the inner and outer compartments are in direct fluid communication with each other through holes in two-dimensional material and the inner sub-compartment is not in direct fluid communication with an environment external to the enclosure.

In some embodiments, where an enclosure has a plurality of sub-compartments each comprising a two-dimensional material, the sub-compartments are nested one within the other, each of which sub-compartments is in direct fluid communication through holes in two-dimensional material with the sub-compartment(s) to which it is adjacent, the outermost sub-compartment in direct fluid communication with an environment external to the enclosure, the remaining plurality of sub-compartments not in direct fluid communication with an environment external to the enclosure.

In some embodiments, where the enclosure is subdivided into a plurality of sub-compartments, each comprising a two-dimensional material, each sub-compartment is in direct fluid communication with one or more adjacent sub-compartments, and only one sub-compartment is in direct fluid communication with an environment external to the enclosure.

In some embodiments, the enclosure comprises two sub-compartments, where (i) the first sub-compartment is in fluid communication with an environment external to the enclosure and comprises a substance such as a pharmaceutical, a drug, a medicament, a therapeutic, a biologic, a small molecule, and combinations thereof and (ii) the second compartment comprises a semi-permeable membrane not abutting the first sub-compartment. In some embodiments, osmosis occurs across the semi-permeable membrane in the second sub-compartment, thereby increasing pressure on the first sub-compartment (e.g., using a piston-like driving force). In some embodiments, this increased pressure increases the diffusion rate of the substance in the first sub-compartment into the environment external to the enclosure.

In some embodiments, the at least one substance within the enclosure that is released to an environment external to the enclosure through holes in two-dimensional material is a pharmaceutical, therapeutic or drug. In some embodiments, e.g., when the released substance is a pharmaceutical, therapeutic or drug, the two-dimensional material of the enclosure for release of the substance comprises holes ranging in size from 1-50 nm. In some embodiments, e.g., when the released substance is a pharmaceutical, therapeutic or drug, the two-dimensional material of the enclosure for release of the substance comprises holes ranging in size from 1-10 nm.

In some embodiments, the substance within the enclosure is cells and the size of the holes in the two-dimensional material is selected to retain the cells within the enclosure and to exclude immune cells and antibodies from entering the enclosure from an environment external to the enclosure. In some embodiments, useful for cells, the enclosure is divided into a plurality of sub-compartments and one or more sub-compartments contain cells. An enclosure can contain different cells with a sub-compartment or different cells within different sub-compartments of the same enclosure. In some embodiments useful for cells, the enclosure is a nested enclosure wherein the cells are within the inner sub-compartment.

In some embodiments, an enclosure has an inner sub-compartment and an outer sub-compartment each comprising a perforated two-dimensional material wherein the inner sub-compartment is entirely enclosed within the outer sub-compartment, the inner and outer compartments are in direct fluid communication through holes in two-dimensional material of the inner sub-compartment, the inner sub-compartment is not in direct fluid communication with an environment external to the enclosure and the outer compartment is in direct fluid communication with an environment external to the enclosure.

In some embodiments useful with cells, an enclosure has a plurality of sub-compartments each of which comprises perforated two-dimensional material and each of which sub-compartments is in direct fluid communication with one or more adjacent sub-compartments, the cells being within one or more cell-containing sub-compartments each of which are not in direct fluid communication with an environment external to the enclosure.

In some embodiments of enclosures containing cells, the cells are yeast cells or bacterial cells. In some embodiments of enclosures containing cells, the cells are mammalian cells. In some embodiments of enclosures containing cells, the size of the holes, in the two-dimensional material of the enclosure or sub-compartment, ranges from 1-10 nm, 3-10 nm, or from 3-5 nm.

In some embodiments, two-dimensional material in the enclosure is supported on a porous substrate. In some embodiments, the porous substrate can be polymer or ceramic.

In some embodiments the two-dimensional material is a graphene-based material. In some embodiments, the two-dimensional material is graphene.

In some embodiments, at least a portion of the holes, or a portion thereof, in the two-dimensional materials of the enclosure are functionalized. In some embodiments, the external surface of the enclosure is functionalized. In some embodiments, functionalization comprises surface charges (e.g., sulfonates) attached to the pores and/or surface of the enclosure. Without being bound by theory, it is believed that surface charges can impact molecules and/or ions that can traverse the membrane. In some embodiments, functionalization comprises specific binding sites attached to the pores and/or the surface of the enclosure. In some embodiments, functionalization comprises proteins or peptides attached to the pores and/or the surface of the enclosure. In some embodiments, functionalization comprises adsorptive substances attached to the pores and/or the surface of the enclosure. In some embodiments, functionalization involves catalytic and/or regenerative substances or groups. In some embodiments, functionalization comprise a negatively or partially negatively charged group (e.g., oxygen) attached to the pores and/or the surface of the enclosure. In some embodiments, functionalization comprises a positively or partially positively charged group attached to the pores and/or the surface of the enclosure.

In some embodiments, functionalizing the pores and/or the surface of the enclosure functions: to restrict contaminants from traversing the membrane; to act as a disposable filter, capture, or diagnostic tool; increase biocompatibility (e.g., when polyethylene glycol is used for functionalization); increase filtration efficiency; and/or to increase selectivity at or near the pores or in asymmetric membranes.

In some embodiments, at least a portion of the two-dimensional material is conductive and a voltage can be applied to at least a portion of the conductive two-dimensional material. The voltage can be an AC or DC voltage. The voltage can be applied from a source external to the enclosure. In some embodiments, a device comprising a two-dimensional material (such as an enclosure device) further comprises connectors and leads for application of a voltage from an external source to the two-dimensional material.

Some embodiments comprise methods of employing an enclosure in a selected environment for delivery of one or more substance to the environment. In some embodiments, the environment is a biological environment. In some embodiments, the enclosure is implanted into biological tissue. In some embodiments, the enclosure device is positioned such that the device or enclosure is positioned partially inside a subject's body and partially outside a subject's body (e.g., an enclosure can be used as a port or wound covering to allow drugs or biologics to be introduced without cells or other contaminants entering the body). In some embodiments, the enclosure is injected (e.g., through a needle). In some embodiments, the enclosure is ingested. In some embodiments, the enclosure is employed for delivery of a pharmaceutical, a drug or a therapeutic.

In some embodiments the invention provides a method comprising introducing an enclosure comprising perforated two-dimensional material into a an environment, the enclosure containing at least one substance; and releasing at least a portion of at least one substance through the holes of the two-dimensional material to the environment external to the enclosure. In some embodiments, the enclosure contains cells which are not released from the enclosure and the at least one substance a portion of which is released is a substance generated by the cells in the enclosure.

In some embodiments the invention provides a method comprising introducing an enclosure comprising perforated two-dimensional material to an environment, the enclosure containing at least one first substance; and receiving a second substance from the environment into the enclosure. In some embodiments, the first substance is cells, a second substance is nutrients and another second substance is oxygen.

In some embodiments, the support layer can be a polymer or a ceramic material. Useful exemplary ceramics include nanoporous silica, silicon or silicon nitride. Useful porous polymer supports include solution-diffusion membranes, track-etched polymers, expanded polymers or non-woven polymers. The support material can be porous or permeable. A portion, e.g., a wall, side or portion thereof, of an enclosure or a sub-compartment can be non-porous polymer or ceramic. Biocompatible polymers and ceramics are preferred. A portion of the enclosure can be formed from a sealant, such as a silicone, epoxy, polyurethane or similar material. Biocompatible sealants are preferred.

In some embodiments, a non-perforated wall or portion thereof of an enclosure is a metallic, polymeric or ceramic material. Biocompatible metals, polymers and ceramics are preferred, such as medical grade materials. In some embodiments, a non-perforated wall of an enclosure may be treated, e.g., on a surface interfacing with an external environment, to provide or improve biocompatibility.

Additionally, the conductive properties of graphene-based or other two-dimensional membranes can allow for electrification to take place from an external source. In exemplary embodiments, an AC or DC voltage can be applied to conductive two-dimensional materials (e.g., in a device such as an enclosure device). The conductivity properties of graphene can provide additional gating to charged molecules or substances. Electrification can occur permanently or only a portion of the time to affect gating. Directional gating of charged molecules can be directed not only through the pores (or restrict travel through pores), but also to the surface of the graphene to adsorb or bind and encourage growth, promote formation of a protective layer, or provide the basis or mechanism for other biochemical effects (e.g., on the body).

In some embodiments, the membranes allow for electrostatic control of charged species, for instance in nanofluidic or microfluidic systems. In some embodiments, the membranes allow for control of charged species by varying the applied voltage, for instance in nanofluidic or microfluidic systems. In some embodiments, the membrane can be tuned to manipulate ion transport at low and/or high ion concentrations. In some embodiments, the membrane is an ion-selective membrane. In some embodiments, the membrane comprises one or more voltage-gated ion channels, such as voltage-gated pores. In some embodiments, the membranes mimic biological voltage-gated ion channels. Inn some embodiments, the gated graphene functions as an artificial membrane, e.g., when used in an artificial organ or organelle. In some embodiments, the membrane is a solid-state membrane. In some embodiments, nanochannel or nanopore transistors can be used to manipulate ion transport.

In some embodiments, the membrane can be tuned using low or high applied voltages. In some embodiments, the membrane allows high ionic flux. In some embodiments, the membrane allows low ion flux. In some embodiments, pores in the membrane modulate current of ions at low gate voltages and/or display high selectivity. In some embodiments, ion flux across the membrane can be turned on or off at low applied voltages, such as ≤500 mV. In some embodiments, ion flux across the membrane can be turned on or off at biologically relevant ion concentrations, such as up to 1 M. In some embodiments, the applied voltage can modulate on species selectivity, e.g., cation or anion selectivity.

In some embodiments, nanopores can be electrostatically controlled at low voltages and biologically relevant ion concentrations. In some embodiments, membranes are used in separation and sensing technologies. In some embodiments, membranes are used in water filtration, energy storage, microfluidic devices, nanofluidic devices, and/or therapeutic methods. Thus, some embodiments relate to methods for separating ions or other substances; methods for sensing ions; methods for storing energy; methods for filtering water; and/or methods of treating a disease or condition. Some embodiments relate to methods of nanofiltration and/or microfiltration. Some embodiments comprise using gating to control release of substances. Some embodiments comprise using gating to allow for different substances to be release at different times. Some embodiments comprise allowing different substances to pass through the membrane at different times, thus modulating when and how substances mix and interact with other substances in a specific order.

Both permanent and temporary binding to the graphene is possible in such embodiments. In addition to the foregoing advantages, some embodiments can also be advantageous in that they not only represent a disruptive technology for state of the art vehicle and other devices, but they can also permit these vehicles and devices to be used in new ways. For example, cell line developments, therapeutic releasing agents, and/or sensing paradigms (e.g., MRSw's, NMR-based magnetic relaxation switches, see; Koh et al. (2008) Ang. Chem. Int'l Ed. Engl, 47(22) 4119-4121) can be used to mitigate biofouling and bioreactivity, conveying superior permeability and less delay in response, and providing mechanical stability. That is, the enclosures can allow existing technologies to be implemented in ways not previously possible.

Some embodiments comprise enclosures where graphene allows implementation of a sense-response system. For instance, graphene can be used to sense a variety of biomolecules, such as insulin. In some embodiments, the biomolecules are "sensed" based on an interaction between compounds with the graphene or with functional groups attached to the graphene. Without being bound by theory, it is believed that the sense-response paradigm provides a feedback mechanism for monitoring the state of encapsulated materials.

Some embodiments comprise bioartificial liver configurations comprising an enclosure. For instance, hepatocytes or liver cells can be encapsulated by the enclosure. In some embodiments, enclosures comprising encapsulated hepatocytes is implanted into a subject in need thereof, such as a subject with impaired liver function. In some embodiments, enclosures comprising encapsulated hepatocytes are used in an extracorporeal medical procedure. In some embodiments, the enclosure is loadable or reloadable, such that a metabolite can be injected into the enclosure to elicit a reaction, or the number or type of cells inside the enclosure can be modified (e.g., the cells inside the enclosure can be replaced).

Some embodiments comprise artificial kidney configurations comprising an enclosure. For instance, kidney cells can be encapsulated by the enclosure. In some embodiments, enclosures comprising encapsulated kidney cells can be implanted into a subject in need thereof. In some embodiments, the enclosure is loadable or reloadable, such that a metabolite can be injected into the enclosure to elicit a reaction, or the number or type of cells inside the enclosure can be modified (e.g., the cells inside the enclosure can be replaced).

Some embodiments comprise artificial lungs comprising an enclosure. In some embodiments, the compartment in the enclosure is in gaseous communication with an environment external to the compartment.

In addition to the in vivo and in vitro uses described above, some embodiments can be utilized in other areas as well. Some embodiments can be used in non-therapeutic applications such as, for example, the dosage of probiotics in dairy products (as opposed to the presently used microencapsulation techniques to increase viability during processing for delivery to the GI tract). In this regard and others, it should be noted that the enclosures and devices formed therefrom can span several orders of magnitude in size, depending on manufacturing techniques and various end use requirements. Nevertheless, the enclosures are believed to be able to be made small enough to circulate through the bloodstream. On the opposite end of the spectrum, the enclosures can be made large enough to implant (on the order of a few inches or greater). These properties can result from the two-dimensional characteristics of the graphene and its growth over large surface areas.

Although the disclosure has been described with reference to the disclosed embodiments, one having ordinary skill in the art will readily appreciate that these are only illustrative of the disclosure. It should be understood that various modifications can be made without departing from the spirit of the disclosure. The disclosure can be modified to incorporate any number of variations, alterations, substitutions or equivalent arrangements not heretofore described, but which are commensurate with the spirit and scope of the disclosure. Additionally, while various embodiments of the disclosure have been described, it is to be understood that aspects of the disclosure may include only some of the described embodiments. Accordingly, the disclosure is not to be seen as limited by the foregoing description.

Specific names of compounds are intended to be exemplary, as it is known that one of ordinary skill in the art can name the same compounds differently. When a compound is described herein such that a particular isomer or enantiomer of the compound is not specified, for example, in a formula or in a chemical name, that description is intended to include each isomers and enantiomer of the compound described individual or in any combination. One of ordinary skill in the art will appreciate that methods, device elements, starting materials and synthetic methods other than those specifically exemplified can be employed without resort to undue experimentation. All art-known functional equivalents, of any such methods, device elements, starting materials and synthetic methods are intended to be included in this invention.

Whenever a range is given in the specification, for example, a temperature range, a time range, or a composition range, all intermediate ranges and subranges, as well as all individual values included in the ranges given are intended to be included in the disclosure. When a Markush group or other grouping is used herein, all individual members of the group and all combinations and subcombinations possible of the group are intended to be individually included in the disclosure.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. Any recitation herein of the term "comprising", particularly in a description of components of a composition or in a description of elements of a device, is understood to encompass those compositions and methods consisting essentially of and consisting of the recited components or elements. The invention illustratively described herein suitably may be practiced in the absence of any element or elements, limitation or limitations which is not specifically disclosed herein.

The terms and expressions which have been employed are used as terms of description and not of limitation, and there is no intention in the use of such terms and expressions of excluding any equivalents of the features shown and described or portions thereof, but it is recognized that various modifications are possible. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In general the terms and phrases used herein have their art-recognized meaning, which can be found by reference to standard texts, journal references and contexts known to those skilled in the art. The preceding definitions are provided for clarity.

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

All patents and publications mentioned in the specification are indicative of the levels of skill of those skilled in the art to which the invention pertains. References cited herein are incorporated by reference herein in their entirety to indicate the state of the art, in some cases as of their filing date, and it is intended that this information can be employed herein, if needed, to exclude (for example, to disclaim) specific embodiments that are in the prior art. For example, when a compound is claimed, it should be understood that compounds known in the prior art, including certain compounds disclosed in the references disclosed herein (particularly in referenced patent documents), are not intended to be included in the claims.

What is claimed is the following:

1. A device comprising a first enclosure and a second enclosure,
wherein the first enclosure and the second enclosure are in direct fluid communication with one another,
wherein the enclosures independently comprise two or more stacked single layers of chemical vapor deposition graphene encapsulating a compartment, or a portion thereof, with at least one substance,
wherein the enclosures contain nanoparticle bombardment-created pores across the chemical vapor deposition graphene,
wherein the first enclosure and/or second enclosure allows release of the substance to an environment external to the device via passage across the pores in the chemical vapor deposition graphene, and
wherein the first and/or second enclosure comprises a central compartment E surrounded by four compartments A-D, wherein compartment E comprises egress into compartments A-D, compartments A-D comprise egress to the environment external to the device and wherein compartment E does not comprise egress into the external environment.

2. The device of claim 1, wherein the first enclosure and the second enclosure are connected by microfluidic channels.

3. The device of claim 1, wherein the first enclosure and the second enclosure are in direct fluid contact via microfluidic channels.

4. The device of claim 1, comprising more than two enclosures, wherein each enclosure is in direct fluid contact with at least one other enclosure.

5. The device of claim 1, wherein fluids and/or the substance pass between the first enclosure and the second enclosure.

6. The device of claim 5, wherein the fluids and/or the substance pass between the first enclosure and the second enclosure via osmosis, applied electric potential, concentration gradients, diffusion, piston-induced transport, triggered movement, or a combination thereof.

7. The device of claim 1, further comprising an osmotic pump that promotes passage of fluids and/or the substance between the first enclosure and the second enclosure.

8. The device of claim 1, wherein the substances in the first enclosure are released into an environment external to the device at a different rate and/or at different relative concentration than substances in the second enclosure.

9. The device of claim 1, wherein the first enclosure is in direct fluid communication with the environment external to the device, wherein the second enclosure is in direct fluid communication with the first enclosure, and wherein the second enclosure is not in direct fluid communication with the environment external to the device.

10. The device of claim 1, wherein each compartment comprises two or more stacked single layers chemical vapor deposition graphene containing pores.

11. The device of claim 1, wherein the substance is selected from the group consisting of atoms, ions, molecules, macromolecules, viruses, particles, pharmaceuticals, drugs, medicaments, therapeutics, small molecules, and combinations thereof.

12. An artificial liver comprising a first enclosure and a second enclosure in direct fluid contact with one another, wherein the first and/or second enclosure comprises a central compartment E surrounded by four compartments A-D, wherein compartment E comprises egress into compartments A-D, compartments A-D comprise egress to an environment external to the artificial liver and wherein compartment E does not comprise egress into the external environment wherein two or more stacked single layers of chemical vapor deposition graphene encapsulate the compartments,
   wherein the two or more stacked single layers of chemical vapor deposition graphene contains nanoparticle bombardment-created pores, and the first enclosure and/or second enclosure allows release of the substance to the environment external to the artificial liver via passage across the pores in the stacked single layers of chemical vapor deposition graphene.

13. The device of claim 1, further comprising
a means for moving substances and/or fluids between the first enclosure and the second enclosure.

14. The device of claim 13, wherein the means comprises osmosis, applied electric potential, concentration gradients, diffusion, piston-induced transport, triggered movement, or a combination thereof.

15. The device of claim 1, wherein the enclosures independently comprise 2 to 5 stacked single layers of chemical vapor deposition graphene.

16. The device of claim 1, wherein the enclosures further comprise one or more support structures.

17. The device of claim 16, wherein the enclosures comprise two support structures different from one another.

18. The device of claim 17, wherein one of the support structures comprises polymeric fibers.

19. The device of claim 17, wherein one of the support structures comprises carbon nanotubes.

20. The device of claim 1, wherein the first enclosure and/or second enclosure's compartment E is square or rectangular in shape, wherein compartments A-D are each independently joined to compartment E at one of the four different sides of the square or rectangle, respectively, and wherein the compartment E further comprises two additional compartments joined to a top and bottom face of compartment E, respectively.

21. The artificial liver of claim 12, wherein the first enclosure and/or second enclosure's compartment E is square or rectangular in shape, wherein compartments A-D are each independently joined to compartment E at one of the four different sides of the square or rectangle, respectively, and wherein the compartment E further comprises two additional compartments joined to a top and bottom face of compartment E, respectively.

22. The device of claim 13, wherein the first enclosure and/or second enclosure's compartment E is square or rectangular in shape, wherein compartments A-D are each independently joined to compartment E at one of the four different sides of the square or rectangle, respectively, and wherein the compartment E further comprises two additional compartments joined to a top and bottom face of compartment E, respectively.

\* \* \* \* \*